(12) United States Patent
Chen et al.

(10) Patent No.: US 11,518,995 B2
(45) Date of Patent: Dec. 6, 2022

(54) GAPMERS AND METHODS OF USING THE SAME FOR THE TREATMENT OF MUSCULAR DYSTROPHY

(71) Applicants: Children's National Medical Center, Washington, DC (US); The Governors of the University of Alberta, Edmonton (CA)

(72) Inventors: Yi-wen Chen, Washington, DC (US); Toshifumi Yokota, Edmonton (CA); Rika Yokota-Maruyama, Edmonton (CA); Yusuke Echigoya, Fuji-sawa (JP)

(73) Assignees: Children's National Medical Center, Washington, DC (US); The Governors of the University of Alberta, Edmonton (CA)

(*) Notice: Subject to any disclaimer, the term of this patent is extended or adjusted under 35 U.S.C. 154(b) by 0 days.

(21) Appl. No.: 16/649,122

(22) PCT Filed: Sep. 19, 2018

(86) PCT No.: PCT/US2018/051776
§ 371 (c)(1),
(2) Date: Mar. 19, 2020

(87) PCT Pub. No.: WO2019/060432
PCT Pub. Date: Mar. 28, 2019

(65) Prior Publication Data
US 2020/0291398 A1   Sep. 17, 2020

Related U.S. Application Data

(60) Provisional application No. 62/560,665, filed on Sep. 19, 2017.

(51) Int. Cl.
*C12N 15/11* (2006.01)
*C12N 15/113* (2010.01)

(52) U.S. Cl.
CPC ........ *C12N 15/113* (2013.01); *C12N 2310/11* (2013.01); *C12N 2310/315* (2013.01); *C12N 2310/322* (2013.01); *C12N 2310/3231* (2013.01); *C12N 2310/341* (2013.01); *C12N 2310/346* (2013.01)

(58) Field of Classification Search
CPC ... C12N 15/11; C12N 15/113; C12N 2310/11; C12N 2310/341; C12N 2310/113; C12N 2310/3525; C12N 2310/321
See application file for complete search history.

(56) References Cited

U.S. PATENT DOCUMENTS

| 2005/0053981 | A1* | 3/2005 | Swayze | A61P 43/00 435/6.12 |
|---|---|---|---|---|
| 2012/0225034 | A1* | 9/2012 | Belayew | C12N 15/111 424/93.1 |
| 2013/0347136 | A1* | 12/2013 | Emerson, Jr. | C12N 15/113 800/9 |
| 2014/0322169 | A1* | 10/2014 | Harper | C12N 15/113 424/93.2 |
| 2015/0133522 | A1 | 5/2015 | Bassell et al. | |
| 2015/0329865 | A1 | 11/2015 | Lee et al. | |
| 2016/0002624 | A1* | 1/2016 | Dibble | A61K 31/7115 514/44 A |
| 2018/0346906 | A1* | 12/2018 | Lee | A61K 45/06 |
| 2019/0343865 | A1* | 11/2019 | Jones | A61K 31/713 |

FOREIGN PATENT DOCUMENTS

| EP | 2 426 203 | 3/2012 |
|---|---|---|
| WO | 2017/050836 | 3/2017 |

OTHER PUBLICATIONS

Schnütgen et al., A directional strategy for monitoring Cre-mediated recombination at the cellular level in the mouse, Nature Biotechnology, vol. 21, pp. 562-565. (Year: 2003).*

Wallace et al., RNA interference inhibits DUX4-induced muscle toxicity in vivo: implications for a targeted FSHD therapy, Molecular Therapy, vol. 20, pp. 1417-1423. (Year: 2012).*

EP Search Report as received in application No. 18859092.1-111 / 3684378 PCT/US2018051776 dated May 19, 2021, Citing document AW, 12 pages.

Celine Vanderplanck, et al., "The FSHD Atrophic Myotube Phenotype is Caused by DUX4 Expression", Oct. 2011, vol. 6., Issue 10, e26820.

Ann-Charlott Marsollier, et al., "Antisense targeting of 3' end elements involved in DUX4 mRNA processing is an efficient therapeutic strategy for facioscapulohumeral dystrophy: a new gene-silencing approach" Human Molecular Genetics, 2016, 1-11.

* cited by examiner

*Primary Examiner* — Dana H Shin
(74) *Attorney, Agent, or Firm* — Oblon, McClelland, Maier & Neustadt, L.L.P.

(57) ABSTRACT

The disclosure relates to compositions comprising a nucleotide sequence having two domains: a locked nucleic acid (LNA) domain and a DNA gap domain, wherein nucleotide sequence binds to an endogenous DUX4 mRNA sequence disrupts DUX4 expression.

9 Claims, 24 Drawing Sheets

Specification includes a Sequence Listing.

GAPMERS AND METHODS OF USING THE SAME FOR THE TREATMENT OF MUSCULAR DYSTROPHY

CROSS REFERENCE TO RELATED APPLICATION

This application is a national stage filing under 35 U.S.C. § 371 of International Application No. PCT/US2018/051776, filed Sep. 19, 2018, which claims priority to U.S. Provisional Application No. 62/560,665, filed Sep. 19, 2017, the contents of each of which are incorporated herein by reference in its entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 37921_0003U2_SL. The size of the text file is 17 KB, the text file was created on Mar. 19, 2020.

FIELD OF DISCLOSURE

The disclosure relates to compositions comprising nucleotide sequences comprising LNA gapmers and methods of using and administering such nucleotide sequences for, among other things, delivery of nucleic acid sequences to one or a plurality of cells.

BACKGROUND

Muscular Dystrophy (MD) comprises a group of 30 or more inherited disorders which are characterized by muscle weakness and replacement of muscle cells with connective tissue and fat (Emery, 1991). Although all MDs share common characteristics such as muscle weakness and muscle cell death, the disorders differ from one another in terms of their severities (i.e. progression variability), age of onset as well as muscles and other organ systems affected (Barakat-Haddad et al., 2016).

Facioscapulohumeral Muscular Dystrophy (FSHD) is an autosomal dominant disorder characterized by early involvement of muscle weakness and atrophy in facial muscles and shoulder girdle muscles (Padberg, 1982). With disease progression, muscle weakness and atrophy often spreads to the upper arms, pelvic girdle and lower limb muscles (Padberg, 1982). FSHD is the third most common muscular dystrophy, with a birth incidence of approximately 1 in 14,000 (Mostacciuolo et al., 2009). The frequency of occurrence for FSHD is often underestimated due to the high degree of clinical variability in addition to the large proportion of individuals who remain asymptomatic or experience mild symptoms (Deenen et al., 2014). In 1884, Landouzy and Dejerine were first to describe the classical FSHD phenotype with the disease being formerly known as Landouzy-Dejerine's disease (Landouzy & Dejerine, 1884 and Landouzy & Dejerine, 1886). However, it wasn't until 1980 when a rise in interest led to a greater understanding of FSHD, its clinical variability and its genetic complexities (Wijmenga, Padberg & Moerer et al., 1991). When the disorder was first described, FSHD and its association to chromosome 4 was unknown. However, since then, the fundamental cause of FSHD and the finding of D4Z4 reduced alleles at 4q35 has become clearer (Upadhyaya et al., 1997).

FSHD is associated with the deletion of a subset of D4Z4 macrosatellite repeat arrays in the subtelomeric region of chromosome 4, 4q35 (FIG. 1). The genetic defect in FSHD was first identified by a reduction seen in an EcoRI fragment of genomic DNA using the p13E-11 probe compared to healthy individuals (Wijmenga et al., 1992). Non-affected control individuals typically contain between 11 and 100 D4Z4 repeats, with EcoRI fragments being 40-300 kb in size, while FSHD patients carry between 1 and 10 repeats on one allele, with EcoRI fragments being 10-38 kb in size (FIG. 1) (Lunt, 1998). The deletion of a subset of D4Z4 macrosatellite repeat arrays occurs in early embryonic development through mitotic rearrangement (van der Maarel et al., 2000).

There are two forms of FSHD, FSHD1, which occurs in over 95% of cases, and the less common form, FSHD2, which occurs in the other 5% of individuals (Jones et al., 2012). FSHD1 is genetically linked to contractions of the macrosatellite D4Z4 repeat array (Wijmenga et al., 1990), whereas FSHD2 shows chromatin relaxation at D4Z4, but does not have a contraction of the D4Z4 locus (de Greef et al., 2010). In majority of patients with FSHD2, the disease is caused by digenic inheritance of a heterozygous mutation in the chromatin modifier gene on chromosome 18, Structural Maintenance of Chromosomes Flexible Hinge Domain Containing 1 (SMCHD1), as well as a distally located PAS-containing chromosome 4 (Lemmers et al., 2012). SMCHD1 is an important gene known for its role in regulating the repression of the D4Z4 array via DNA CpG methylation (Lemmers et al., 2012). Recent evidence however suggests that there is evidence for locus heterogeneity with FSHD2, due to the lack of SMCHD1 mutations seen in approximately 20% of FSHD2 affected patients. This evidence suggesting the presence of other modifier loci that too are potentially affecting the structure of D4Z4 (Lemmers et al., 2012).

The open reading frame (ORF) for double homeobox 4 (DUX4) gene was mapped in each unit of the D4Z4 repeat arrays remaining after partial deletion associated with FSHD (Gabriels et al., 1999). 4q variants were discovered distal to D4Z4, 4qA and 4qB, both of which occur commonly in the Caucasian population (van Geel et al., 2002). Interestingly, for FSHD, the polyadenylation site is required for a pathogenic contraction of the D4Z4 array and is only intact on the permissive 4qA allele, whereas this signal is missing on the non-permissive 4qB allele (FIG. 1) (Lemmers et al., 2010).

Two full-length isoforms of DUX4 exist with alternative splicing in the 3' untranslated region (Snider et al., 2010). One full-length isoform of DUX4 is detected in FSHD skeletal muscle cells which contains the entire DUX4 ORF and in the 3'UTR has one or two spliced introns, ending in exon 3 (Snider et al., 2009). A second full-length DUX4 mRNA (fl-DUX4) isoform was characterized in induced pluripotent stem cells and in human testis cells by the addition of four exons and a more downstream polyadenylation signal in exon 7 (FIG. 2) (Snider et al., 2010). In control muscles and in other somatic tissues, a shorter DUX4 mRNA variant (s-DUX4) was discovered because of its ability to remove the carboxyterminal end of DUX4 while maintaining the amino-terminal double-homeobox domains, ending in exon 3. s-DUX4 is unique from fl-DUX4 in that it encodes a non-pathogenic protein (Snider et al., 2010).

A high correlation between FSHD disease severity and fragment size has been identified with individuals with a large deletion of the D4Z4 array having earlier-onset disease in addition to rapid progression, compared to those patients with smaller contractions of the D4Z4 locus (Zatz et al., 1995, Tawil et al., 1996 & Bindoff et al., 2006). Currently the existence and precise mechanism for anticipation in FSHD remains uncertain.

It is currently estimated that 10%-30% of FSHD patients carry a new mutation (Padberg et al., 1995 & Zatz et al., 1995), and show an array of D4Z4 array lengths varying from 1 to more than 50 units (van der Maarel et al., 2000). Several studies have shown that approximately half of these reported D4Z4 rearrangements are mitotic in origin, and likely occur from postzygotic array contraction during early cell divisions in embryogenesis, resulting in somatic mosaicism. The other half of de novo cases likely occur before fertilization (Upadhyaya et al., 1995, Lemmers et al., 2004 & van der Maarel et al., 2000).

DUX4 is a double-homeodomain transcription factor encoded within the D4Z4 tandem repeat. DUX4 is a nuclear protein that is normally transcriptionally silenced in healthy individuals after early development; however in FSHD, truncations of the D4Z4 array leading to fewer than 11 units cause a failure to maintain complete suppression of full-length DUX4. Chromatin relaxation of the D4Z4 array (inability to suppress DUX4 fully), causes occasional bursts of DUX4 expression in a small number of skeletal muscle nuclei (Snider et al., 2010). In healthy individuals, DUX4 is normally expressed in early development and silenced during cellular differentiation but maintains expression levels within the seminiferous tubules in male testis (Snider et al., 2010). The primary role of DUX4 remains unclear, however some previously identified targets include cancer-testis antigens, as well as a broad set of genes involved in germ cell maintenance and development and stem cell biology (Geng et al., 2012).

Unlike other disorders which are caused by structural mutations within the disease gene, FSHD involves an intricate cascade of epigenetic events after the deletion of a subset of D4Z4 macrosatellite repeat arrays (van der Maarel, Frants & Padberg, 2007). Several studies have shown that DUX4 expression induces the expression of genes involved in muscle atrophy, such as muscle RING finger 1 (MuRF1) and atrogin-1/MAFbx, sensitizes cells to oxidative stress, thereby inducing the expression of mu-crystallin (CRYM), inhibits the MYOD1 gene resulting in differentiation abnormalities, and causes a p53-dependent myopathy in mouse muscles in vivo (de Palma et al., 2008, Vie et al., 1997 and Wallace et al., 2011). Recent evidence has also shown that paired-like homeodomain 1 (PITX1), tripartite motif containing 43 (TRIM43), and methyl-CpG binding domain protein 3-like 2 (MBD3L2) are also upregulated in FSHD (Dixit et al., 2007 and Ferreboeuf et al., 2014) (FIG. 3).

Despite the progress made in understanding the underlying genetic and pathophysiological complexities of FSHD, no curative treatment options have been established. Currently, standard disease management options include physical therapy, exercise, management of respiratory dysfunction and orthopedic intervention (Tawil et al., 2014).

SUMMARY OF EMBODIMENTS

The present disclosure relates to compositions comprising a nucleotide sequence. In some embodiments, the nucleotide sequence comprises: (i) an RNA-binding domain from about 5 to about 30 nucleotides complementary to a region of a mammalian double homeobox 4 (DUX4); and (ii) at least one locked nucleic acid (LNA) domain comprising from about 1 to about 5 nucleotides, or a salt thereof.

The present disclosure also relates to a composition comprising a nucleotide sequence from about 8 to about 120 nucleotides. In some embodiments, the nucleotide sequence is complementary to at least about 8 contiguous nucleotides from position 675 to position 688 of exon 1 of a human DUX4, or a salt thereof. In some embodiments, the nucleotide sequence is complementary to at least about 8 contiguous nucleotides from position 182 to position 197 of exon 3 of a human DUX4, or a salt thereof. In some embodiments, the nucleotide sequence is complementary to at least about 8 contiguous nucleotides from position 98 to position 116 of exon 3 of a human DUX4, or a salt thereof. In some embodiments, the nucleotide sequence comprises a central DNA gap domain flanked by a first LNA domain at a 5' end of the nucleotide sequence and a second LNA domain on a 3' end of the nucleotide sequence. In some embodiments, the nucleotide sequence comprises one or a plurality of nucleotide sequences chosen from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 14, SEQ ID NO: 15, SEQ ID NO: 16, SEQ ID NO: 17, SEQ ID NO: 18, SEQ ID NO: 19, and SEQ ID NO: 20 or combination thereof. In some embodiments, the composition comprises at least 2 nucleic acid molecules, each nucleic acid molecule comprising one or a plurality of nucleotide sequences chosen from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 14, SEQ ID NO: 15, SEQ ID NO: 16, SEQ ID NO: 17, SEQ ID NO: 18, SEQ ID NO: 19, and SEQ ID NO: 20 or combination thereof.

The present disclosure also relates to a pharmaceutical composition. In some embodiments, the pharmaceutical composition comprises: (i) a therapeutically effective amount of any composition described herein; and (ii) a pharmaceutically acceptable carrier.

The present disclosure also relates to a method of treating a dystrophin-related disorder. In some embodiments, the method comprises administering to a subject in need thereof a therapeutically effective amount of one or a combination of any composition described herein, and/or any pharmaceutical composition described herein.

The present disclosure also relates to a method of modulating or inhibiting expression of DUX4 in a subject. In some embodiments, the method comprises administering to the subject a therapeutically effective amount of one or a combination of any composition described herein, and/or any pharmaceutical composition described herein.

The present disclosure also relates to a method of targeting a DUX4 mRNA in a cell. In some embodiments, the cell is a muscle cell. In some embodiments, the method comprises contacting one or a combination of any composition described herein, and/or any pharmaceutical composition described herein, with the cell. In some embodiments, the cell is a muscle cell. In some embodiments, the method of targeting a DUX4 mRNA comprises contacting any one or plurality of the nucleotide sequences disclosed herein with a cell expressing DUX4 mRNA at a concentration sufficient and for a time sufficient to hybridize the one or plurality of nuelcotide sequences to the DUX4 mRNA. In some embodiments, the step of contecting is preceded by administering the one or plurality of nucleotide sequences In some embodiments, the one or plurality of the nucleotide sequences disclosed herein comprises a marker or tag that is capable of detection upon exposure to a stimulus, such as a particular wavelength of light, magnetic field or an ezyme with a known reaction product. In some embodiments, the method of targeting a DUX4 mRNA in a cell further comprises exposing the one or plurality of nucleotide sequences comprising a marker or tag to a stimulus such that the marker or tag is visible after administration of an effective amount of the one or plurality of nucleotide sequences.

BRIEF DESCRIPTION OF THE DRAWINGS

FIG. 2A: Contraction of D4Z4 macrosatellite repeats in FSHD1 relaxes the chromatin structure, causing an induction of DUX4 expression from the distal-most repeat unit (indicated by dark gray box). Polyadenylated DUX4 transcripts expressed from the 4qA allele (indicated by light gray box) are stable and translate into a toxic transcription factor, DUX4. Modified from Jones et al., 2014. FIG. 2B: Schematic representation of the distal-most D4Z4 repeat, the pLAM region or 4qA allele or permissive allele, and the distally located exons. The DUX4 ORF is within the first exon. Two poly-A signals were reported in exons 3 and 7. The pLAM region is associated with the 4qA allele. FIG. 2C: Two fl-DUX4 mRNA isoforms. fl-DUX4 mRNA detected in FSHD myoblasts contain the full ORF in exon 1 and end in exon 3. These mRNAs were derived from chromosome 4. fl-DUX4 was also detected in germline tissue and contain the full ORF in exon 1, but have 4 addition exons, 4, 5, 6 and 7. s-DUX4 was detected in healthy unaffected muscles (patients without the FSHD phenotype), in somatic tissues and in FSHD affected muscles. Modified from Vanderplanck et al., 2011.

FIG. 9A is a picture of semi-quantitative RT-PCR analysis depicting the change in DUX4 band intensities, after transfection with LNA gapmers 1, 2 or 3 (100 nM) at Day 4 after differentiation with 24-hour LNA gapmer incubation. FIG. 9B is a graph showing the relative quantification of the suppression of DUX4 following normalization to GAPDH, compared to non-treated cells (15ABic). Experiments were repeated two times in triplicate. Error bars represent standard error. **$p<0.005$ versus non-treated (15ABic) under one-way ANOVA and Dunnett's multiple comparisons test. RT-PCR for GAPDH mRNA expression was used as an internal control. Human testis total RNA was used as positive control. The healthy (15VBic) sample represents control myoblasts derived from an unaffected individual confirmed without the FSHD genotype.

FIG. 10A: Nuclear extracts were prepared 24 hours after transfection. 9 µg were separated by electrophoresis. TBP nuclear loading control was used for normalization, however TBP protein levels were undetectable in 15ABic or 15VBic samples and therefore all samples were normalized to Cofilin. Testis tissue lysate (Abcam, CA) was used as a positive control. FIG. 10B: Whole cell extracts were prepared 24 hours after transfection. 18 μg were separated by electrophoresis.

FIG. 11A: Semi-quantitative RT-PCR analysis depicting the change in DUX4 band intensities, after transfection with LNA gapmers 1*, 2*, 3*, 4, 5, 6 or 7 (100 nM) at Day 4 after differentiation with 24-hour LNA gapmer incubation. FIG. 11B: Relative quantification of the suppression of DUX4 following normalization to GAPDH, compared to testis sample. Experiments were repeated two times in triplicate. Error bars represent standard deviation. *$p<0.05$ versus non-treated (15ABic) under one-way ANOVA and Dunnett's multiple comparisons test. **$p<0.005$ versus non-treated (15ABic) under one-way ANOVA and Dunnett's multiple comparisons test. RT-PCR for GAPDH mRNA expression was used as an internal control. Human testis total RNA was used as a positive control. The healthy (15VBic) sample represents control myoblasts derived from an unaffected individual confirmed without the FSHD genotype.

DETAILED DESCRIPTION OF EMBODIMENTS

Figure 1:
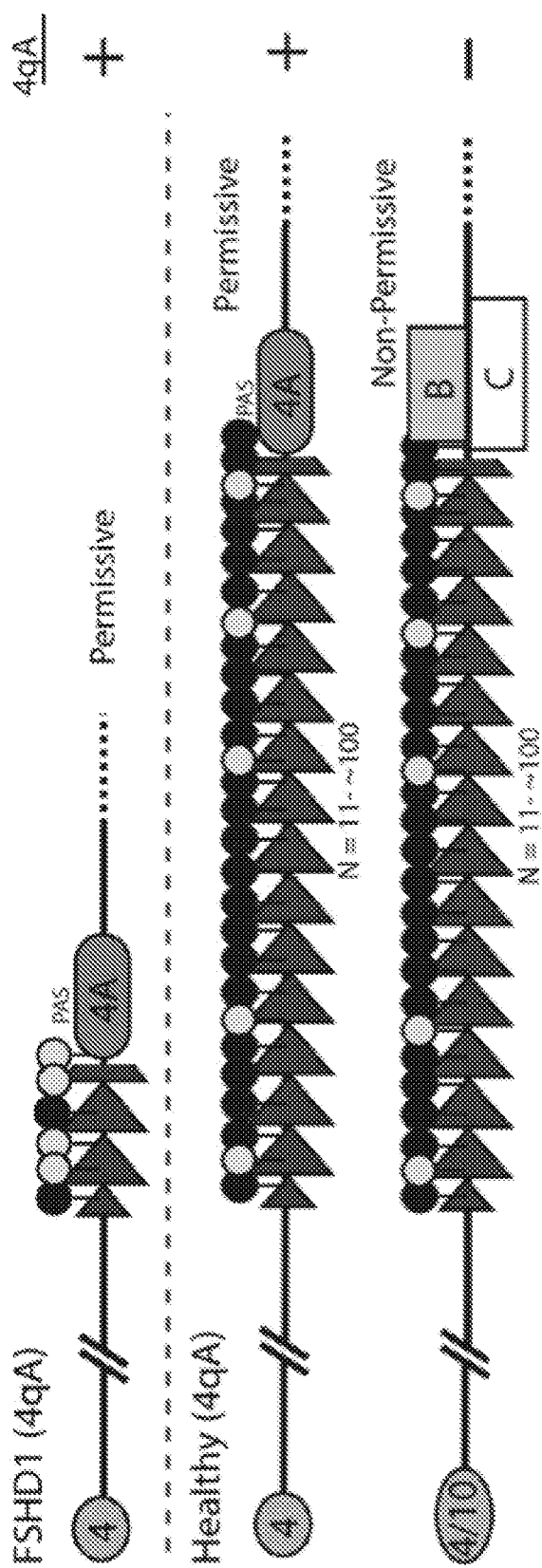
FIG. 1 shows a schematic overview of epigenetic and genetic changes in FSHD compared to healthy individuals. In healthy individuals, their polymorphic macrosatellite repeat consists of more than 10 D4Z4 repeat units. In FSHD1, there is a contraction of the D4Z4 allele, resulting in between 1 and 10 D4Z4 repeat units, whereas in FSHD2 the D4Z4 allele is contraction-independent. There are two main allelic variants in the subtelomere distal to the repeat arrays, known as 4qA and 4qB. Both FSHD1 and FSHD2 are exclusively linked to the 4qA subtelomere allelic variants. Both FSHD1 and FSHD2 are associated with epigenetic hypomethylation of the D4Z4 array. Yellow circles represent hypomethylated CpGs. Black circles represent hypermethylated CpGs. Abbreviation PAS, DUX4 polyadenylation signal. Modified from Jones et al., 2014.
Figure 2A:
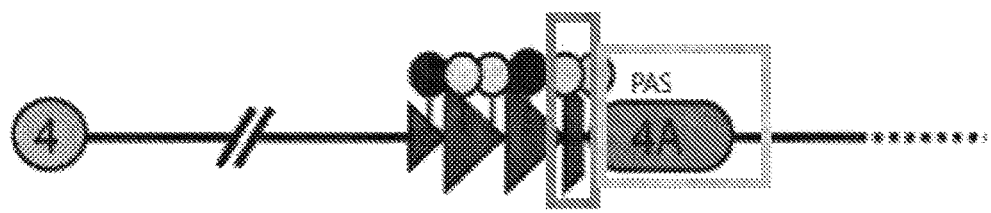
FIG. 2A-FIG. 2C show DUX4 mRNA variants.
Figure 2B:
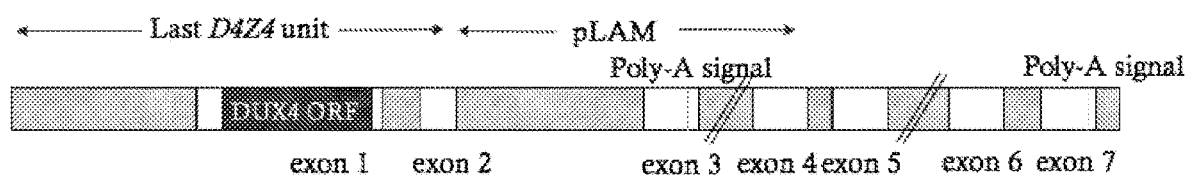
Figure 2C:
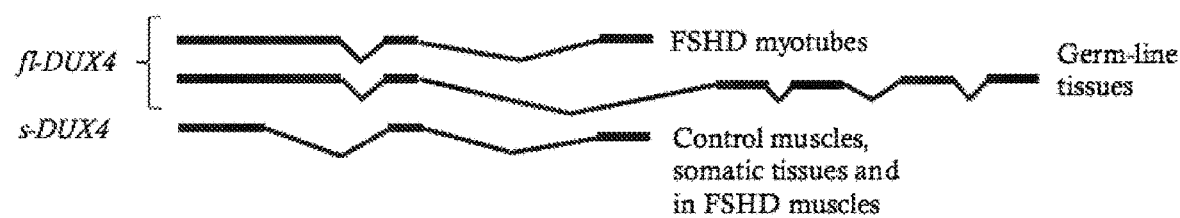
Figure 3:
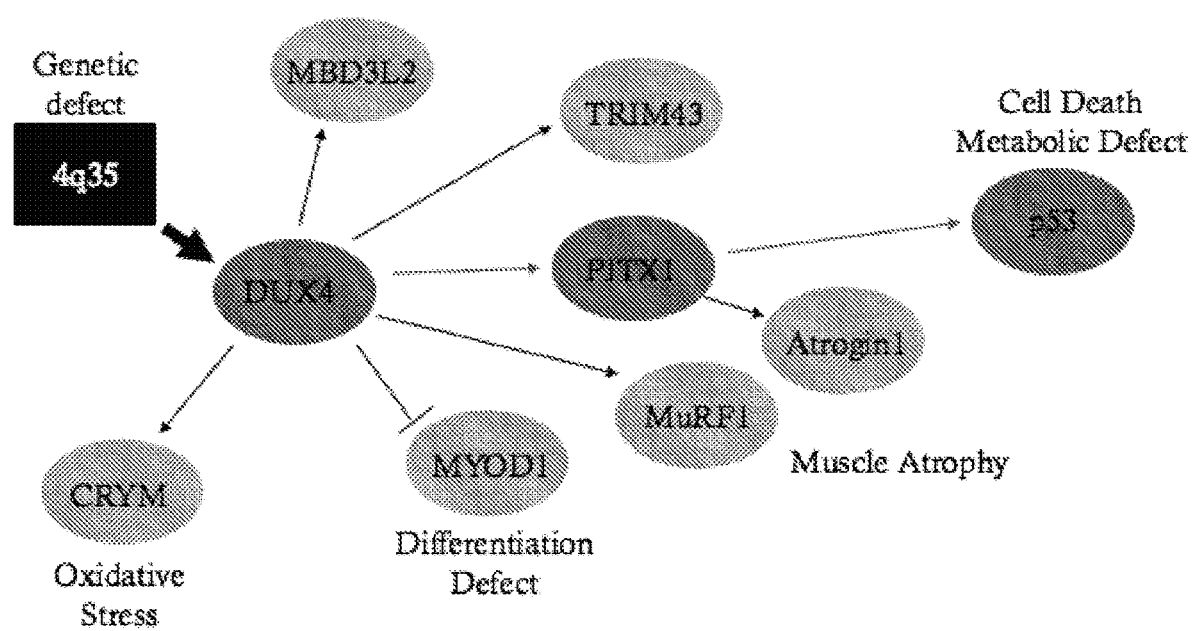
FIG. 3 shows transcriptional cascades downstream of DUX4 in FSHD. Mapped within the D4Z4 element at 4q35 is a transcription factor DUX4. DUX4 directly targets PITX1, a gene up-regulated in FSHD compared to 11 neuromuscular disorders. PITX1 up-regulation induces E3 ubiquitin ligases (Atrogin1 and MuRF1), which are associated with atrophy in adult skeletal muscles. Among the PITX1 target genes is p53 which has shown to have a role in apoptosis in FSHD. DUX4 inhibits MYOD1 causing inhibition of the MYOD1 target genes in FSHD. DUX4 also induces the expression of the mu-crystallin (CRYM) gene. Other robust markers for DUX4 expression are MBD3L2 and TRIM43 which are up-regulated in FSHD fetal and adult biopsies. Legend: Activate: →Inhibit: ⊣. Figure adapted from Vanderplanck et al., 2011.
Figure 4:
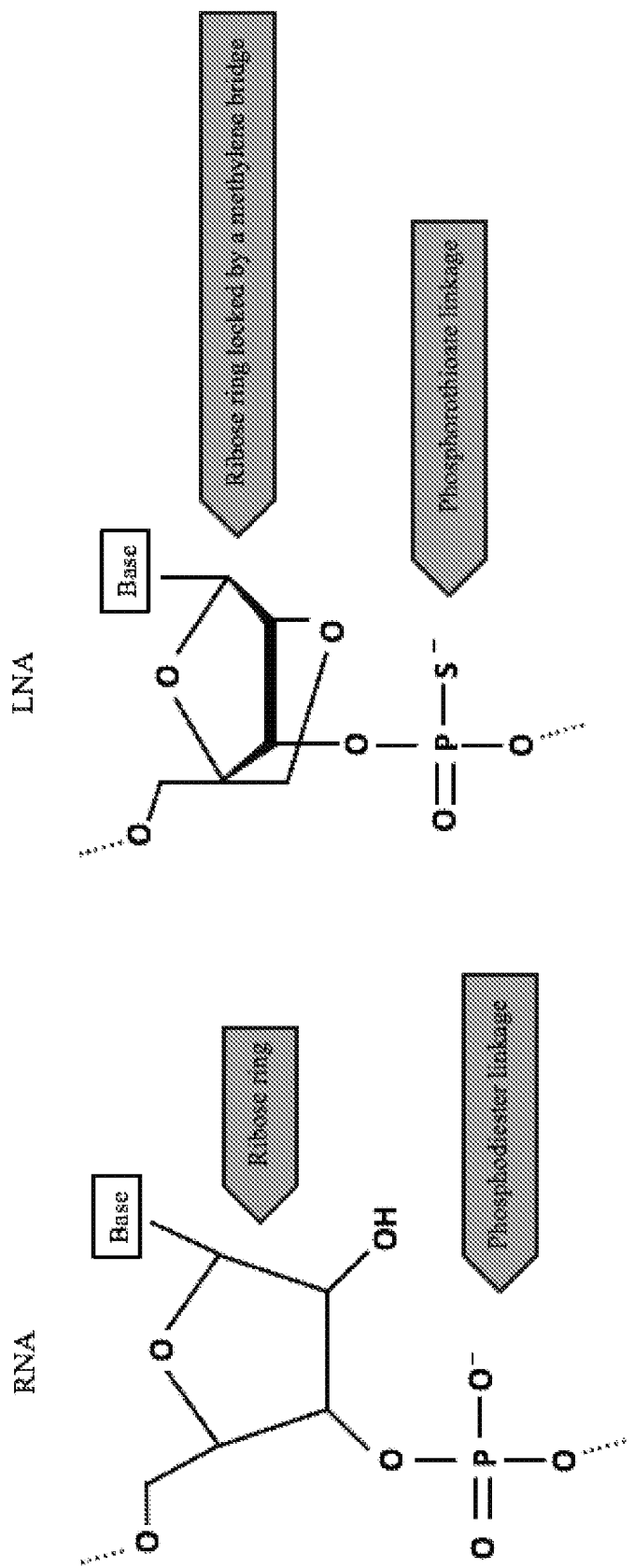
FIG. 4 shows the molecular structure of LNA antisense oligonucleotide chemistry compared to RNA. Locked nucleic acid (LNA) structure contains a furanose ring of the ribose sugar. The key difference between DNA and LNA is the introduction of a 2'O-4'C-methylene linkage, which imposes a locked RNA-mimicking conformation.
Figure 5:
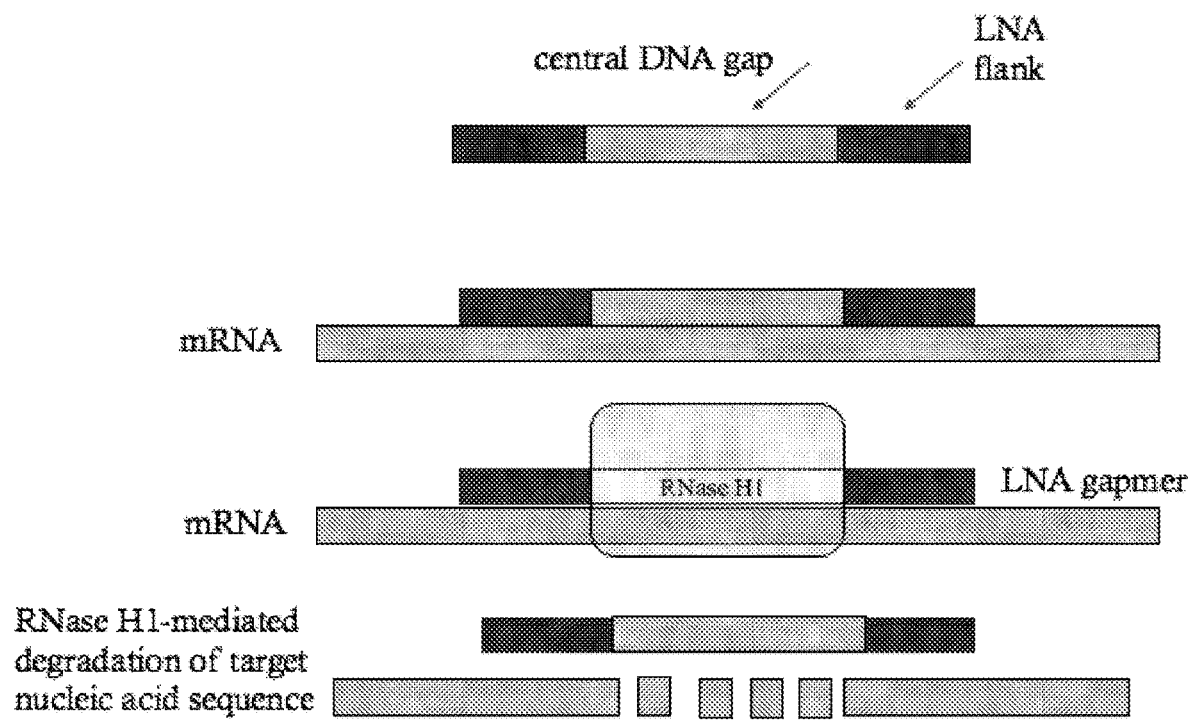
FIG. 5 shows the mechanism of antisense silencing via RNase H1-mediated degradation RNase H1-mediated degradation of target mRNA can occur via LNA gapmers. LNA gapmers are composed of a central DNA gap and flanked by LNA monomers at the 5' and 3'-ends. The central DNA gap works through RNase H1 activity, whereas the LNA flanks are used to target binding affinity to the mRNA sequence. Figure adapted from Lee and Yokota, 2014.
Figure 6:
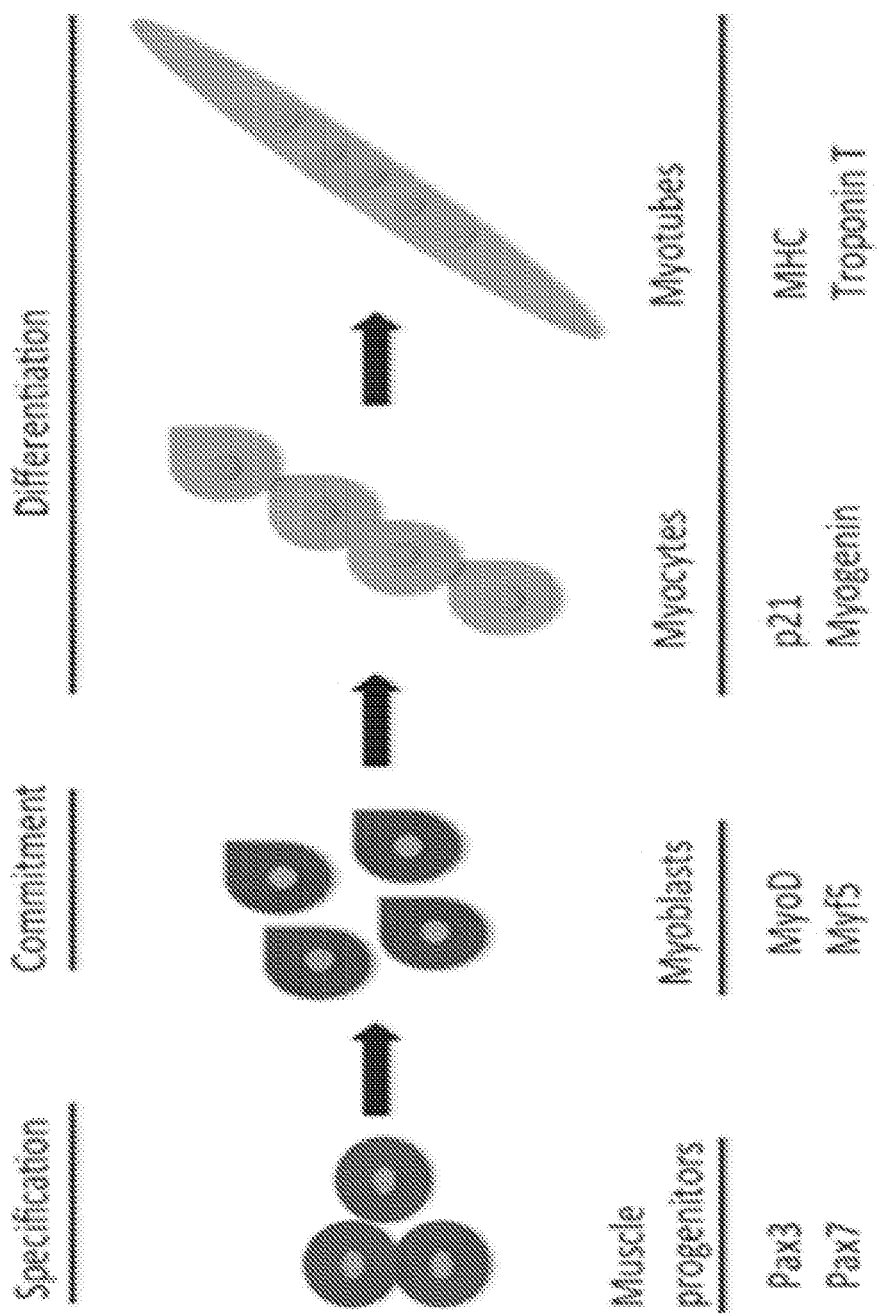
FIG. 6 shows a schematic representation of skeletal muscle differentiation. Muscle progenitors cells positive for Pax3/Pax7 initiate myogenic lineage commitment. Cells expressing both MyoD and Myf5 undergo expansion and proliferation to become myoblasts. Upon the initiation of differentiation, myoblasts exit the cell cycle and myocytes begin to express two differentiation markers; p21 and Myogenin. Terminally differentiated multinucleated myotubes positively express myosin heavy chain (MHC) and Troponin T. Taken from Bharathy et al., 2013.

The terminology used herein is for the purpose of describing particular embodiments only and is not intended to be limiting. Unless specifically defined herein, all terms used herein have the same meaning as they would to one skilled in the art of the present invention. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The present disclosure relates to compositions comprising a nucleotide sequence. In some embodiments, the nucleotide sequence comprises (i) an RNA-binding domain from about 5 to about 30 nucleotides complementary to a region of a mammalian double homeobox 4 (DUX4); and (ii) at least one locked nucleic acid (LNA) domain comprising from about 1 to about 5 nucleotides, or a salt thereof.

The term "about" as used herein when referring to a measurable value such as an amount, a temporal duration, and the like, is meant to encompass variations of ±20%, ±10%, ±5%, ±1%, ±0.9%, ±0.8%, ±0.7%, ±0.6%, ±0.5%, ±0.4%, ±0.3%, ±0.2% or ±0.1% from the specified value, as such variations are appropriate to perform the disclosed methods.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, the term "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, "either," "one of," "only one of," or "exactly one of" "Consisting essentially of," when used in the claims, shall have its ordinary meaning as used in the field of patent law.

As used herein, "activity" in the context of LNA gapmer activity refers to the ability of a nucleic acid to bind to a target domain of a nucleic acid sequence and/or bind a cellular receptor or binding partner to a degree and for a period of time sufficient to allow entry of the nucleic acid sequence into a target cell (a cell expressing a mRNA with a target domain), such as a muscle cell. In some embodiments, the activity refers to the ability of a nucleic acid to bind to a target domain of a nucleic acid sequence. Such activity can be measured in a variety of ways as known in the art. For example, mRNA or protein expression, activity, or level of a gene sequence can be measured, and targeting the gene sequence can be assayed for their ability to reduce the expression, activity, or level of the gene. For example, a cell can be transfected with, transformed with, or contacted with a nucleotide sequence disclosed herein. The activity can be measured by monitoring the expression of the target nucleic acid sequence and comparing expression to a cell not transfected, transformed or contacted with disclosed nucleic acid sequences. In some embodiments, the target sequence is a mammalian double homeobox 4 (DUX4) or any region therein. In some embodiments, LNA gapmer activity can be measured by DUX4 mRNA or protein expression.

The term "analog" as used herein refers to compounds that are similar but not identical in chemical formula and share the same or substantially similar function of the compound with the similar chemical formula. In some embodiments, the analog is a mutant, variant or modified sequence as compared to the non-modified or wild-type sequence upon which it is based. In some embodiments, compositions of the disclosure include modifications or analogs that are at least about 70%, about 75%, about 80%, about 85%, about 90% about 91%, about 92%, about 93%, about 94%, about 95%, about 96%, about 97%, about 98% or about 99% homology to any of the disclosed nucleic acids disclosed herein. In some embodiments the analog is a functional fragment of any of the disclosed nucleic acid sequences. In some embodiments, the analog is a salt of any of the disclosed nucleic acid sequences. In such embodiments, the analog may retain about 99%, 98%, 97%, 96%, 95%, 94%, 93%, 92%, 91%, 90%, 85%, 80%, 75%, 70% or less biological activity as compared to the natural or wild-type sequences upon which it is based.

"Nucleobase" means a heterocyclic moiety capable of non-covalently pairing with another nucleobase.

"Nucleoside" means a nucleobase linked to a sugar moiety.

"Nucleotide" means a nucleoside having a phosphate group covalently linked to the sugar portion of a nucleoside. In some embodiments, the nucleotide is characterized as being modified if the 3' phosphate group is covalently linked to a contiguous nucleotide by any linkage other than a phosphodiester bond.

"Oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

"Internucleoside linkage" means a covalent linkage between adjacent nucleosides of an oligonucleotide.

As used herein, a "gapmer" is a region of a natural or nonnatural nucleotide sequence having one or more nucleosides that can bind to a target oligonucleotide. In some embodiments, the gapmer comprises a domain comprising one or a plurality of modified or unmodified deoxynucleotides. In some embodiments, the gapmer comprises a domain comprising one or a plurality of modified or unmodified ribonucleotides. In some embodiments, the gapmer hybridization to a target sequence induces cleavage of at least a portion of the target oligonucleotide by Rnase H. In some embodiments, the gapmer is a chimeric antisense compound. In some embodiments, the gapmer is an LNA gapmer comprising a DNA gapmer domain and an LNA domain. In some embodiments, the DNA gapmer domain is flanked by two LNA domains. In some embodiments, the gapmer has an internal region having a plurality of nucleosides that support RNase H cleavage, positioned between external regions having one or more nucleosides. In some embodiments, the nucleosides comprising the internal region are chemically distinct from the nucleoside or nucleosides comprising the external regions. In certain embodiments, the target oligonucleotide comprises from about 5 to about 200, from about 5 to about 50, from about 10 to about 100, from about 10 to about 50, from about 10 to about 25, from about 15 to about 100, from about 15 to about 50, from about 5 to about 25, or from about 15 to about 25 nucleotides. In some embodiments, the gapmer comprises a series of contiguous or noncontiguous deoxyribonucleic acid and ribonucleic acid.

The disclosure relates to a nucleic acid sequence disclosed herein also comprising one or a plurality of modified nucleotides. In some embodiments, the compositions of the disclosure comprise a nucleic acid sequence disclosed herein comprising one or a plurality of modified oligonucleotides. In some embodiments, the composition comprises any one, two, three or more nucleic acid sequences disclosed herein comprising a modified oligonucleotide consisting of a number of linked nucleosides. Thus, the compound or compounds may include additional substituents or conjugates.

"Modified oligonucleotide" means an oligonucleotide having one or more modifications relative to a naturally occurring terminus, sugar, nucleobase, and/or internucleoside linkage. A modified oligonucleotide may comprise unmodified nucleosides at one or a plurality of any of the positions of the disclosed nucleic acids.

"Single-stranded modified oligonucleotide" means a modified oligonucleotide which is not hybridized to a complementary strand. In some embodiments, the compositions of the disclosure relate to a nucleic acid molecule that is a single-stranded modified oligonucleotide comprising any one or more domains disclosed herein.

The nucleic acid sequences of the disclosure can comprise one or more modified nucleosides. The terms "modified nucleoside" mean a nucleoside having any change from a naturally occurring nucleoside. A modified nucleoside may have a modified sugar and an unmodified nucleobase. A modified nucleoside may have a modified sugar and a modified nucleobase. A modified nucleoside may have a natural sugar and a modified nucleobase. In certain embodiments, a modified nucleoside is a bicyclic nucleoside. In certain embodiments, a modified nucleoside is a non-bicyclic nucleoside.

The term "nucleic acid" is defined as a molecule formed by covalent linkage of two or more nucleotides. The terms "nucleic acid," "polynucleotide" and "nucleotide sequence" are used interchangeably herein. The term "nucleic acid analogue" refers to a non-natural nucleic acid binding compound. Nucleotide analogues and nucleic acid analogues are described in e.g. Freier & Altmann (Nucl. Acid Res., 1997, 25, 4429-4443) and Uhlmann (Curr. Opinion in Drug & Development (2000, 3(2): 293-213).

The term "locked nucleic acid" or "LNA" refers to a modified nucleotide, more specifically a nucleotide containing one bicyclic nucleoside analogue, also referred to as an LNA monomer, or an oligonucleotide containing one or more bicyclic nucleoside analogues. In LNA, a 2'-O-4'-C-methylene linkage locks the furanose ring, making up the ribose sugar, in a C3'-end conformation which mimics the RNA structure. In some embodiments, LNA domains are from about 1 to about 5 nucleotides in length. In some embodiments, LNA domains are an oligonucleotide of about 3 nucleotides in length.

An "LNA gapmer," as used herein refers to an oligonucleotide composed of LNA segments flanking a central DNA gap that can be phosphorothionated. In some embodiments, the central DNA gap is about 6 or more nucleotides, for example, from about 7 to about 10 nucleotides. In some embodiments, the central DNA gap is 11 or more nucleotides in length. In some embodiments, the LNA gapmer is from about 8 to about 120 nucleotides. In some embodiments, the LNA gapmer is from about 10 to about 100 nucleotides. In some embodiments, the LNA gapmer is from about 10 to about 80 nucleotides. In some embodiments, the LNA gapmer is from about 10 to about 60 nucleotides. In some embodiments, the LNA gapmer is from about 10 to about 40 nucleotides. In some embodiments, the LNA gapmer is from about 10 to about 30 nucleotides. In some embodiments, the LNA gapmer is from about 10 to about 25 nucleotides. In some embodiments, the LNA gapmer is from about 10 to about 20 nucleotides. In some embodiments, the LNA gapmer is from about 8 to about 30 nucleotides. In some embodiments, the LNA gapmer is from about 8 to about 20 nucleotides. In some embodiments, the LNA gapmer is from about 14 to about 16 nucleotides.

The terms "biophysically effective amount" refers to an amount of nucleic acid in a system under one or a plurality of physiological conditions (such as temperature, pH, exposure to percent oxygen, etc.) sufficient for a nucleic acid sequence disclosed herein or an analog thereof to associate with a DNA gap domain target or a microRNA target. In some embodiments, the nucleic acid sequence of the disclosure is in a biophysically effective amount.

It should be understood that some nucleic acid sequences (such as LNA gapmer targets) or any analog thereof described herein are intended to include nucleic acid sequences comprising polynuclotides bearing one or more insertions, deletions, or substitutions, or any combination thereof, of nucleic acid residues as well as modifications other than insertions, deletions, or substitutions of nucleic acid residues.

In some embodiments, in the presence of one or a plurality of proteins (or functional fragments thereof) and a target sequence, the one or plurality of proteins and the nucleic acid element forms a biologically active complex and/or can be enzymatically active on a target sequence.

The term "target nucleic acid", as used herein refers to the DNA or RNA sequence encoding the mammalian target polypeptide (target for down-regulation). In one embodiment, for example when used in research or diagnostics the "target nucleic acid" may be a cDNA or a synthetic oligonucleotide derived from the above DNA or RNA nucleic acid targets. The oligomer according to the invention is preferably capable of hybridising to the target nucleic acid. In some embodiments, the target nucleic acid is a mammalian DUX4 or any nucleotide or nucleotide sequence thereof.

The terms "target domain" refers to a amino acid sequence or nucleic acid element or domain within a nucleic acid sequence (or polynucleotide sequence) that binds to an LNA gapmer either covalently or non-covalently when the LNA gapmer is in contact with the target domain in a biophysically effective amount. In some embodiments, the target domain consists of no more than about 5, 10, 15, 20, 25, 30, 35, 40, 45, 50, 60, 70, 80, 90, 100, 110, 120, 130, 140, 150, 160, 170, 180, 190, 200, 210, 220, 230, 240, 250 or more nucleotides in length. In some embodiments, the target domain is expressed by a cell, such as a muscle cell. In some embodiments, the target domain is expressed by a human muscle cell.

In some embodiments, a target domain or sequence is located in the nucleus or cytoplasm of a cell. In some embodiments, the target sequence may be within an organelle of a eukaryotic cell, for example, mitochondrion or chloroplast. In some embodiments, the compostions of the disclosure comprises one or a plurality of nucleic acid sequences comprising at least one LNA gapmer that recognizes one or a plurality of target domains, wherein the target domain or domains are expressed on the surface of a cell.

One or a plurality of vectors may also be components in any system or composition provided herein. In some embodiments, the disclosure comprises a composition comprising a vector comprising any nucleic acid sequence disclosed herein optionally comprising a regulatory sequence that is operably connected to the nucleic acid sequence disclosed herein such that the nucleic acid sequence is expressible under conditions sufficient to induce expression of the nucleic acid. In some embodiments, the vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors.

When multiple, different nucleic acid sequences disclosed herein are used together, a single expression construct may be used to target an LNA gapmer to multiple, different, corresponding target domains sequences within and/or on a cell. In some embodiments, the disclosure relates to a composition with one or a plurality of vectors expressing a first, second, third, and/or fourth or more nucleic acid sequence disclosed herein. For example, a single vector may comprise about or more than about 1, 2, 3, 4, 5, 6, 7, 8, 9, 10, 15, 20, or more nucleic acid sequences disclosed herein. In some embodiments, about or more than about 1, 2, 3, 4, 5, 6, 7, 8, 9, 10, or more such nucleic acid-sequence-containing vectors may be provided, and optionally delivered to a cell. The disclosure relates to any composition comprising any of the aforementioned elements and one or more nucleic acid molecules (for instance a first and second) each comprising one or more nucleic acid sequences disclosed herein.

As used herein, "expression" refers to the process by which a polynucleotide is transcribed from a DNA template (such as into an mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "functional fragment" means any portion of a nucleic acid sequence from which the respective full-length nucleic acid relates that is of a sufficient length and has a sufficient structure to confer a biological affect that is identical, at least similar to or substantially similar to the full-length polypeptide or nucleic acid upon which the fragment is based. In some embodiments, a functional fragment is a portion of a full-length sequence that still biologically functional as compared to the full-length or wild-type sequence. In some embodiments, the functional fragment may have a reduced biological activity, about equivalent biological activity, or an enhanced biological activity as compared to the wild-type or full-length nucleic acid sequence upon which the fragment is based. In some embodiments, the functional fragment is derived from the sequence of an organism, such as a human. In such embodiments, the functional fragment may retain about 99%, 98%, 97%, 96%, 95%, 94%, 93%, 92%, 91%, or 90% sequence activity to the full-length sequence upon which the sequence is derived. In some embodiments, the functional fragment is about 99%, 98%, 97%, 96%, 95%, 90%, 85%, 80%, 75%, 70%, 65%, or 60% sequence homology to the full-length nucleic acid sequence upon which the sequence is derived. In such embodiments, the functional fragment may retain about 99%, 98%, 97%, 96%, 95%, 94%, 93%, 92%, 91%, 90%, 85%, 80%, 75%, 70% or less biological activity as compared to the full-length sequences upon which it is based. In some embodiments, the composition provided comprises one, two, three or more nucleic acid sequences or salts thereof that is a functional fragment retaining 99%, 98%, 97%, 96%, 95%, 94%, 93%, 92%, 91%, 90%, 85%, 80%, 75%, or 70% sequence identity to any sequence identified in Table 4. In some embodiments, the composition provided comprises a therapeutically effective amount of a nucleic acid molecule or multiple nucleic acid molecules or salts thereof that comprise one, two, three or more nucleic acid sequences or salts thereof that is a variant having 99%, 98%, 97%, 96%, 95%, 94%, 93%, 92%, 91%, 90%, 85%, 80%, 75%, or 70% sequence identity to any sequences identified in Table 4. In the case of LNA gapmers, such embodiments comprise a composition comprising a therapeutically effective amount of a nucleic acid molecule or multiple nucleic acid molecules or salts thereof, wherein each nucleic acid molecule or salt thereof comprises a first and a second nucleic acid sequences that comprise at least one gapmer domain that is a variant having 99%, 98%, 97%, 96%, 95%, 94%, 93%, 92%, 91%, 90%, 85%, 80%, 75%, or 70% sequence identity to any sequence identified in Table 4 or any sequence capable of binding the target domain identified herein.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. In some embodiments, association or binding of a disclosed nucleic acid sequence is hybridizing with a nucleic acid sequence or molecule within a target cell.

The present disclosure also relates to isotopically-enriched compounds, which are structurally similar to the nucleic acid sequences disclosed herein, but for the fact that one or more atoms of the nucleic acid sequence are replaced by an atom having an atomic mass or mass number different from the atomic mass or mass number usually found in nature. Examples of isotopes that can be incorporated into compounds of the disclosure include isotopes of hydrogen, carbon, nitrogen, oxygen, phosphorous, fluorine and chlorine, such as $^{2}H$, $^{3}H$, $^{13}C$, $^{14}C$, $^{15}N$, $^{16}O$, $^{17}O$, $^{31}P$, $^{32}P$, $^{35}S$, $^{18}F$, and $^{36}Cl$. Nucleic acids of the present disclosures that contain the aforementioned isotopes and/or other isotopes of other atoms are within the scope of this disclosure. Certain isotopically-labelled compounds of the present disclosure, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detection. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically enriched compounds of this disclosure can generally be prepared by substituting a readily available isotopically labeled reagent for a non-isotopically enriched reagent. In some embodiments, the compositions of the disclosure comprise one or more nucleic acid sequences disclosed herein comprising an LNA domain and a DNA gap domain with one or more atoms replaced with a radioisotope. In some embodiments, such radioactive nucleic acid sequences may be a component in a pharmaceutical composition that delivers a radioisotope to a cell after administration to a subject in need of the treatment. In some embodiments, the radioactive nucleic acid sequence can be used as a targeted imaging agent whereupon, after administration to a subject, one or more imagining techniques may be used to detect where within a subject one or a plurality of cells may exist within the subject. Such imaging techniques include PET scanning or CT scanning.

The disclosure relates to nucleic acids disclosed herein unsolvated forms as well as solvated forms, including hydrated forms. The compounds of the disclosure also are capable of forming both pharmaceutically acceptable salts, including but not limited to acid addition and/or base addition salts. Furthermore, compounds of the present disclosure may exist in various solid states including an amorphous form (noncrystalline form), and in the form of clathrates, prodrugs, polymorphs, bio-hydrolyzable esters, racemic mixtures, non-racemic mixtures, or as purified stereoisomers including, but not limited to, optically pure enantiomers and diastereomers. In general, all of these forms can be used as an alternative form to the free base or free acid forms of the compounds, as described above and are intended to be encompassed within the scope of the present disclosure.

A "polymorph" refers to solid crystalline forms of the one or more nucleic acid sequences disclosed herein. In some embodiments, one or more nucleic acids disclosed herein are in a polymorph form. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Different physical properties of polymorphs can affect their processing.

The nucleotide sequences of the present disclosure can be administered, inter alia, as pharmaceutically acceptable salts, esters, or amides. The term "salts" refers to inorganic and organic salts of compounds of the present disclosure. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977), which discloses salt forms of nucleic acids and which is incorporated by reference in its entirety.

The terms "polynucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after synthesis or polymerization, such as by conjugation with a labeling component.

The oligonucleotides of the disclosure also include those nucleic acid sequences disclosed herein that comprise nucleosides connected by charged linkages, and/or whose sequences are divided into at least two subsequences. In some embodiments, a first, second, and third subsequence or domains include a DNA gap domain and a locked nucleic acid (LNA) domain. In some embodiments the nucleic acid sequence comprises two LNA domains contiguously or non-contiguously flanking a central DNA gap domain.

In the context of this disclosure, the term "oligonucleotide" also refers to a plurality of nucleotides joined together in a specific sequence from naturally and non-naturally occurring nucleobases. Nucleobases of the disclosure are joined through a sugar moiety via phosphorus linkages, and may include any one or combination of adenine, guanine, cytosine, uracil, thymine, xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, other aza and deaza thymidines, other aza and deaza cytosines, other aza and deaza adenines, other aza and deaza guanines, 5-trifluoromethyl uracil and 5-trifluoro cytosine. The sugar moiety may be deoxyribose or ribose. The sugar moiety may be a modified deoxyribose or ribose with one or more modifications on the $C_1$, $C_2$, $C_3$, $C_4$, and/or $C_5$ carbons. The oligonucleotides of the disclosure may also comprise modified nucleobases or nucleobases having other modifications consistent with the spirit of this disclosure, and in particular modifications that increase their nuclease resistance in order to facilitate their use as therapeutic, diagnostic or research reagents.

The terms "polypeptide", "peptide" and "protein" are used interchangeably herein to refer to polymers of amino acids of any length. The polymer may be linear or branched, it may comprise modified amino acids, and it may be interrupted by non-natural amino acids or chemical groups that are not amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, "more than one" or "two or more" 2, 3, 4, 5, 6, 7, 8, 9, or 10 or more where "more" may be an positive integer above 10 that corresponding to the length of nucleotides in the nucleotide sequences. In some embodiments, "more than one" means 2, 3, 4, or 5 of the amino acids or nucleic acids or mutations described herein. In some embodiments, "more than one" means 2, 3, or 4 of the amino acids or nucleic acids or mutations described herein. In some embodiments, "more than one" means 2 or 3 of the amino acids or nucleic acids or mutations described herein. In some embodiments, "more than one" means 2 of the amino acids or nucleic acids or mutations described herein.

The terms "therapeutically effective amount" mean a quantity sufficient to achieve a desired therapeutic effect, for example, an amount which results in the prevention or amelioration of or a decrease in the symptoms associated with a disease that is being treated. The amount of composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The regimen of administration can affect what constitutes an effective amount. The compound of the disclosure can be administered to the subject either prior to or after the onset of disease or disorder. Further, several divided dosages, as well as staggered dosages, can be administered daily or sequentially, or the dose can be continuously infused, or can be a bolus injection. Further, the dosages of the compound(s) of the disclosure can be proportionally increased or decreased as indicated by the exigencies of the therapeutic. Typically, an effective amount of the compounds of the present disclosure, sufficient for achieving a therapeutic or prophylactic effect, range from about 0.000001 mg per kilogram body weight per day to about 10,000 mg per kilogram body weight per day. Preferably, the dosage ranges are from about 0.0001 mg per kilogram body weight per day to about 100 mg per kilogram body weight per day. A therapeutically effective amount of a pharmaceutical composition comprising any one or a plurality of any of the nucleic acid sequences disclosed herein can also be administered in combination with two, three, four or more nucleic acid sequences disclosed herein, or with one or more additional therapeutic compounds. Those skilled in the art will recognize and determine a therapeutically effective amount of any of the nucleic acid sequences disclosed herein whether calculated when administered alone or part of a therapeutic regimen that includes one or more other therapeutic agents and/or one or more other therapeutic treatments or interventions. Generally, therapeutically effective amount refers to an amount of a nucleic acid sequence that alone or in combination with one or a plurality of other therapeutic compounds causes a transfection of the nucleic acid sequence into a target cell (such as a muscle cell) and/or hybridization of the one or more miRNA domains within the nucleic acid sequences sufficient reduce or inhibit expression of a mRNA sequence with the cell, thereby ameliorating symptoms, or reversing, preventing or reducing the rate of progress of disease, or extend life span of a subject when administered alone or in combination with other therapeutic agents or treatments as compared to the symptoms, rate of progress of disease, or life span of an individual not receiving a therapeutically effective amount the one or plurality of nucleic cells disclosed herein.

The terms "treating" and "to treat", mean to alleviate signs and/or symptoms, eliminate the causation either on a temporary or permanent basis, or to prevent or slow the appearance of signs and symptoms. The term "treatment" includes alleviation, elimination of causation (temporary or permanent) of, or prevention of signs and/or symptoms and disorders associated with any condition, such as a dystrophin-related disorder, such as a muscular dystrophy. The treatment may be a pre-treatment (as a preventative treatment) and/or treatment at the onset of signs and/or symptoms.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C) including the radioisotopes of Table 2. All isotopic variations of the compounds of the present disclosure, whether radioactive or not, are encompassed within the scope of the present disclosure.

The symbol "-" denotes the point of attachment of a chemical moiety to the remainder of a molecule or chemical formula.

A "base," as used herein, means a group selected from the following: adenine, guanine, cytosine, uracil, thymine, uridine, pyrimidine, purine, pseudouridine, inosine, hypoxanthine, rhodamine, fluroscein, 2-aminopurine, cytidine, 2'-deoxycytidine, 1,3-Diaza-2-oxophenothiazine, dihydrouridine, queuosine, wyosine, cyanophage S-2L diaminopurine, isoguanine, isocytosine, diaminopyrimidine, 2,4-difluorotoluene, 4-methylbenzimidazole, isoquinoline, pyrrolo[2,3-b]pyridine, 2-amino-6-(2-thienyl)purine, pyrrole-2-carbaldehyde, 2,6-bis(ethylthiomethyl)pyridine, pyridine-2,6-dicarboxamide, 2'-deoxyinosine, 2-amino-8-(2-thienyl)purine, pyridine-2-one, 7-(2-thienyl)imidazo[4,5-b]pyridine, pyrrole-2-carbaldehyde, 4-[3-(6-aminohexanamido)-1-propynyl]-2-nitropyrrole, or modified derivative thereof.

The term "LNA," as used herein, means any nucleic acid analog disclosed herein comprising a cyclic structure between the C2 and C4 carbon of the sugar moiety of a nucleic acid. In some embodiments, the LNA has the structure below:

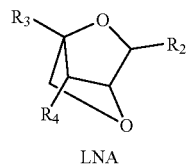

LNA wherein $R_2$ is independently selected from: any natural or unnatural base or nucleobase. In some embodiments, $R_2$ is independently selected from: adenine, guanine, cytosine, uracil, thymine, uridine, pyrimidine, purine, pseudouridine, inosine, or hypoxanthine; wherein $R_3$ is independently selected from a: phosphodiester, phosphorothioate, aldehyde, carboxyl, carbonyl, ether, ester, or amino; wherein $R_4$ is independently selected from a: phosphodiester, phosphorothioate, aldehyde, carboxyl, carbonyl, ether, ester, or amino; or a pharmaceutically active salt thereof.

The terms "subject," "individual," and "patient" are used interchangeably herein to refer to a vertebrate, preferably a mammal, more preferably a human. Mammals include, but are not limited to, murines, simians, humans, farm animals, cows, pigs, goats, sheep, horses, dogs, sport animals, and pets. Tissues, cells and their progeny obtained in vivo or cultured in vitro are also encompassed by the definition of the term "subject." The term "subject" is also used throughout the specification in some embodiments to describe an animal from which a cell sample is taken or an animal to which a disclosed cell or nucleic acid sequences have been administered. In some embodiment, the animal is a human. For treatment of those conditions which are specific for a specific subject, such as a human being, the term "patient" may be interchangeably used. In some instances in the description of the present disclosure, the term "patient" will refer to human patients suffering from a particular disease or disorder. In some embodiments, the subject may be a non-human animal from which an endothelial cell sample is isolated or provided. The term "mammal" encompasses both humans and non-humans and includes but is not limited to humans, non-human primates, canines, felines, murines, bovines, equines, caprines, and porcines.

"Variants" is intended to mean substantially similar sequences. For nucleic acid molecules, a variant comprises a nucleic acid molecule having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" nucleic acid molecule or polypeptide comprises a naturally occurring nucleotide sequence or amino acid sequence, respectively. For nucleic acid molecules, conservative variants include those sequences that, because of the degeneracy of the genetic code, encode the amino acid sequence of one of the polypeptides of the disclosure. Variant nucleic acid molecules also include synthetically derived nucleic acid molecules, such as those generated, for example, by using site-directed mutagenesis but which still encode a protein of the disclosure. Generally, variants of a particular nucleic acid molecule of the disclosure will have at least about 70%, 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein.

Variants of a particular nucleic acid molecule of the disclosure (i.e., the reference DNA sequence) can also be evaluated by comparison of the percent sequence identity between the polypeptide encoded by a variant nucleic acid molecule and the polypeptide encoded by the reference nucleic acid molecule. Percent sequence identity between any two polypeptides can be calculated using sequence alignment programs and parameters described elsewhere herein. Where any given pair of nucleic acid molecule of the disclosure is evaluated by comparison of the percent sequence identity shared by the two polypeptides that they encode, the percent sequence identity between the two encoded polypeptides is at least about 70%, 75%, 80%, 85%, 90%, 91%, 92%, 93%, 94%, 95%, 96%, 97%, 98%, 99% or more sequence identity. In some embodiments, the term "variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins or polynucleotides encompassed by the present disclosure are biologically active, that is they continue to possess the desired biological activity of the native or claimed protein or polynucleotide as described herein. Such variants may result from, for example, genetic polymorphism or from human manipulation. Biologically active variants of a protein of the disclosure will have at least about 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the disclosure may differ from that protein by as few as 1-15 amino acid residues, as few as 1-10, such as 6-10, as few as 5, as few as 4, 3, 2, or even 1 amino acid residue. The proteins or polypeptides of the disclosure may be altered in various ways including amino acid substitutions, deletions, truncations, and insertions. Methods for such manipulations are generally known in the art. For example, amino acid sequence variants and fragments of the proteins can be prepared by mutations in the nucleic acid sequence that encodes the amino acid sequence recombinantly.

In some embodiments, any natural or non-natural nucleic acid formula may be repeated across 1, 2, 3, 4, 5, 6, 7, 8, 9, 10 or more nucleic acids in contiguous nucleic acids or in a non-contiguous nucleotides across the length of the nucleic acid. In some embodiments, the disclosed nucleic acid sequences comprise 1, 2, 3, 4, 5, 6, 7, 8, 9, 10, 11, 12, 13, 14, 15, 16, 17, 18, 19, 20 or more contiguous or non-contiguous modified nucleic acids across a length of the nucleic acid.

In some embodiments, the composition or pharmaceutical composition disclosed herein comprises a nucleic acid disclosed herein that comprises ribonucleic acid and about 10%, 11%, 12%, 13%, 14%, 15%, 16%, 17%, 18%, 19%, 20%, 22%, 25%, 27%, 30%, 32%, 35%, 37%, 40%, 42%, 45%, 47%, 50%, 52%, 55%, 57%, 60%, 62%, or 65% modified nucleotides.

In some embodiments, any of the forgoing formulae may comprise one or a plurality of LNA molecules positioned between or bound to one or a plurality of modified or unmodified nucleotides.

In some embodiments, the composition or pharmaceutical composition disclosed herein comprises a nucleic acid sequence comprising a total of about 8, 10, 12, 14, 15, 16, 18, 20, 25, 30, 35, 40, 45, 50, 55, 60, 65, 70, 75, 80, 85, 90, 95, 100, or 120 nucleotides in length and comprising in 5' to 3' orientation: LNA domain and a DNA gap domain. In some embodiments, the composition or pharmaceutical composition disclosed herein comprises a nucleic acid sequence comprising a total of about 8, 10, 12, 14, 15, 16, 18, 20, 25, 30, 35, 40, 45, 50, 55, 60, 65, 70, 75, 80, 85, 90, 95, 100, or 120 nucleotides in length and comprising in 5' to 3' orientation: a first LNA domain, a DNA gap domain and a second LNA domain. In some embodiments the composition or pharmaceutical composition disclosed herein comprises a nucleic acid sequence comprising a total of about 8, 10, 12, 14, 15, 16, 18, 20, 25, 30, 35, 40, 45, 50, 55, 60, 65, 70, 75, 80, 85, 90, 95, 100, or 120 nucleotides in length and comprising in 5' to 3' orientation: a first LNA domain, a DNA gap domain, and a second LNA domain all contiguously oriented.

In certain embodiments, the modification of the nucleotide in the DNA gap domain is one or more of 2'-O-methyl, 2'-O-fluoro, or phosphorothioate. In certain embodiments, the nucleotide is modified at the 2' position of the sugar moiety. In certain embodiments, the modification at the 2' position of the sugar moiety is 2'-O-methyl or 2'-O-fluoro. In certain embodiments, the nucleotide is modified at the 3' position of the sugar moiety. In certain embodiments, the modification at the 3' position of the sugar moiety is phosphorothioate. In certain embodiments, the nucleotide is modified at both the 2' position of the sugar moiety and at the 3' position of the sugar moiety. In certain embodiments, the nucleotide is not modified at the 2' position of the sugar moiety. In certain embodiments, the nucleotide is not modified at the 3' position of the sugar moiety.

In a particular embodiment, the nucleic acid molecule comprises a DNA gap domain comprising from about 6 to about 11 nucleotides, wherein the DNA gap domain has at least 70% sequence homology to a nucleic acid sequence chosen from: SEQ ID NO: 14, SEQ ID NO: 15, SEQ ID NO: 16, SEQ ID NO: 17, SEQ ID NO: 18, SEQ ID NO: 19, and SEQ ID NO: 20, and wherein one or more of the nucleotides are modified.

In certain embodiments of the aforementioned nucleic acid molecules, only the LNA domain comprises one or more modified nucleotides. In certain embodiments, only the DNA gap domain of the nucleic acid molecule comprises one or more modified nucleotides. In certain embodiments, both the LNA domain and the DNA gap domain comprise one or more modified nucleotides.

In certain aspects, the invention also relates to a pharmaceutical composition comprising any of the aforementioned nucleic acid molecules. In certain embodiments, the pharmaceutical composition comprises a nanoparticle comprising any of the aforementioned nucleic acid molecules.

In some embodiments, the nucleic acid sequence comprises one or a plurality of intervening sequences, or linkers, between any one or plurality of domains. In some embodiments, the intervening sequence is no more than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 60, 61, 62, 63, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides in length.

The DNA gap domain can be from about 3 to about 150 nucleotides long, or longer (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 60, 61, 62, 63, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100 nucleotides in length, or longer). In some cases, the DNA gap domain is from about 6 to about 50 nucleotides in length (e.g., from about 6 to about 34, 6-46, 6-40; 7-35, 7-30, 7-28, 7-25; or about 25-50, 25-55, 25-60, or 5-20 nucleotides in length).

Generally, the "DNA gap region" or "DNA gap domain" is a nucleic acid sequence designed to complement or substantially complement a target nucleic acid sequence or sequences, such as an mRNA sequence in a target cell. In some embodiments, the region of the nucleic acid is also called a "nucleotide binding region," and such terms are used equivalently in this application, because of its ability to bind to complementary or partially complementary target sequences. In some embodiments, the mRNA sequence in a target cell is a mammalian DUX4 or any portion thereof.

The term "2'-O-MOE domain" means a nucleic acid sequence designed to complement or substantially complement a target nucleic acid sequence or sequences, such as an mRNA sequence in a target cell that includes at least one, two, three, four or more 2'-MOE modifications in a nucleotide.

The nucleotide binding domain can incorporate wobble or degenerate bases to bind multiple sequences. In some cases, the binding region can be altered to increase stability. For example, non-natural nucleotides, can be incorporated to increase RNA resistance to degradation. In some cases, the binding region can be altered or designed to avoid or reduce secondary structure formation in the binding region. In some cases, the binding region can be designed to optimize G-C content. In some cases, G-C content is from about 40% and about 60% (e.g., 40%, 45%, 50%, 55%, 60%). In some cases, the nucleotide binding region can contain modified nucleotides such as, without limitation, methylated, phosphorylated, fluorinated, or hydroxylated nucleotides. In some cases, the nucleotide binding region can contain modified nucleotides such as, without limitation, methylated, phosphorylated, fluorinated, or hydroxylated nucleotides; wherein if the nucleotide is fluorinated, the nucleotide may also be bound to one or more adjacent modified or unmodified nucleotides by a phosphorothioate bond, in either R or S orientation.

In some embodiments, the nucleotide binding region binds or is capable of hybridizing with DNA, RNA, or hybrid RNA/DNA sequences, such as any of those target sequences described herein. In some embodiments, any of the domains or elements comprises DNA, RNA, or hybrid RNA/DNA sequences. In some embodiments, the DNA gap domain comprises from about 5% to about 100% modified nucleotides based upon the total number of the nucleotides in the entire sequence. In some embodiments, the DNA gap domain comprises from about 5% to about 90% modified nucleotides as compared to an unmodified or naturally occurring nucleotide sequence. In some embodiments, the DNA gap domain comprises from about 5% to about 80% modified nucleotides. In some embodiments, the DNA gap domain comprises from about 5% to about 70% modified nucleotides. In some embodiments, the DNA gap domain comprises from about 5% to about 60% modified nucleotides. In some embodiments, the DNA gap domain comprises from about 5% to about 50% modified nucleotides. In some embodiments, the DNA gap domain comprises from about 5% to about 40% modified nucleotides. In some embodiments, the DNA gap domain comprises from about 5% to about 30% modified nucleotides. In some embodiments, the DNA gap domain comprises from about 5% to about 20% modified nucleotides. In some embodiments, the DNA gap domain comprises from about 5% to about 10% modified nucleotides. In some embodiments, the DNA gap domain comprises from about 5% to about 9% modified nucleotides.

In some embodiments, the DNA gap domain comprises hybrid RNA/DNA sequences of either unmodified or modified nucleotides. In some embodiments, the DNA gap domain comprises no less than about 250, 200, 150, 100, 50, 45, 40, 35, 30, 25, or 20 nucleotides, wherein no more than about 50, 45, 40, 35, 30, 25, 20, 15, 14, 13, 12, 11, 10, 9, 8, 7, 6, 5, 4, 3, 2, or 1 nucleotides is a modified or unmodified deoxyribonucleic acid. In some embodiments, the DNA gap domain comprises no less than about 250, 200, 150, 100, 50, 45, 40, 35, 30, 25, or 20 nucleotides, wherein no more than about 50, 45, 40, 3 5, 30, 25, 20, 15, 14, 13, 12, 11, 10, 9, 8, 7, 6, 5, 4, 3, 2, or 1 nucleotides from the 5' end of the nucleic acid sequence is a modified or unmodified deoxyribonucleic acid.

Variants of a particular nucleic acid molecule of the disclosure (i.e., the reference DNA sequence) can also be evaluated by comparison of the percent sequence identity between the nucleic acid and the variant nucleic acid molecule and the polypeptide encoded by the reference nucleic acid molecule. In some embodiments the nucleic acid sequence or molecules disclosed herein encompass variants. Percent sequence identity between any two nucleic acid molecules can be calculated using sequence alignment programs and parameters described elsewhere herein. Where any given pair of nucleic acid molecule of the disclosure is evaluated by comparison of the percent sequence identity shared by the two nucleotides such that they encode, the percent sequence identity between the two encoded nucleoc acid sequence is at least about 70%, 75%, 80%, 85%, 90%, 91%, 92%, 93%, 94%, 95%, 96%, 97%, 98%, 99% or more sequence identity. In some embodiments, the term "variant" nucleotide sequence is intended to mean a nucleotide sequence derived from the native or disclosed nucleotide by deletion (so-called truncation) of one or more nucleic acid sequences at the 5' prime and 3' prime-terminal and/or terminal end of the native or disclosed nucleotide sequence; deletion and/or addition of one or more amino acids at one or more internal sites in the native or disclosed nucleotide sequence; or substitution of one or more bases or modifications at one or more sites in the native or disclosed nucleotide sequence. Variant nucleotide sequences encompassed by the present disclosure are biologically active, that is they continue to possess the desired biological activity of the disclosed nucleotide acid sequence as described herein. Such variants may result from, for example, genetic polymorphism or from human manipulation. Biologically active variants of a nucleic acid sequences of the disclosure will have at least about 70%, 75%, 80%, 85%, 90%, 91%, 92%, 93%, 94%, 95%, 96%, 97%, 98%, 99% or more sequence identity to the nucleic acid sequence for the disclosed or native protein as determined by sequence alignment programs and parameters disclosed herein. A biologically active variant of a nucleotide sequence of the disclosure may differ from the disclosed nucleotide sequence by as few as about 1, 2, 3, 4, 5, 6, 7, 8, 9, 10, 11, 12, 13, 14 or about 15 nucleobases, as few as about 1 to about 10, such as 6-10, as few as 5, as few as 4, 3, 2, or even 1 nucleobase. The nucleotide sequences of the disclosure may be altered in various ways including base substitutions, deletions, truncations, and insertions. Methods for such manipulations are generally known in the art. For example, nucleotide sequence variants and fragments of the proteins can be prepared by standard PCR-induced mutations in the nucleic acid sequence by the designing primers with the mutations to be added or deleted.

"Internucleotide linkage" refers to any group, molecules or atoms that covalently or noncovalently join two nucleosides. Unmodified internucleotide linkages are phosphodiester bonds. In some embodiments, the nucleic acid sequence comprises at least about 10%, 20%, 30%, 40%, 50%, 60%, 70%, 75%, 80%, 85%, 90%, 91%, 92%, 93%, 94%, 95%, 96%, 97%, 98%, 99% or more modified internucleotide linkages. Modified internucleotide linkages are set forth in the U.S. Pat. No. 8,133,669 and WO1994002499, each of which is incorporated herein in its entirety. Examples of such well known modified linkages, for which conventional synthesis schemes are known, include alkylphosphonate, phosphodiester, phosphotriester, phosphorothioate, phosphorodithioate, phosphoramidate, ketone, sulfone, carbonate and thioamidate linkages. In some embodiments, the composition or pharmaceutical compositions disclosed herein comprise a nucleotide acid sequence disclosed herein with one or more internucleotide linkages that are modified or mutated at any one or plurality of positions within the sequence.

Compositions

The disclosure relates to a nucleic acid molecule or nucleic acid molecules comprising a nucleic acid sequence of two, three, four, five or more domains, each domain comprising or consisting of from about 1 to about 30 nucleic acids; wherein the first domain is an LNA domain and the second domain is a DNA gap domain and the first and second domains appear in the 5' to 3' orientation and optionally, the composition comprising from about 1% to about 100% modified nucleic acids. In some embodiments, the composition comprises the nucleic acid sequence with a third domain which is a second LNA domain and the domains appear in the 5' to 3' orientation as: LNA-DNA gap-LNA. In some embodiments, the domains are contiguous or non-contiguous with from about 1 to about 100 or more nucleotides in between one or more domains.

In some embodiments, the disclosure relates to a nucleic acid sequence and compositions comprising the same. In another aspect, the disclosure relates to a nucleic acid sequence disclosed herein and compositions comprising the same with or without a vector capable of delivery of the nucleic acid. In some embodiments, the vector is a viral vector or a bacterial vector wherein such vector is attenuated and/or replication deficient such that administration of the vector comprising or encapsulating the disclosed nucleic acid sequence is capable of delivering its payload into a transduced cell but otherwise unable to divide and ro replicate sufficiently to cause an infection due to the absence viral nucleic acid or attenuation of the vector particle.

As a non-limiting example, compositions of the disclosure can comprise a nucleic acid sequence of N'—[Z]$_n$—N"; wherein N' is any modified or unmodified 5' LNA domain; N" is any modified or unmodified 3' LNA domain; any n is any positive integer from about 1 to about 250, wherein each position of Z in the formula may have an independently selected positions at their respective $R_1$, $R_2$, $R_3$, and $R_4$, subgroups. As a non-limiting example, compositions of the disclosure relate to a nucleic acid sequence of N'—[Z]$_{10}$-N"; wherein N' is any modified or unmodified 5' terminal nucleotide; N" is any modified or unmodified 3' terminal nucleotide; wherein [Z]$_{10}$ is [$Z_1$-$Z_2$-$Z_3$-$Z_4$-$Z_5$-$Z_6$-$Z_7$-$Z_8$-$Z_9$-$Z_{10}$] and each position of Z in the formula may have an independently selected positions at their respective $R_1$, $R_2$, $R_3$, and $R_4$, subgroups. As a another non-limiting example, compositions of the disclosure may comprise a nucleic acid sequence of N'—[Z]$_n$—N"; wherein N' is any modified or unmodified 5' terminal nucleotide; N" is any modified or unmodified 3' terminal nucleotide; any n is any positive integer from about 1 to about 100, wherein each position of Z in the sequence may have an independently selected positions at their respective $R_1$, $R_2$, $R_3$, and $R_4$, subgroups.

The oligonucleotides of the disclosure may be conveniently synthesized using solid phase synthesis of known methodology, and is designed at least at the nucleotide-binding domain to be complementary to or specifically hybridizable with the preselected nucleotide sequence of the target RNA or DNA. Nucleic acid synthesizers are commercially available and their use is understood by persons of ordinary skill in the art as being effective in generating any desired oligonucleotide of reasonable length. Methods of making the nucleic acid sequences disclosed herein are contemplated by this application in which such nucleotide sequences may be manufactured by solid phase synthesis, by recombinant expression of one or more nucleotides in an in vitro culture, or a combination of both in which modifications may be introduced at one or more positions across the length of the sequences.

In some embodiments, the degree of complementarity between a DNA gap sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a nucleic acid sequence domain is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a nucleic acid sequence is less than about 75, 50, 45, 40, 35, 30, 25, 20, 15, 12, or fewer nucleotides in length. The ability of the DNA gap domain of the nucleic acid sequence to direct sequence-specific binding of an mRNA may be assessed by any suitable assay.

In some embodiments, the nucleotide binding domain or LNA domain consists of from about 1 to about 25 nucleotides; wherein the from 1 to about 25 nucleotides comprises a sequence similarity of about 90%, 91%, 92%, 93%, 94%, 95%, 96%, 97%, 98%, 99%, or 100% sequence homology to any target sequences identified herein or in the table provided above. In some embodiments, the nucleotide binding domain or LNA consists of from about 8 to about 30 nucleotides; wherein the from about 8 to about 30 nucleotides comprises a sequence similarity of about 90%, 91%, 92%, 93%, 94%, 95%, 96%, 97%, 98%, 99%, or 100% sequence homology to any target sequence identified herein. In some embodiments, the nucleotide binding domain or a LNA domain consists of from about 10 to about 40 nucleotides; wherein the from about 10 to about 40 nucleotides comprises a sequence similarity of about 90%, 91%, 92%, 93%, 94%, 95%, 96%, 97%, 98%, 99%, or 100% sequence homology to any target sequence identified herein. In some embodiments, the nucleotide binding domain or a DNA-binding domain consists of from about 15 to about 25 nucleotides; wherein the from 15 to about 25 nucleotides comprises a sequence similarity of about 90%, 91%, 92%, 93%, 94%, 95%, 96%, 97%, 98%, 99%, or about 100% sequence homology to any target sequence identified herein. For instance, one of ordinary skill in art could identify other DNA-binding domains which may be structurally related to those sequences provided in Table 4 to be used in connection with LNA gapmer targeting.

In some embodiments, any of the sequences disclosed herein may have a LNA domain and an DNA gap domain. Any of the domains of the disclosed oligonucleotides may be in any order from 5' to 3' orientation and may be contiguous as to each other or any one or multiple domains or elements may be non-contiguous in relation to one or more of the other domains, such that a different element, amino acid sequence, nucleotide or set of modified nucleotides may precede the 5' and/or 3' area of any domain.

In some embodiments, for instance, any one or combination of domains or sequences disclosed herein may comprise a sequence of about 1, 2, 3, 4, 5, 6, 7, 8, 9, 10, 15, 20, 25, 30, 35, 40, 45, or 50 or more modified or unmodified nucleotides flanking the 3' or 5' end of each domain. In some embodiments, for instance, any one or combination of domains or sequences disclosed herein may comprise a sequence of about 1, 2, 3, 4, 5, 6, 7, 8, 9, 10, 15, 20, 25, 30, 35, 40, 45, or 50 or more modified or unmodified uracils flanking the 3' or 5' end of each domain. Each domain may comprise from about 10 to about 15, 20, 25, 30, 35, 40, 45, 50, 60, 65, 70, 75, 80, 85, 90, 95, 100, 110, 120, 130, 140, 150, 160, 170, 180, 190, 200, 210, 220, 230, 240, or 250 or more modified or unmodified nucleic acids of DNA or RNA.

In some embodiments, the disclosure relates to a compositions comprising a nucleic acid sequence comprising, consisting essentially of, or consisting of a sequence that is 70%, 75%, 80%, 85%, 90%, 91%, 92%, 93%, 94%, 95%, 96%, 97%, 98%, 99% homologous to any one or combination of sequences disclosed herein, wherein the nucleic acid sequence comprises a fragment or variant of the sequences disclosed herein but possesses the same or substantially the same function as the full-length sequence disclosed herein. For example, in the case of a fragment or variant of a nucleic acid sequence disclosed herein that comprises modified nucleotides in the DNA-binding domain, in some embodiments, the variant or fragment would be functional insomuch as it would exceed or retain some or all of its capacity to bind DNA at that domain as compared to the full-length sequence.

Any of the disclosed nucleic acid sequences may comprise any one or combination or set of modifications disclosed herein. In some embodiments, the nucleic acid comprises RNA, DNA, or combinations of both RNA and DNA. In some embodiments, the nucleotide sequence, optionally in respect to one or a plurality of domains, comprises a modified nucleobase or a modified sugar.

Modifications to nucleotides are known in the art but include any of the disclosed modifications in the present application. Oligonucleotides particularly suited for the practice of one or more embodiments of the present disclosure comprise 2'-sugar modified oligonucleotides wherein one or more of the 2'-deoxy ribofuranosyl moieties of the nucleoside is modified with a halo, alkoxy, aminoalkoxy, alkyl, azido, or amino group. For example, the substitutions which may be independently selected from F, CN, $CF_3$, $OCF_3$, OCN, O-alkyl, S-alkyl, SMe, $SO_2Me$, $ONO_2$, $NO_2$, $NH_3$, $NH_2$, NH-alkyl, $OCH_3=CH_2$ and OCCH. In each of these, alkyl is a straight or branched chain of $C_1$ to $C_{20}$, having unsaturation within the carbon chain. A preferred alkyl group is $C_1$-$C_9$ alkyl. A further preferred alkyl group is $C_5$-$C_{20}$ alkyl. In some embodiments, any of the nucleotide sequences disclosed herein may be modified with a 2'O-methylphosphorothioate (2'OMePS) modification, a phosphorodiamidate morpholino (PMO) modification, a 2'methoxyethoxy (2'-MOE) modification, a vivo-morpholino (vPMO) modification, a peptide conjugate, a peptide nuclein acid (PNA), and LNA. In some embodiments, the nucleotide sequence further comprises from about 1% to about 99% modified nucleotides chosen from: a 2'O-methylphosphorothioate (2'OMePS) modification, a phosphorodiamidate morpholino (PMO) modification, a 2'methoxyethoxy (2'-MOE) modification, a vivo-morpholino (vPMO) modification, a peptide conjugate, a peptide nuclein acid (PNA), and LNA.

In further embodiments of the present disclosure, the individual nucleotides of the oligonucleotides of the disclosure are connected via phosphorus linkages. Phosphorus linkages include phosphodiester, phosphorothioate and phosphorodithioate linkages. In one preferred embodiment of this disclosure, nuclease resistance is conferred on the oligonucleotides by utilizing phosphorothioate internucleoside linkages.

In further embodiments of the disclosure, nucleosides can be joined via linkages that substitute for the internucleoside phosphate linkage. Macromolecules of this type have been identified as oligonucleosides. The term "oligonucleoside" thus refers to a plurality of nucleoside units joined by non-phosphorus linkages. In such oligonucleosides the linkages include an —O—$CH_2$—$CH_2$—O— linkage (i.e., an ethylene glycol linkage) as well as other novel linkages disclosed in U.S. Pat. No. 5,223,618, issued Jun. 29, 1993, U.S. Pat. No. 5,378,825, issued Jan. 3, 1995 and U.S. patent application Ser. No. 08/395,168, filed Feb. 27, 1995. Other modifications can be made to the sugar, to the base, or to the phosphate group of the nucleotide. Representative modifications are disclosed in International Publication Numbers WO 91/10671, published Jul. 25, 1991, WO 92/02258, published Feb. 20, 1992, WO 92/03568, published Mar. 5, 1992, and U.S. Pat. No. 5,138,045, issued Aug. 11, 1992, all of which are herein incorporated by reference in their entireties.

In some embodiments, a nucleic acid sequence is selected to reduce the degree of secondary structure within the nucleic sequence. Secondary structure may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, Cell 106(1): 23-24; and PA Carr and GM Church, 2009, Nature Biotechnology 27(12): 1151-62). Further algorithms may be found in U.S. application Ser. No. 61/836,080 filed Jun. 17, 2013; incorporated herein by reference in its entirety.

In another embodiment, the disclosure provides a cell or a vector comprising one of the nucleic acids of the disclosure or functional fragments thereof. The cell may be an animal cell or a plant cell. In some embodiments, the cell is a mammalian cell, such as a human cell.

In one aspect, the disclosure provides a vector system comprising one or more vectors. In some embodiments, the system comprises: (a) a synthetic nucleic acid sequence comprising at least one of the nucleic acid sequences disclosed herein, wherein the nucleic acid sequence directs sequence-specific portion of the DNA gap domain to a target sequence in a eukaryotic cell. In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Another aspect of the disclosure relates to a composition comprising a nucleic acid disclosed herein and one or a plurality of recombinant expression vectors. Generally, the disclosure relates to composition comprising a synthetic nucleic acid sequence and one or a plurality of recombinant expression vectors. Recombinant expression vectors can comprise a nucleic acid of the disclosure in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) (see, e.g., Boshart et al, Cell, 41:521-530 (1985)), the SV40 promoter, the dihydrofolate reductase promoter, the β-actin promoter, the phosphoglycerol kinase (PGK) promoter, and the EF1a promoter. Also encompassed by the term "regulatory element" are enhancer elements, such as WPRE; CMV enhancers; the R-U5' segment in LTR of HTLV-1 (Mol. Cell. Biol., Vol. 8(1), p. 466-472, 1988); SV40 enhancer; and the intron sequence between exons 2 and 3 of rabbit 3-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. One or more nucleic acid sequences and one or more vectors can be introduced into host cells to form complexes with other cellular or non-natural compounds, produce transcripts, proteins, or peptides, including fusion proteins or peptides, encoded by nucleic acids as described herein.

The disclosure also relates to pharmaceutical compositions comprising: (i) one or nucleic acid sequences disclosed herein or one or more pharmaceutically acceptable salts thereof; and (ii) a pharmaceutically acceptable carrier. The term "pharmaceutically acceptable salts" refers to physiologically and pharmaceutically acceptable salts of the nucleic acid sequences of the disclosure: i.e., salts that retain the desired biological activity of the nucleic acid sequences and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. of Pharnut Sci., 1977, 66:1). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present disclosure. As used herein, a "pharmaceutical addition salt" includes a pharmaceutically acceptable salt of an acid form of one of the components of the compositions of the disclosure. These include organic or inorganic acid salts of the amines. In some embodiments, a pharmaceutically acceptable salt is selected from one or a combination of hydrochlorides, acetates, salicylates, nitrates and phosphates.

Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids; for example acetic acid, propionic acid, glycolic acid, succinic acid, malefic acid, hydroxymaleic acid, methylmaleic acid, fiunaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, malefic acid, fumaric acid, glucoruc acid, citric acid, malic acid, ascorbic acid, benzoic acid, tannic acid, palimitic acid, alginic acid, polyglutamic acid, naphthalenesulfonic acid, methanesulfonic acid, p-toluenesulfonic acid, naphthalenedisulfonic acid, polygaiacturonic acid, and the like; and (d) salts formed from elemental anions such as chlorine, bromine, and iodine.

The practice of the present disclosure employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)), all of which are incorporated by reference in their entireties.

In some embodiments, the nucleic acid sequence comprises one or a plurality of radioactive moieties. Radioactive moiety means a substituent or component of a compound that comprises at least one radioisotope. Any radioisotope may be used. In some embodiments, the radioisotope is selected from Table 2. In some embodiments, the substituent or component of a compound of the present invention may incorporate any one, two, three, or more radioisotopes disclosed in Table 2.

TABLE 2

| Radioisotopes that may be incorporated into pharmaceutical compositions |
|---|
| $^{2}$H, $^{3}$H, $^{13}$C, $^{14}$C, $^{15}$N, $^{16}$O, $^{17}$O, $^{31}$P, $^{32}$P, $^{35}$S, $^{18}$F, $^{36}$Cl, $^{225}$Ac, $^{227}$Ac, $^{212}$Bi, $^{213}$Bi, $^{109}$Cd, $^{60}$Co, $^{64}$Cu, $^{67}$Cu, $^{166}$Dy, $^{169}$Er, $^{152}$Eu, $^{154}$Eu, $^{153}$Gd, $^{198}$Au, $^{166}$Ho, $^{125}$I, $^{131}$I, $^{192}$Ir, $^{177}$Lu, $^{99}$Mo, $^{194}$Os, $^{103}$Pd, $^{195m}$Pt, $^{32}$P, $^{33}$P, $^{223}$Ra, $^{186}$Re, $^{188}$Re, $^{105}$Rh, $^{145}$Sm, $^{153}$Sm, $^{47}$Sc, $^{75}$Se, $^{85}$Sr, $^{89}$Sr, $^{99m}$Tc, $^{228}$Th, $^{229}$Th, $^{170}$Tm, $^{117m}$Sn, $^{188}$W, $^{127}$Xe, $^{175}$Yb, $^{90}$Y, $^{91}$Y |

In some embodiments, the composition or pharmaceutical composition comprises any nucleic acid disclosed herein or its salt and one or more additional therapies, including but not limited to a corticosteroid, an anticonvulsant, an immunosuppressant, an antibiotic, an angiotensin-converting enzyme (ACE) inhibitor, and a beta blocker. In some embodiments, the pharmaceutical composition comprises any one or plurality of nucleic acids disclosed herein or its salt or variant thereof and/or one or more therapies is administered to the subject before, contemporaneously with, substantially contemporaneously with, or after administration of the pharmaceutical composition.

Compositions of the disclosure include pharmaceutical compositions comprising: a particle comprising any of the nucleic acid sequences disclosed herein, or pharmaceutically acceptable salts thereof: and a pharmaceutically acceptable carrier. In some embodiments, the pharmaceutically acceptable carrier is distilled water or saline. In preferred embodiments, the pharmaceutically acceptable carrier is free of RNase/DNase.

As used herein, a "particle" refers to any entity having a diameter of less than 100 microns (μm). Typically, particles have a longest dimension (e.g. diameter) of 1000 nm or less. In some embodiments, particles have a diameter of 300 nm or less. In some embodiments, nanoparticles have a diameter of 200 nm or less. In some embodiments, nanoparticles have a diameter of 100 nm or less. In general, particles are greater in size than the renal excretion limit, but are small enough to avoid accumulation in the liver. In some embodiments, a population of particles may be relatively uniform in terms of size, shape, and/or composition. In general, inventive particles are biodegradable and/or biocompatible. Inventive particles can be solid or hollow and can comprise one or more layers. In some embodiments, particles are spheres, spheroids, flat, plate-shaped, cubes, cuboids, ovals, ellipses, cylinders, cones, or pyramids. In some embodiments, particles can be a matrix of polymers. In some embodiments, the matrix is cross-linked. In some embodiments, formation of the matrix involves a cross-linking step. In some embodiments, the matrix is not substantially cross-linked. In some embodiments, formation of the matrix does not involve a cross-linking step. In some embodiments, particles can be a non-polymeric particle (e.g. a metal particle, quantum dot, ceramic, inorganic material, bone, etc.). Components of the pharmaceutical compositions disclosed herein may comprise particles or may be microparticles, nanoparticles, liposomes, and/or micelles comprising one or more disclosed nucleic acid sequences or conjugated to one or more disclosed amno acids. As used herein, the term "nanoparticle" refers to any particle having a diameter of less than 1000 nm. Examples of nanoparticles are disclosed in *Nature Biotechnology* 31, 638-646, which is herein incorporated by reference in its entirety. In some embodiments, the particle is an exosome.

Pharmaceutical "carrier" or "excipient", as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy,* 21st Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, the pharmaceutically acceptable excipient or carrier is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g.

sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

In some embodiments, the pharmaceutical composition comprise any one or combination of nucleic acid sequence disclosed here fused, linked or conjugated to a peptide from about 6 to about 100 amino acids long. In some embodiments, the pharmaceutical composition comprises a therapeutically effective amount of an LNA gapmer fused to a protein or peptide that is an exosome targeting domain. The exosome targeting domain comprises an amino acid sequence capable of binding or associating to a receptor on an exosome.

Compositions of the disclosure relate to LNA gapmers bound to exosome via an exosome targeting domain which is a nucleic acid sequence, amino acid sequence, or nucleic acid-amino acid fusion. In some embodiments, the composition comprises a nucleic acid sequence fused to a ligand. The ligand of the fusion typically is a heterologous amino acid sequence (i.e., relative to the engineered glycosylation site and/or relative to the exosome-targeting domain) that binds to a receptor present on the surface of a target cell (e.g., a protein receptor, a carbohydrate receptor, or a lipid receptor present on the surface of a cell). For example, suitable ligands may include a ligand for a cell receptor present on a target cell, or an antibody or binding fragment thereof that binds to a cell receptor or other membrane protein present on a target cell.

Methods of Making Compositions and Modifications

Modified oligonucleotides may be made with automated, solid phase synthesis methods known in the art. During solid phase synthesis, phosphoramidite monomers are sequentially coupled to a nucleoside that is covalently linked to a solid support. This nucleoside is the 3' terminal nucleoside of the modified oligonucleotide. Typically, the coupling cycle comprises four steps: detritylation (removal of a 5'-hydroxyl protecting group with acid), coupling (attachment of an activated phosphoroamidite to the support bound nucleoside or oligonucleotide), oxidation or sulfurization (conversion of a newly formed phosphite trimester with an oxidizing or sulfurizing agent), and capping (acetylation of unreacted 5'-hydroxy 1 groups). After the final coupling cycle, the solid support-bound oligonucleotide is subjected to a detritylation step, followed by a cleavage and deprotection step that simultaneously releases the oligonucleotide from the solid support and removes the protecting groups from the bases. The solid support is removed by filtration, the filtrate is concentrated and the resulting solution is tested for identity and purity. The oligonucleotide is then purified, for example using a column packed with anion-exchange resin.

This term includes oligonucleotides composed of naturally-occurring nucleobases, sugars and covalent internucleoside (backbone) linkages as well as oligonucleotides having non-naturally-occurring portions which function similarly Such modified or substituted oligonucleotides are often preferred over native forms because of desirable properties such as, for example, enhanced cellular uptake, enhanced affinity for nucleic acid target and increased stability in the presence of nucleases.

In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference in its entirety.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts. Any of the olignucelotide backbone modifications here may replace any one of the internucleotide linkages set forth in any of the disclosed nucleotide sequences.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289;

5,602,240; 5,608,046; 5,610,289; 5,618,704; 5,623,070; 5,663,312; 5,633,360; 5,677,437; and 5,677,439, each of which is herein incorporated by reference in its entirety.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Some embodiments of the disclosure are oligonucleotides with phosphorothioate backbones and oligonucleosides with heteroatom backbones, and in particular —CH2-NH—O—CH2-, —CH2-N(CH3)-O—CH2- [known as a methylene (methylimino) or MMI backbone], —CH2-O—N(CH3)-CH2-, —CH2-N(CH3)-N(CH3)-CH2- and —O—N(CH3)-CH2-CH2- [wherein the native phosphodiester backbone is represented as —O—P—O—CH2-] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. In some embodiments, oligonucleotides of the disclosure comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[(CH$_2$)nO]mCH$_3$, O(CH$_2$)nOCH$_3$, O(CH$_2$)nNH$_2$, O(CH$_2$)nCH$_3$, O(CH$_2$)nONH$_2$, and O(CH$_2$)nON[(CH$_2$)nCH$_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, acetamide, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH2CH2OCH3, also known as 2'-O-(2-methoxyethyl) or 2'-MOE) (Martin et al., Helv. Chim. Acta, 1995, 78, 486-504) i.e., an alkoxyalkoxy group. Another modification includes 2'-dimethylaminooxyethoxy, i.e., a O(CH$_2$)$_2$ON (CH$_3$)$_2$ group, also known as 2'-DMAOE, and 2'-dimethylamino-ethoxyethoxy (2'-DMAEOE), i.e., 2'-O—CH$_2$—O—CH2-N(CH$_2$)$_2$.

In some embodiments, the disclosure relates to a pharmaceutical composition comprising an effective amount of a nucleotide sequence comprising: (i) an RNA-binding domain from about 5 to about 30 nucleotides complementary to a region of a mammalian double homeobox 4 (DUX4); and (ii) at least one locked nucleic acid (LNA) domain comprising from about 1 to about 5 nucleotides; and/or at least one 2'MOE domain comprising from about 1 to about 10 nucleotides, or a salt thereof. In some embodiments, the disclosure relates to a pharmaceutical composition comprising an effective amount of a nucleotide sequence comprising: (i) an RNA-binding domain from about 5 to about 30 nucleotides complementary to a region of a mammalian double homeobox 4 (DUX4); and (ii) at least one 2'MOE domain comprising from about 1 to about 10 nucleotides, or a salt thereof. In some embodiments, the nucleotide sequence comprises two non-contiguous 2'MOE domains flanking a sequence at least 75% homolgous to ACAGCGTCGG (SEQ ID NO: 24). In some embodiments, the disclosure relates to a pharmaceutical composition comprising an effective amount of a nucleotide sequence comprising: (i) an RNA-binding domain from about 5 to about 30 nucleotides complementary to a region of a mammalian double homeobox 4 (DUX4); and (ii) at least one 2'MOE domain comprising from about 1 to about 10 nucleotides, or a salt thereof. In some embodiments, the nucleotide sequence comprises two non-contiguous 2'MOE domains flanking a sequence at least about 75% homolgous to ACAGCGTCGG (SEQ ID NO: 24). In some embodiments, the disclosure relates to a pharmaceutical composition comprising an effective amount of a nucleotide sequence comprising: (i) an RNA-binding domain from about 5 to about 30 nucleotides complementary to a region of a mammalian double homeobox 4 (DUX4); and (ii) at least one 2'MOE domain comprising from about 1 to about 10 nucleotides, or a salt thereof, wherein the nucleoitide sequence comprises at least 70% sequence identity to CCTAGACAGCGTCG-GAAGGT (SEQ ID NO: 25) and wherein at least five nucleotides comprise a 2'-MOE modification. In some embodiments, the disclosure relates to a pharmaceutical composition comprising an effective amount of a nucleotide sequence comprising: (i) an RNA-binding domain from about 5 to about 30 nucleotides complementary to a region of a mammalian double homeobox 4 (DUX4); and (ii) at least one 2'MOE domain comprising from about 1 to about 10 nucleotides, or a salt thereof, wherein the nucleoitide sequence comprises at least 70% sequence identity to C*C*T*A*G*ACAGCGTCGGAAGGT (SEQ ID NO: 25) wherein each "*"=a 2'-O-MOE modified nucleotide with a phosphorothioate bond connecting the adjacent nucleotide. In some embodiments, the disclosure relates to a pharmaceutical composition comprising an effective amount of a nucleotide sequence comprising: (i) an RNA-binding domain from about 5 to about 30 nucleotides complementary to a region of a mammalian double homeobox 4 (DUX4); and (ii) at least one 2'MOE domain comprising from about 1 to about 10 nucleotides, or a salt thereof, wherein the nucleoitide sequence comprises at least 70% sequence identity to CCTAGACAGCGTCGG* A*A*G*G*T (SEQ ID NO: 25) wherein each "*"=a 2'-O-MOE modified nucleotide with a phosphorothioate bond connecting the adjacent nucleotide. In some embodiments the nucleic acid comprises, consists of or consists essentially of C*C*T*A*G*ACAGCGTCGG*A*A*G*G*T (SEQ ID NO: 25), wherein each "*"=a 2'-O-MOE modified nucleotide with a phosphorothioate bond connecting the adjacent nucleotide. In some embodiments the nucleic acid comprises, consists of or consists essentially of C*C*T*A*G*A*C*A*G*C*G*T*C*G*G*A*A*G*G*T (SEQ ID NO: 25), wherein each "*"=a 2'-O-MOE modified nucleotide with a phosphorothioate bond connecting the adjacent nucleotide. In some embodiments the nucleic acid comprises, consists of or consists essentially of a sequence at least 70%, 80%, 85%, 90%, 95%, or 100% homolgous to <C*C*T*A*G*>A*C*A*G*C*G*T*C*G*G*<A*A*G* G*T> (SEQ ID NO: 25), wherein each "*"=a 2'-O-MOE modified nucleotide with a phosphorothioate bond connecting the adjacent nucleotide, and wherein <X*X*>=Sequence: 2'-O-MOE RNA nucleotides and Phosphorothioate bond connecting the adjacent nucleotide; and wherein X*X*=any DNA nucleotide+Phosphorothioate bond connecting the adjacent nucleotides.

Other modifications include 2'-methoxy (2'-O—CH$_3$), 2'-aminopropoxy (2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Oligonucleotides may also include a modified thioester group on the 2', 3' and/or 5' nucleoside. Such modifications in the 5' carbon of the ribose sugar also for formation of single 5'-S-thioester linkages between nucleotides in a synthetic nucleotide sequence. In any 3' or 5' linkage between nucleotides any one or both positions may create a series of linkages between nucleotides. The linkages at the 2' or 3' can create thioester bond, phosphorothioriate linkages between two or a plurality of nucleosides in the oligonucleotide.

Strategically placed sulfur atoms in the backbone of nucleic acids have found widespread utility in probing of specific interactions of proteins, enzymes and metals. Sulfur replacement for oxygen may be carried out at the 2'-position of RNA and in the 3'-5'-positions of RNA and of DNA. Polyribonucleotide containing phosphorothioate linkages were obtained as early as 1967 by Eckstein et al. using DNA-dependent RNA polymerase from *E. coli* (57). DNA-dependent RNA polymerase is a complex enzyme whose essential function is to transcribe the base sequence in a segment of DNA into a complementary base sequence of a messenger RNA molecule. Nucleoside triphosphates are the substrates that serve as the nucleotide units in RNA. In the polymerization of triphosphates, the enzyme requires a DNA segment that serves as a template for the base sequence in the newly synthesized RNA. In the original procedure, Uridine 5'-O-(1-thiotriphosphate), adenosine 5'-O-triphosphate, and only d (AT) as a template was used. As a result, an alternating copolymer is obtained, in which every other phosphate is replaced by a phosphorothioate group. Using the same approach and uridine 5'-O-(1-thiotriphosphate) and adenosine 5'-O-(1-thiotriphosphate), polyribonucleotide containing an all phosphorothioate backbone can also synthesized. In both cases, nucleoside 5'-O-(1-thiotriphosphates) as a mixture of two diastereomers can be used. In some embodiments, alternating phosphorothioate groups link a DNA or RNA or hybrid sequence of predominantly RNA to form alternating phosphorothioate backbones. Optionally, linkers of any cyclic or acyclic hydrocarbon chains of varying length may be incorporated into the nucleic acid. In some embodiments, linkers of the disclosure comprise one or a plurality of: branched or non-branched alkyl, hydroakyl, hydroxyl, halogen, metal, nitrogen, or other atoms.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of the oligomeric compounds of the disclosure. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941, and 5,750,692, each of which is herein incorporated by reference in its entirety.

In some embodiments, the nucleic acids is conjugated to other proteins, polypeptides or molecules. Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371;

5,595,726; 5,597,696; 5,599,923; 5,599,928 and 5,688,941, each of which is herein incorporated by reference in its entirety.

It is not necessary for all positions in a given compound to be uniformly modified, and in fact more than one of the aforementioned modifications may be incorporated in a single sequence or compound or even at a single nucleoside or functional group within one or a plurality of posioins within a nucleoside or an oligonucleotide.

For example, GalNAc-conjugated modification are known to direct oligonucleotides to liver cells. Modifications, such as GalNAc-conjugated modification, may be made to any one or combination of oligonucleotides disclosed herein with automated solid phase synthesis, similar to the solid phase synthesis that produced unconjugated oligonucleotides. During the synthesis of GalNAc-conjugated oligonucleotides, the phosphoramidite monomers are sequentially coupled to a GalNAc conjugate which is covalently linked to a solid support. The synthesis of GalNAc conjugates and GalNAc conjugate solid support is described, for example in U.S. Pat. No. 8,106,022, which is herein incorporated by reference in its entirety for the description of the synthesis of carbohydrate-containing conjugates, including conjugates comprising one or more GalNAc moieties, and of the synthesis of conjugate covalently linked to solid support.

The disclosure also relates to synthesizing one or a plurality of oligonucleotides, such as LNA-DNA chimeric molecules. 2'-deoxy-2'-modified nucleosides of adenine, guanine, cytosine, thymidine and certain analogs of these nucleobases may be prepared and incorporated into oligonucleotides via solid phase nucleic acid synthesis. Novel oligonucleotides can be assayed for their hybridization properties and their ability to resist degradation by nucleases compared to the unmodified oligonucleotides. Initially, small electronegative atoms or groups can be selected because they would not be expected to sterically interfere with required Watson-Crick base pair hydrogen bonding (hybridization). However, electronic changes due to the electronegativity of the atom or group in the 2'-position may profoundly affect the sugar conformation.

2'-Substituted oligonucleotides can be synthesized by standard solid phase nucleic acid synthesis using an automated synthesizer such as Model 380B (Perkin-Elmer/Applied Biosystems) or MilliGen/Biosearch 7500 or 8800. Triester, phosphoramidite, or hydrogen phosphonate coupling chemistries [Oligonucleotides. Antisense Inhibitors of Gene Expression. M. Caruthers, p. 7, J. S. Cohen (Ed.), CRC Press, Boca Raton, Fla., 1989] are used with these synthesizers to provide the desired oligonucleotides. The Beaucage reagent [J. Amer. Chem. Soc., 112, 1253 (1990)] or elemental sulfur [Beaucage et al., Tet. Lett., 22, 1859 (1981)] is used with phosphoramidite or hydrogen phosphonate chemistries to provide 2'-substituted phosphorothioate oligonucleotides.

2'-substituted nucleosides (A, G, C, T(U), and other modified nucleobases) may be prepared by modification of several literature procedures as described below.

Procedure 1. Nucleophilic Displacement of 2'-Leaving Group in Arabino Purine Nucleosides. Nucleophilic displacement of a leaving group in the 2'-up position (2'-deoxy-2'-(leaving group)arabino sugar) of adenine or guanine or their analog nucleosides. General synthetic procedures of this type have been described by Ikehara et al., Tetrahedron, 34, 1133 (1978); ibid., 31, 1369 (1975); Chemistry and Pharmaceutical Bulletin, 26, 2449 (1978); ibid., 26, 240 (1978); Ikehara, Accounts of Chemical Research, 2, 47 (1969); and Ranganathan, Tetrahedron Letters, 15, 1291 (1977).

Procedure 2. Nucleophilic Displacement of 2,2'-Anhydro Pyrimidines. Nucleosides thymine, uracil, cytosine or their analogs are converted to 2'-substituted nucleosides by the intermediacy of 2,2'-cycloanhydro nucleoside as described by Fox et al., Journal of Organic Chemistry, 29, 558 (1964).

Procedure 3. 2'-Coupling Reactions. Appropriately 3',5'-sugar and base protected purine and pyrimidine nucleosides having a unprotected 2'-hydroxyl group are coupled with electrophilic reagents such as methyl iodide and diazomethane to provide the mixed sequences containing a 2'-OMe group H. Inoue et al., Nucleic Acids Research, 15, 6131.

Procedure 4. 2-Deoxy-2-substituted Ribosylations. 2-Substituted-2-deoxyribosylation of the appropriately protected nucleic acid bases and nucleic acids base analogs has been reported by Jarvi et al., Nucleosides & Nucleotides, 8, 1111-1114 (1989) and Hertel et al., *Journal of Organic Chemistry,* 53, 2406 (1988).

In some embodiments, the presence of the nucleic acid molecule comprising a chimeric set of nucleic acid sequences comprising the following structure: LNA domain 1-DNA gap-LNA domain 2, wherein the first LNA domain is positioned at the flank of the nucleic acid molecule and the second LNA is positioned at the opposing flank of the nucleic acid molecule and one of the two LNA domain comprises a sequence that associates with an RNA sequence in a cell (such as a DUX4 mRNA), and the other LNA domain comprises a sequence that associates with an amino acid that is expressed by a target cell, such as a muscle cell.

Methods

The disclosure relates to treating a dystrophin-related disorder in an subject in need thereof comprising administering a therapeutically effective amount of a composition or pharmaceutical composition disclosed herein. In certain embodiments, the disclosure relates to methods of treating muscular dystrophy. In some embodiments, the muscular dystrophy is Facioscapulohumeral Muscular Dystrophy (FSHD). In some embodiments, the method of treating further comprises repeating the step of administering the composition or pharmaceutical composition once a day, once every other day, once a week, once every other week or once a month. In some embodiments, the dystrophin-related disorder is any muscular dystrophy disclosed in Table 1.

TABLE 1

Overview of Muscular Dystrophies and their characteristics

| Type | Inheritance | Defective Gene/Protein | Onset | Clinical Features | Other Organ Systems Involved |
|---|---|---|---|---|---|
| Duchenne | XR | Dystrophin | Before 5 years | Progressive weakness of girdle muscles<br>Unable to walk after age 12<br>Progressive kyphoscoliosis<br>Respiratory failure in second and third decade | Cardiomyopathy<br>Mental impairment |

TABLE 1-continued

Overview of Muscular Dystrophies and their characteristics

| Type | Inheritance | Defective Gene/Protein | Onset | Clinical Features | Other Organ Systems Involved |
|---|---|---|---|---|---|
| Becker | XR | Dystrophin | Early childhood to adult | Progressive weakness of girdle muscles Able to walk after age 15 Respiration failure may develp by fourth decade | Cardiomyopathy |
| Limb-girdle | AD/AR | Several | Early childhood to early adult | Slow progressive weakness of shoulder and hip girdle muscles | Cardiomyopathy |
| Emery-Dreifuss | XR/AD/AR | EMD, FHL1, LMNA Nesprin-1, TMEM43 | Childhoot to adult | Elbow/knee/ankle contractures, humeral and peroneal weakness | Cardiomyopathy |
| Congenital | AR | Several | At birthy or within first few months | Hypotonia, contractures, delayed milestones Progression to respiratory failure in some | CNS abnormalities Eye Abnormalities |
| Myotonic (DM1, DM2) | AD | DMPK(DM1) CNBP(DM2) | Childhoot to adult; possibly infancy if mother affected (DM1 only) | Slowly progressive weakness of face, shoulder girdle, and foot dorsiflexion Preferential proximal weakness in DM2 | Cardiac conduction defects Mental impairment Cataracts Frontal baldness Gonadal atrophy |
| Oculopharyngeal | AD | | Fifth to sixth decade | Slowly progressive weakness of extraocular, pharyngeal, and limb muscles | |
| FSHD (FSHD1, FSHD2) | AD | DUX4(FSHD1) SMCHD(FSHD1) | Childhood to adult | Slowly progressive weakness of face, shoulder girdle, and foot dorsiflexion | Deafness Coats' disease |

Abbreiviations:
AD, autosomal dominant;
AR, autosomal recessive;
CNS, central nervous system;
XR, X-linked recessive
Modified from Amato & Brown, 2015.

The term "administering" or "administration" and the like, refers to providing one or a plurality of compositions or nucleic acids of the disclosure to the subject in need of treatment. Preferably the subject is a mammal, such as a human. The present disclosure also relates to administering one or a plurality of the compositions of nucleic acids of the disclosure in conjunction with a second composition, such as one or more of a corticosteroid, an anticonvulsant, an immunosuppressant, an antibiotic, an angiotensin-converting enzyme (ACE) inhibitor, or a beta blocker. In some embodiments, the composition or pharmaceutical composition and the one or more of a corticosteroid, an anticonvulsant, an immunosuppressant, an antibiotic, an angiotensin-converting enzyme (ACE) inhibitor, or a beta blocker are synergistic. When one or a plurality of the compositions or nucleic acids of the disclosure are administered in conjunction with a second composition, the one or a plurality of the compositions of nucleic acids in the disclosure and the second composition can be administered simultaneously in the same composition, simultaneously in different dosage forms or sequentially or at different times. When the one or a plurality of compositions of nucleic acids of the disclosure and the second composition are administered at the same time, they can be administered as a single composition or pharmaceutical composition or they can be administered as separate pharmaceutical compositions. It is understood that when one or a plurality of the compositions of nucleic acids of the disclosure are administered, one or a plurality of the compositions of nucleic acids of the disclosure can be administered in conjunction with a second composition, that the active agents can be administered in a single combination or in multiple combinations. For example, when administered intravenously, the one or a plurality of the compositions of nucleic acids in the disclosure can be dissolved or suspended in any of the commonly used intravenous fluids and administered by infusion, and then a second composition can be dissolved or suspended in any of the commonly used intravenous fluids and administered by infusion. Conversely, the second composition can be dissolved or suspended in any of the commonly used intravenous fluids and administered by infusion, and then one or a plurality of compositions of nucleic acids of the disclosure can be dissolved or suspended in any of the commonly used intravenous fluids and administered by infusion. Alternatively, a pharmaceutical composition comprising one or a plurality of the compositions of nucleic acids in the disclosure and a second composition can be dissolved or suspended in any of the commonly used intravenous fluids and administered by infusion.

All nucleic acid sequences or Accession Numbers below as of Sep. 19, 2017, are incorporated by reference in their entireties. Any mutants or variants that are at least 70, 75, 80, 85, 90, 95, 96, 97, 98, 99% homologous to the encoded nucleic acids set forth in the sequences or Accession Numbers below are also incorporated by reference in their entireties. The amino acid sequences that are encoded by the nucleic acid sequences are also contemplated by this disclosure as well as plasmid sequences comprising any one or plurality of expressible nucleic acid sequences that are at least 70%, 80%, 85%, 90%, 95%, 96%, 97%, 98%, 99% or 100% homologous to the sequences below. Amino acid variants and full-length protein sequences are contemplated by the disclosure and can be considered payloads for this disclosure in addition to the nucleic acid sequences.

In some embodiments, the pharmaceutical composition is administered in a liposomal formulation. In some embodiments, toxicity to other cells is prevented or reduced, such that toxic doses are tolerated in the subject.

In some embodiments, administration of the effective amount of pharmaceutical composition disclosed herein is not limited to any particular delivery system and includes, without limitation, parenteral (including subcutaneous, intravenous, intramedullary, intraarticular, intramuscular, or intraperitoneal injection), rectal, topical, transdermal, muscoal or oral (for example, in capsules, suspensions, or tablets) administration. In some embodiments, administration to a subject in need thereof occurs in a single dose or in repeat administrations, and in any of a variety of physiologically acceptable salt forms, or with an acceptable pharmaceutical carrier or additive as part of a pharmaceutical composition. In some embodiments, any suitable and physiological acceptable salt forms or standard pharmaceutical formulation techniques, dosages, and excipients are utilized. In some embodiments, the step of administering comprises administering the composition or pharmaceutical composition intravenously, intramuscularly, topically, intradermally, intramucosally, subcutaneously, sublingually, orally, intravaginally, intracavernously, intraocularly, intranasally, intrarectally, gastrointestinally, intraductally, intrathecally, subdurally, extradurally, intraventricular, intrapulmonary, into an abscess, intra articularly, into a bursa, subpericardially, into an axilla, intrauterine, into the pleural space, intraperitoneally, transmucosally, or transdermally.

In some embodiments, effective dosages achieved in one animal are extrapolated for use in another animal, including humans, using conversion factors known in the art.

In some embodiments, the pharmaceutical composition dosing amount or schedule follows clinically approved, or experimental, guidelines. In some embodiments, the dose of the pharmaceutical composition is about 1, 2, 3, 4, 5, 6, 7, 8, 9, 10, 15, 20, 25, 30, 40, 50, 60, 70, 80, 90, 100, 125, 150, 175, 200, 225, 250 or about 500 mg/kg of the subject per day.

In some embodiments the pharmaceutical composition is administered to the individual in about 1, 2, 3, 4, 5 daily doses over 5 consecutive or non-consecutive days. In some embodiments, the oligonucleotide is administered to the individual in about 1, 2, 3, 4, 5, 6, or 7 daily doses over a single week (7 days). In some embodiments, the pharmaceutical composition is administered to the individual in about 1, 2, 3, 4, 5, 6, 7, 8, 9, 10, 11, 12, 13, or 14 daily doses over 14 days. In some embodiments, the pharmaceutical composition is administered to the individual in 1, 2, 3, 4, 5, 6, 7, 8, 9, 10, 11, 12, 13, 14, 15, 16, 17, 18, 19, 20, or 21 daily doses over 21 days. In some embodiments, the pharmaceutical composition is administered to the individual in 1, 2, 3, 4, 5, 6, 7, 8, 9, 10, 11, 12, 13, 14, 15, 16, 17, 18, 19, 20, 21, 22, 23, 24, 25, 26, 27, or 28 daily doses over 28 days.

In some embodiments, the pharmaceutical composition is provided about twice a week of a 21 or a 28 day cycle. In particular embodiments, the pharmaceutical composition is provided on about days 1, 4, 8, 11, 15 and 18 of a 21 day or 28 day cycle.

In some embodiments the pharmaceutical composition is administered for: about 2 weeks (total 14 days); about 1 week with 1 week off (total 14 days); about 3 consecutive weeks (total 21 days); about 2 weeks with 1 week off (total 21 days); about 1 week with 2 weeks off (total 21 days); about 4 consecutive weeks (total 28 days); about 3 consecutive weeks with 1 week off (total 28 days); about 2 weeks with 2 weeks off (total 28 days); about 1 week with 3 consecutive weeks off (total 28 days).

In some embodiments the pharmaceutical composition disclosed herein is administered on day 1 of a 7, 14, 21 or 28 day cycle; administered on days 1 and 15 of a 21 or 28 day cycle; administered on days 1, 8, and 15 of a 21 or 28 day cycle; or administered on days 1, 2, 8, and 15 of a 21 or 28 day cycle. In some embodiments, the pharmaceutical composition is administered once every 1, 2, 3, 4, 5, 6, 7, or 8 weeks. In some embodiments, the pharmaceutical composition (and optionally a combination therapy) is administered for 1, 2, 3, 4, 5, 6, 7, 8, 9, 10, 11, or 12 cycles.

The disclosure also relates to a method of modulating or inhibiting expression of DUX4 in a subject, the method comprising administering to the subject one or a combination of compositions or pharmaceutical compositions disclosed herein. In some embodiments, the subject is suffering from or suspected of having a muscular dystrophy.

The disclosure also relates to a method of targeting a DUX4 mRNA in a cell, for example in a muscle cell, the method comprising contacting one or a combination of the compositions and/or pharmaceutical compositions disclosed herein with the cell. In some embodiments, the cell is in a human subject and the step of contacting is performed by administering to the human subject a therapeutically effective amount of the composition or pharmaceutical composition disclosed herein.

According to one aspect, the disclosure relates to a method of altering a eukaryotic cell comprising: transfecting the eukaryotic cell with a nucleic acid disclosed herein with a gapmer domain sequence sufficiently complementary to a mammalian DUX4 mRNA expressed by the cell such that the DNA gap domain hybridizes to the mRNA target sequence of the eukaryotic cell and degrades the mRNA, thereby reducing expression of the one or plurality of DUX4 mRNA target sequences. According to one aspect, the eukaryotic cell is a mammalian cell. According to one aspect, the nucleic acid disclosed herein comprises from about 6 to about 120 nucleotides. According to one aspect, the nucleic acid disclosed herein comprises from about 10 to about 20 nucleotides. In some embodiments, the nucleic acid sequence comprises about two domains, an LNA domain and a DNA gap domain and each domain is no greater than about 20 nucleotide in length.

According to one aspect, a method of altering a human cell is provided including transfecting the human cell with a nucleic acid disclosed herein with a DNA gap sequence sufficiently complementary to mRNA of the cell such that the DNA gap domain hybridizes to the mRNA target sequence of the human cell and degardes the mRNA, thereby reducing expression of the one or plurality of mRNA target sequences. According to one aspect, the RNA includes between about 10 to about 250 nucleotides. According to one aspect, the RNA includes between about 20 to about 100 nucleotides. The step of transfecting a nucleic acid encoding an RNA may be added to any method disclosed herein so that there is sequential or concurrent transfection of one or a plurality of vectors that carry one or more expressible genes operably linked to a regulatory sequence active in the target cell.

The disclosure also relates to a composition comprising a cell with any one or combination of nucleic acid sequences disclosed herein. In some embodiments, the cell is a plant, insect or mammalian cell. In some embodiments, the cell is a eukaryotic cell or a prokaryotic cell. The cell may be isolated from the body, a component of a culture system, or part of an organism in an in vivo based assay or therapy. The construct(s) containing the nucleic acids can be delivered to a cell using, for example, biolistic bombardment, electrostatic potential or through transformation permeability reagents (reagents known to increase the permeability of the cell wall or cell membrane). Alternatively, the system components can be delivered using Agrobacterium-mediated transformation, insect vectors, grafting, or DNA abrasion, according to methods that are standard in the art, including those described herein. In some embodiments, the system components can be delivered in a viral vector (e.g., a vector from a DNA virus such as, without limitation, geminivirus, AAV, adenovirus, lentiviral strains attenuated for human use, bean yellow dwarf virus, wheat dwarf virus, tomato leaf curl virus, maize streak virus, tobacco leaf curl virus, tomato golden mosaic virus, or Faba bean necrotic yellow virus, or a vector from an RNA virus such as, without limitation, a tobravirus (e.g., tobacco rattle virus, tobacco mosaic virus), potato virus X, or barley stripe mosaic virus.

The disclosure relates to a method of inhibiting DUX4 expression in a subject being treated for muscular dystrophy by administering one or a plurality of nucleic acid sequences to the subject in need thereof in a therapeutically effective amount, the nucleic acid sequence comprising one or a portion of an LNA gapmer or a salt thereof (or a variant at least 70%, 80%, 85%, 90%, 91%, 92%, 93%, 94%, 95%, 96%, 97%, 98% or 99% homologous to an LNA gapmer) in its DNA gap domain. In some embodiments, the DNA gap domain is modified by a glycerol derivative and/or cholesterol. In some embodiments, the nucleic acid sequence comprises a cholesterol molecule on its 3' terminus and is capable of hybridizing to a complementary mRNA in a cell of the subject, thereby preventing Bak1 related apoptosis.

All variants and/or functional fragments that are at least 70%, 80%, 85%, 90%, 91%, 92%, 93%, 94%, 95%, 96%, 97%, 98% or 99% homologous to the sequences of Table 4 are also provided as possible LNA gapmer domains contemplated by the nucleic acid sequences or salts disclosed herein. All variants and/or functional fragments (and salts thereof) that are at least 70%, 80%, 85%, 90%, 91%, 92%, 93%, 94%, 95%, 96%, 97%, 98% or 99% homologous to any sequence that is from about 5 to about 120 nucleotides of modified or unmodified RNA, DNA complementary to mRNA of DUX4 genes are also provided as possible LNA gapmer domains contemplated by the nucleic acid sequences or salts disclosed herein.

The following are representative non-limiting examples of mammalian DUX4 sequences:

```
DUX4 (human): NCBI Reference Sequence: NC_000004.12
                                       (SEQ ID NO: 21)
   1 tgaggtgcac gggagcccgc cggcctctct ctgcccgcgt
     ccgtccgtga aattccggcc 61 ggggctcacc gcgatggccc tcccgacacc ctcggacagc
     accctccccg cggaagcccg 121 gggacgagga cggcgacgga gactcgtttg gaccccgagc
     caaagcgagg ccctgcgagc 181 ctgctttgag cggaacccgt acccgggcat cgccaccaga
     gaacggctgg cccaggccat 241 cggcattccg gagcccaggg tccagatttg gtttcagaat
     gagaggtcac gccagctgag 301 gcagcaccgg cgggaatctc ggccctggcc cgggagacgc
     ggcccgccag aaggccggcg 361 aaagcggacc gccgtcaccg gatcccagac cgccctgctc
     ctccgagcct ttgagaagga 421 tcgctttcca ggcatcgccg cccgggagga gctggccaga
     gagacgggcc tcccggagtc 481 caggattcag atctggttc agaatcgaag ggccaggcac
     ccgggacagg gtgcagggc 541 gcccgcgcag gcaggcggcc tgtgcagcgc ggccccggc
     ggggtcacc ctgctccctc 601 gtgggtcgcc ttcgcccaca ccggcgcgtg gggaacgggg
     cttcccgcac cccacgtgcc
 661 ctgcgcgcct ggggctctcc cacaggggc tttcgtgagc
     caggcagcga gggccgcccc 721 cgcgctgcag cccagccagg ccgcgccggc agaggggatc
     tcccaacctg ccccggcgcg 781 cggggatttc gcctacgccg ccccggctcc tccggacggg
     gcgctctccc accctcaggc 841 tcctcggtgg cctccgcacc cgggcaaaag ccgggaggac
     cgggacccgc agcgcgacgg 901 cctgccgggc cctgcgcgg tggcacagcc tgggcccgct
     caagcggggc cgcagggcca 961 aggggtgctt cgcgccaccca cgtcccaggg gagtccgtgg
     tggggctggg gccggggtcc 1021 ccaggtcgcc ggggcggcgt gggaacccca agccggggca
     gctccacctc cccagcccgc 1081 gccccggac gcctccgcct ccgcgcggca ggggcagatg
     caaggcatcc cggcgccctc 1141 ccaggcgctc caggagccgg cgccctggtc tgcactcccc
     tgcggcctgc tgctggatga 1201 gctcctggcg agcccggagt ttctgcagca ggcgcaacct
     ctcctagaaa cggaggcccc 1261 ggggagctg gaggcctcgg aagaggccgc ctcgctggaa
     gcacccctca gcgaggaaga 1321 ataccgggct ctgctggagg agctttagga cgcggggttg
     ggacggggtc gggtggttcg 1381 gggcaggggcg gtggcctctc tttcgcgggg aacacctggc
     tggctacgga ggggcgtgtc 1441 tccgccccgc ccctccacc gggctgaccg gcctgggatt
     cctgccttct aggtctaggc 1501 ccggtgagag actccactcc gcggagaact gcctttcttt
     cctgggcatc ccggggatcc 1561 cagagccggc ccaggtacca gcaggtgggc cgcctactgc
     gcacgcgcgg gtttgcgggc 1621 agccgcctgg gctgtgggag cagcccgggc agagctctcc
     tgcctctcca ccagcccacc 1681 ccgccgcctg accgcccct cccaccccc acccccacc
     cccggaaaac gcgtcgtccc 1741 ctgggctggg tggagacccc cgtcccgcga aacaccgggc
     ccgcgcagc gtccgggcct 1801 gacaccgctc cggcggctcg cctcctctgc gccccccgc
     caccgtcgcc cgcccgcccg 1861 ggcccctgca gcctcccagc tgccagcacg gagcgcctgg
     cggtcaaaag catacctctg 1921 tctgtctttg cccgcttcct ggctagacct gcgcgcagtg
     cgcaccccgg ctgacgtgca 1981 agggagctcg ctggcctctc tgtgcccttg ttcttccgtg
     aaattctggc tgaatgtctc 2041 cccccacctt ccgacgctgt ctaggcaaac ctggattaga
     gttacatctc ctggatgatt 2101 agttcagaga tatattaaaa tgccccctcc ctgtggatcc
     tatag DUX4 (mouse): NCBI GenBank: AM398151.1
   1 gatcttgaga ttcccaggtg ttcaaggtca tgctgttat
     atggagctcc aagttgatcc
```

```
  61 ttgacccaca ttggaaggag acggtatgtt taccattcta
     caatgatcga caattctaca 121 gagagcctta tggcaggcca gcaggacaaa acaatctctc
     atttgctggc cgtcacctca 181 ggactactta tttgaagtgt ctccagtgtt caaggctaac
     tccagagatc taagagcaca 241 gaacataccg ccagctaaca cagcacatgc aggaagatga
     tcaactcttt tcttcaacct 301 gctccatcga aagtgcacaa cctactggtg tctcaagctt
     ccaggctcct tttcatacag 361 tctgtgaaag aaacaccttg tgaggtgtct ccatctctct
     ctgtctctgt ctatctgtct 421 gtctgtctct gtctctctct ctctccctcc attcctcttt
     tgctccccct cccatttccc 481 tccttgcctc catttcacca tctcttccac tctctgtctc
     catcccatc cttctaccct 541 cccatattca ctccccccat ccactttcta cctccctact
     tccctatctc tctctatcca 601 ttcttcccct ccttctgcac tctgtcactc tctccctacc
     accctccacc ctctgtccct 661 aaatcccttc ccccttctc tccacatctg tgtttgtctc
     tctcttcgtg tcttcctctg 721 cccctaaccc cacccatggt cgtgacttta tcttccctta
     ggatatttgt gagcatgatg 781 tgtgtgtgtt tgtgtgtgtg tgtgtgtgtg tgtgtgtgtg
     tgtgtgtttg tgcttgtgtg 841 tgcccgcatg tgtgcacgtg tttgtgtgtg cgtgtgtgcg
     tgcatgcatg caaatgtgtg 901 tatgtgtgtg tttggtctga gggtgtgcct gttcacaatt
     gtctctgtgt gttgctgcca 961 ggtgcctagg ggctgtttgg attttcattt aatctcagta
     caggtgatgt tccctcttgt 1021 cctcatagca cagtcagact tggaaagtca aggaaggggg
     tctgaaacac tctagagata 1081 ggatggaggt ggtgatgtct ttggatctca gaccatgatg
     ttgggatcgt cagtgtgtgg 1141 tcttgtcttt gtaagctgat tgaatccgga tgggatgaac
     tgagcatggc ttccataggg 1201 cttgggattc ctggaaggct gagtccaatt ccccaagctt
     tactgaagac tgctcccctt 1261 ctcataggtg tcctggaacc tgtgccacct gccagtcaat
     gaatgatttg gctgatggga 1321 atgcgagtc ctctgactct tgtgtgctcc ctgggtgtgg
     gtctagactg gcgaccccgt 1381 ggcttgccag ggatgaggag ccttgggga gattttgctg
     agtgtcagag gacgcttgag 1441 gtccgcctcc tggtgccctg atgtcaggtg ccaggcgtgg
     caggcgtggc gcttcttggc 1501 ggcaccgcga ggaaggggta ggcatgttct gtagcgccta
     actggtaggt agtgggcggg 1561 actacctgag cagaggcaga ggtatttaag gggcagtggt
     cacagccact ctgctggcag 1621 ttgctgcagc ttgtgcttgt tctgaagctg tcctgagtcg
     attctcccaa ggtgaggact 1681 cctgggaggc cgtcattggc accatggcag aagctggcag
     ccctgttggt ggcagtggtg 1741 tggcacggga atcccggcgg cacaggaaga cggtttggca
     ggcctggcaa gagcaggccc 1801 tgctatcaac tttcaagaag aagagatacc tgagcttcaa
     ggagaggaag gagctggcca 1861 agcgaatggg ggtctcagat tgccgcatcc gcgtgtggtt
     tcagaaccgc aggaatcgca 1921 gtggagagga ggggcatgcc tcaaagaggt ccatcagagg
     ctccaggcgg ctagcctcgc 1981 cacagctcca ggaagagctt ggatccaggc cacagggtag
     aggcatgcgc tcatctggca 2041 gaaggcctcg cactcgactc acctcgctac agctcaggat
     cctagggcaa gcctttgaga 2101 ggaacccacg accaggcttt gctaccaggg aggagctggc
     gcgtgacaca gggttgcccg 2161 aggacacgat ccacatatgg tttcaaaacc gaagagctcg
     gcggcgccac aggaggggca 2221 ggcccacagc tcaagatcaa gacttgctgg cgtcacaagg
     gtcggatggg gccctgcag 2281 gtccggaagg cagagagcgt gaaggtgccc aggagaactt
     gttgccacag gaagaagcag 2341 gaagtacggg catggatacc tcgagcccta gcgacttgcc
     ctccttctgc ggagagtccc 2401 agcctttcca agtggcacag ccccgtggag caggccaaca
     agaggccccc actcgagcag 2461 gcaacgcagg ctctctggaa ccccctccttg atcagctgct
     ggatgaagtc caagtagaag 2521 agcctgctcc agcccctctg aatttggatg agaccctgg
     tggcagggtg catgaaggtt 2581 cccaggagag cttttaggcca caggaagaag caggaagtac
     aggcatggat acttctagcc 2641 ccagcgactc aaactccttc tgcagagagt cccagccttc
     ccaagtggca cagccctgtg 2701 gagcgggcca agaagatgcc cgcactcaag cagacagcac
     aggccctctg gaactcctcc 2761 tccttgatca actgctggac gaagtccaaa aggaagagca
     tgtgccagtc ccactggatt 2821 ggggtagaaa tcctggcagc agggagcatg aaggttccca
     ggacagctta ctgccctgg 2881 aggaagcagt aaattcgggc atggatacct cgatccctag
     catctggcca accttctgca 2941 gagaatccca gcctcccaa gtggcacagc cctctggacc
     aggccaagca ccggccccca 3001 ctcaaggtgg aacacggac cccctggagc tcttcctcta
     tcaactgttg gatgaagtcc 3061 aagtagaaga gcatgctcca gcccctctga attgggatgt
     agatcctggt ggcagggtgc 3121 atgaaggttt gtgggagagc ttttggccac aggaagaagc
     aggaagtaca ggcctggata 3181 cttcaagccc cagcgactca aactccttct tcagagagtc
     caagccttcc caagtggcac 3241 agcgccgtgg agcgggccaa gaagatgccc gcactcaagc
     agacagcaca ggccctctgg
```

-continued

```
3301 aactcctcct ctttgatcaa ctgctggacg aagtccaaaa
     ggaagagcat gtgccagccc 3361 cactggattg gggtagaaat cctggcagca tggagcatga
     aggttccag gacagcttac 3421 tgcccctgga ggaagcagca aattcgggca gggatacctc
     gatccctagc atctggccag 3481 ccttctgcag aaaatcccag cctccccaag tggcacagcc
     ctctggacca ggccaagcac 3541 aggccccat tcaaggtggg aacacggacc ccctggagct
     cttccttgat caactgctga 3601 ccgaagtcca acttgaggag caggggcctg cccctgtgaa
     tgtggaggaa acatgggagc 3661 aaatggacac aacacctgat ctgcctctca cttcagaaga
     atatcagact cttctagata 3721 tgctctgact ccccgacagt accccttgct tctagaaacc
     cgagaggcca aagtcctgaa 3781 gagacccgat ttggaactgg agaagggacc catcccagca
     aggatgtgca tcaaaaaccc 3841 aactccagtg acttcccgaa aatgcaaggt gtctcgctaa
     ctataaggat tgattgcagg 3901 tggggataat aatgaagtgc cttctccagg gcccggggat
     taggaaatca gccctgaaag 3961 tgagagagag actctgctac agggacagat ggagaggcca
     atagtgactc ctcaacaaca 4021 aggagcctaa agataacccc aaaagaaggg ccacaccaag
     tgactggctc cagtggaccc 4081 caggaaatca cacgggacac taggactagg cttcactaca
     gaggacacac actccctgag 4141 ggcaatgggg agagtggact ccttccctgg cttatatgga
     ctgctgttat ccttacagat 4201 gcttcatgca gagctgtgca aggttttaca ggccagtctt
     ttaatatcta ctacccatag 4261 gtctttgtt tgttttcttt ttcttttca ctttcttttt
     cattttttt tctttttctt 4321 tttttaggg gtgggttggc tttgttgggt ttggtttggt
     tttgtgtagt ttgtttccat 4381 tgctttcaat aaactttatt gattttaaca aaatttgttc
     gtgtgtttgt gtgctgtttt 4441 gtgggatgag gggtgggttg aataggctgt tttgttctac
     ccggagaaag tgcatgagaa 4501 ttc
```

DUX4 (gorilla): NCBI Reference
Sequence: NC_018428.2

```
  1 ctggctgcac ctgccgcagt gcacaggccg gctgaggtgc
    acgggagccc gccggcctct 61 ctctgcccgc gtccgtccgt gacattccgg ccggggctca
    ccgcgatggc cctcccgaca 121 ccttcggaca gcaccctccc cgcggaagcc cggggacgag
    gacggcgacg gagactcgtt 181 tggaccccga gccaaagcga ggccctgcga gcctgctttg
    agcggaaccc gtaccgggc 241 atcgccacca gagaacggct ggcccaggcc atcggcattc
    cggagcccag ggtccagatt
```

```
301 tggtttcaga atgagaggtc acgccagctg aggcagcacc
    ggcgggaatc tcggccctgg 361 cccgggagac gcggcccgcc agaaggccgg cgaaagcgga
    ccgccgtcac cggatcccag 421 accgccctgc tcctccgagc ctttgagaag gatcgttttc
    caggcatcgc cgcccgggaa 481 gagctggcca gagagacggg cctcccggag tccaggattc
    agatctggtt tcagaatcga 541 agggccaggc acccgggaca gggtggcagg gcgcccgcgc
    aggcaggcgg cctgtgcaac 601 gcggcccccg gcgggtgtca ccctgctccc tcgtgggtcg
    ccttcgccca caccggcgcg 661 tggggaaegg ggcttcccgc accccacgtg ccctgcgcgc
    ctggggctct cccacagggg 721 gcttccgtga gccaggcggc gagggccgcc cccgtgctgc
    agcccagccg ggccgcgccg 781 gcggaggga tc
```

Kits

In some embodiments, kits in accordance with the present disclosure may be used to treat or prevent development of a dystrophin-related disorder in a subject. In some embodiments, the kits comprise a container comprising one or a plurality of pharmaceutical compositions comprising the nucleic acids, compositions described herein and, optionally, a device used to administer the one or more pharmaceutical compositions. Any nucleic acid, composition, or component thereof disclosed may be arranged in a kit either individually or in combination with any other nucleic acid, composition, or component thereof. The disclosure provides a kit to perform any of the methods described herein. In some embodiments, the kit comprises at least one container comprising a therapeutically effective amount of one or a plurality of oligonucleotides comprising a DNA gap domain capable of targeting a targeting domain on a cell of a subject. In some embodiments, the kit comprises at least one container comprising any of the nucleotide sequences or functional fragments described herein. In some embodiments, the nucleotide sequences are in solution (such as a buffer with adequate pH and/or other necessary additive to minimize degradation of the nucleotide sequences during prolonged storage). In some embodiments, the oligonucleotides are lyophilized for the purposes of resuspension after prolonged storage. In some embodiments, the kit comprises: at least one container comprising one or a plurality of oligonucleotides comprising nucleotide sequences or functional fragments disclosed herein. In some embodiments, the kit optionally comprises instructions to perform any or all steps of any method described herein.

The kit may contain two or more containers, packs, or dispensers together with instructions for preparation of an array. In some embodiments, the kit comprises at least one container comprising the oligonucleotides described herein and a second container comprising a means for maintenance, use, and/or storage of the oligonucleotides such as storage buffer. In some embodiments, the kit comprises a composition comprising any oligonucleotide disclosed herein in solution or lyophilized or dried and accompanied by a rehydration mixture. In some embodiments, the oligonucleotides and rehydration mixture may be in one or more additional containers.

The compositions included in the kit may be supplied in containers of any sort such that the shelf-life of the different components are preserved, and are not adsorbed or altered by the materials of the container. For example, suitable containers include simple bottles that may be fabricated from glass, organic polymers, such as polycarbonate, polystyrene, polypropylene, polyethylene, ceramic, metal or any other material typically employed to hold reagents or food; envelopes, that may consist of foil-lined interiors, such as aluminum or an alloy. Other containers include test tubes, vials, flasks, and syringes. The containers may have two compartments that are separated by a readily removable membrane that upon removal permits the components of the compositions to mix. Removable membranes may be glass, plastic, rubber, or other inert material.

Kits may also be supplied with instructional materials. Instructions may be printed on paper or other substrates, and/or may be supplied as an electronic-readable medium, such as a floppy disc, CD-ROM, DVD-ROM, zip disc, videotape, audio tape, or other readable memory storage device. Detailed instructions may not be physically associated with the kit; instead, a user may be directed to an internet web site specified by the manufacturer or distributor of the kit, or supplied as electronic mail.

The disclosure also provides a kit comprising: a nucleic acid sequence disclosed herein; and a vector comprising one or plurality of nucleic acid sequences disclosed herein and a syringe and/or needle. In some embodiments, the kit further comprises at least one of the following: one or a plurality of eukaryotic cells comprising regulatory protein capable of trans-activation of the regulatory element, cell growth media, a volume of fluorescent stain or dye, and a set of instructions, optionally accessible remotely through an electronic medium.

Any and all journal articles, patent applications, issued patents, or other cited references disclosed herein are incorporated by reference in their respective entireties.

REFERENCES

1. Agrawal, S., & Iyer, R. P. (1995). Modified oligonucleotides as therapeutic and diagnostic agents. *Curr Opin Biotechnol*, 6(1), 12-19.
2. Almeida, M., et al. (2011). Glucocorticoids and tumor necrosis factor alpha increase oxidative stress and suppress Wnt protein signaling in osteoblasts. *J Biol Chem*, 286(52), 44326-44335.
3. Amato, A. A., & Brown, R. H. (2015). Muscular Dystrophies and Other Muscle Diseases. Clinicalgate, http://clinicalgate.com/muscular-dystrophies-and-other-muscle-diseases/
4. Aoki, Y., et al. (2013). Highly efficient in vivo delivery of PMO into regenerating myotubes and rescue in laminin-alpha 2 chain-null congenital muscular dystrophy mice. *Hum Mol Genet*, 22(24), 4914-4928.
5. Barakat-Haddad, C., et al. (2016). A systemic review of risk factors associated with muscular dystrophies. *NeuroToxicology*, http://dx.doi.org/10.1016/j.neuro.2016.03.007
6. Bharathy, N., Ling, B. & Taneja, R. (2013). Epigenetic Regulation of Skeletal Muscle Development and Differentiation. In Kundu R. K. (Ed.) *Epigenetics: Development and Disease* (pp. 139-145). New York: Springer
7. Bickmore, W. A., & van der Maarel, S. M. (2003). Perturbations of chromatin structure in human genetic disease: recent advances. *Hum Mol Genet*, 12 Spec No 2, R207-213. doi: 10.1093/hmg/ddg260
8. Bindoff, L. A., et al. (2006). Severe faciscapulohumeral muscular dystrophy presenting with Coats' disease and mental retardation. *Neuromuscul Disord*, 16(9-10), 559-563.
9. Bird, T. D. (1999). Myotonic Dystrophy Type 1. [Updated 2015 Oct. 22]. In: Pagon R A, Adam M P, Ardinger H H, et al., editors. GeneReviews® [Internet].
10. Blauwkamp, T. A., et al. (2012). Endogenous Wnt signalling in human embryonic stem cells generates an equilibrium of distinct lineage-specified progenitors. *Nat Commun*, 3, 1070.
11. Block, G. J., et al. (2013). Wnt/beta-catenin signaling suppresses DUX4 expression and prevents apoptosis of FSHD muscle cells. *Hum Mol Genet*, 22(23), 4661-4672.
12. Bodine, S. C., & Baehr, L. M. (2014). Skeletal muscle atrophy and the E3 ubiquitin ligases MuRF1 and MAFbx/atrogin-1. *Am J Physiol Endocrinol Metab*, 307(6), E469-484.
13. Bodine, S. C., et al. (2001). Identification of ubiquitin ligases required for skeletal muscle atrophy. *Science*, 294(5547), 1704-1708. doi: 10.1126/science.1065874
14. Bonne, G., et al. (2004). Emery-Dreifuss Muscular DystrophyIn: Pagon, R. A., Bird, T. D., Dolan, C. R. (Eds.), University of Washington, Seattle (Wash.). (September 29 [Updated 2013 Jan. 17] GeneReviews™ [Internet]) http://www.ncbi.nlm.nih.gov/books/NBK1436/.
15. Braasch, D. A., & Corey, D. R. (2001). Locked nucleic acid (LNA): fine-tuning the recognition of DNA and RNA. *Chem Biol*, 8(1), 1-7.
16. Brais, B., et al. (1999). Oculopharyngeal muscular dystrophy. *Seminars in Neurology*, 19, 59-66.
17. Campbell, J. M., Bacon, T. A., & Wickstrom, E. (1990). Oligodeoxynucleoside phosphorothioate stability in subcellular extracts, culture media, sera and cerebrospinal fluid. *J Biochem Biophys Methods*, 20(3), 259-267.
18. Caruso, N., et al. (2013). Deregulation of the protocadherin gene FAT1 alters muscle shapes: implications for the pathogenesis of facioscapulohumeral dystrophy. *PLoS Genet*, 9(6), e1003550. doi: 10.1371/journal.pgen.1003550
19. Centner, T., et al. (2001). Identification of muscle specific ring finger proteins as potential regulators of the titin kinase domain. *J Mol Biol*, 306(4), 717-726.
20. Chin, M. H., et al. (2009). Induced pluripotent stem cells and embryonic stem cells are distinguished by gene expression signatures. *Cell Stem Cell*, 5(1), 111-123.
21. Chung, T. L., et al. (2010). Ascorbate Promotes Epigenetic Activation of CD30 in Human Embryonic Stem Cells. *Stem Cells*, 28, 1782-1793. doi: 10.1002/stem.500
22. Civas, A., et al. (2002). Regulation of virus-induced interferon-A genes. *Biochimie*, 84(7), 643-654.
23. Dai, K. S., & Liew, C. C. (2001). A novel human striated muscle RING zinc finger protein, SMRZ, interacts with SMT3b via its RING domain. *J Biol Chem*, 276(26), 23992-23999.
24. Dalton, J. C., Ranum, L. P. W. & Day, J. W. (2006). Myotonic Dystrophy Type 2. [Updated 2013 Jul. 3]. In: Pagon R A, Adam M P, Ardinger H H, et al., editors. GeneReviews® [Internet]. Seattle (Wash.): University of Washington, Seattle; 1993-2016.
25. Dandapat, A., et al. (2014). Dominant lethal pathologies in male mice engineered to contain an X-linked DUX4 transgene. *Cell Rep*, 8(5), 1484-1496. doi: 10.1016/j.celrep.2014.07.056
26. Darty, K., Denise, A., & Ponty, Y. (2009). VRNA: interactive drawing and editing of the RNA secondary structure. *Bioinformatics*, 25(15), 1974-1975.

27. de Greef, J. C., et al. (2010). Clinical features of facioscapulohumeral muscular dystrophy 2. *Neurology,* 75(17), 1548-1554. doi: 10.1212/WNL.0b013e3181f96175
28. de Palma, L., et al. (2008). Ubiquitin ligases MuRF1 and MAFbx in human skeletal muscle atrophy. *Joint Bone Spine,* 75(1), 53-57. doi: 10.1016/j.jbspin.2007.04.019
29. Deenen, J. C., et al. (2014). Population-based incidence and prevalence of facioscapulohumeral dystrophy. *Neurology,* 83(12), 1056-1059.
30. Dixit, M., et al. (2007). DUX4, a candidate gene of facioscapulohumeral muscular dystrophy, encodes a transcriptional activator of PITX1. *Proc Natl Acad Sci USA,* 104(46), 18157-18162. doi: 10.1073/pnas.0708659104
31. Du, L., & Gatti, R. A. (2009). Progress toward therapy with antisense-mediated splicing modulation. *Curr Opin Mol Ther,* 11(2), 116-123.
32. Echigoya, Y., et al. (2015). Long-term efficacy of systemic multiexon skipping targeting dystrophin exons 45-55 with a cocktail of vivo-morpholinos in mdx52 mice. *Mol Ther Nucleic Acids,* 4, e225. doi: 10.1038/mtna.2014.76
33. Elmen, J., et al. (2004). Locked nucleic acid containing antisense oligonucleotides enhance inhibition of HIV-1 genome dimerization and inhibit virus replication. *FEBS Lett,* 578(3), 285-290. doi: 10.1016/j.febslet.2004.11.015
34. Emery, A. E. (1991). Population frequencies of inherited neuromuscular diseases: a world survey. *Neuromuscul. Disord,* 1(1), 19-29.
35. Emery, A. E. (2000). Emery-Dreifuss muscular dystrophy—a 40 year retroscpective. *Neuromuscul. Disord.,* 10 (4-5), 228-232,
36. Ferreboeuf, M., et al. (2014). DUX4 and DUX4 downstream target genes are expressed in fetal FSHD muscles. *Hum Mol Genet,* 23(1), 171-181. doi: 10.1093/hmg/ddt409
37. Frieden, M., et al. (2003). Expanding the design horizon of antisense oligonucleotides with alpha-L-LNA. *Nucleic Acids Res,* 31(21), 6365-6372.
38. Gabellini, D., et al. (2006). Facioscapulohumeral muscular dystrophy in mice overexpressing FRG1. *Nature,* 439(7079), 973-977. doi: 10.1038/nature04422
39. Gabriels, J., et al. (1999). Nucleotide sequence of the partially deleted D4Z4 locus in a patient with FSHD identifies a putative gene within each 3.3 kb element. *Gene,* 236(1), 25-32.
40. Geng, L. N., et al. (2012). DUX4 activates germline genes, retroelements, and immune mediators: implications for facioscapulohumeral dystrophy. *Dev Cell,* 22(1), 38-51.
41. Giorgino, F., & Smith, R. J. (1995). Dexamethasone enhances insulin-like growth factor-I effects on skeletal muscle cell proliferation. Role of specific intracellular signaling pathways. *J Clin Invest,* 96(3), 1473-1483. doi: 10.1172/JCI118184
42. Harper, P. (2001). Myotonic dystrophy, 3rd edn. London: W B Saunders.
43. Hewitt, J. E., et al. (1994). Analysis of the tandem repeat locus D4Z4 associated with facioscapulohumeral muscular dystrophy. *Hum Mol Genet,* 3(8), 1287-1295.
44. Hoffman, E. P., Brown, R. H., Kunkel, L. M. (1987). Dystrophin: the protein product of the Duchenne muscular dystrophy locus. *Cell,* 51(6), 919-928.
45. Hu, X., et al. (2013). Dexamethasone alters epithelium proliferation and survival and suppresses Wnt/beta-catenin signaling in developing cleft palate. *Food Chem Toxicol,* 56, 67-74.
46. Jabbari, H., & Codon A. (2014), A fast and robust iterative algorithm for prediction of RNA pseudoknotted secondary structures. *BMC Bioinformatics,* 15(147).
47. Jalali Tehrani, H., et al. (2014). Effect of dexamethasone, insulin and EGF on the myogenic potential on human endometrial stem cell. *Iran J Pharm Res,* 13(2), 659-664.
48. Jones, T. I., et al. (2012). Facioscapulohumeral muscular dystrophy family studies of DUX4 expression: evidence for disease modifiers and a quantitative model of pathogenesis. *Hum Mol Genet,* 21(20), 4419-4430. doi: 10.1093/hmg/dds284
49. Jones, T. I., et al. (2014). Identifying diagnostic DNA methylation profiles for facioscapulohumeral muscular dystrophy in blood and saliva using bisulfite sequencing. *Clin Epigenetics,* 6(1), 23. doi: 10.1186/1868-7083-6-23
50. Kauppinen, S., Vester, B., & Wengel, J. (2005). Locked nucleic acid (LNA): High affinity targeting of RNA for diagnostics and therapeutics. *Drug Discov Today Technol,* 2(3), 287-290. doi: 10.1016/j.ddtec.2005.08.012
51. Koenig, M., et al. (1987) Complete cloning of the Duchenne muscular dystrophy (DMD) cDNA and preliminary genomic organization of the DMD gene in normal and affected individuals. *Cell,* 50(3), 509-17.
52. Koivisto, H., et al. (2004). Cultures of human embryonic stem cells: serum replacement medium or serum-containing media and the effect of basic fibroblast growth factor. *Reprod Biomed Online,* 9(3), 330-337.
53. Krom, Y. D., et al. (2013). Intrinsic epigenetic regulation of the D4Z4 macrosatellite repeat in a transgenic mouse model for FSHD. *PLoS Genet,* 9(4), e1003415.
54. Kurreck, J., et al. (2002). Design of antisense oligonucleotides stabilized by locked nucleic acids. *Nucleic Acids Res,* 30(9), 1911-1918.
55. Laishes, B. A., & Williams, G. M. (1976). Conditions affecting primary cell cultures of functional adult rat hepatocytes. II. Dexamethasone enhanced longevity and maintenance of morphology. *In Vitro,* 12(12), 821-832.
56. Lamonerie, T., et al. (1996). Ptx1, a bicoid-related homeo box transcription factor involved in transcription of the pro-opiomelanocortin gene. *Genes Dev,* 10(10), 1284-1295.
57. Lanctot, C., Lamolet, B., & Drouin, J. (1997). The bicoid-related homeoprotein Ptx1 defines the most anterior domain of the embryo and differentiates posterior from anterior lateral mesoderm. *Development,* 124(14), 2807-2817.
58. Lanctot, C., Moreau, A., Chamberland, M., Tremblay, M. L., & Drouin, J. (1999). Hindlimb patterning and mandible development require the Ptx1 gene. (vol 126, pg 1805, 1999). *Development,* 126(15), U5-U5.
59. Landouzy, L., & Dejerine, J. (1884). De la myopathie atrophique progressive (myopathie héréditaire, débutant dans l'enfance par la face, sans alteration du système nerveux). *Comptes rendus de l'Académie des sciences* 98: 53-55.
60. Landouzy, L., & Dejerine, J. Contribution à l'étude de la myopathie atrophique progressive (myopathie atrophique progressive, à type scapulo-huméral). *Comptes rendus de la Société de biologie* 38: 478-481.
61. Lee, J. E., Bennett, C. F., & Cooper, T. A. (2012). RNase H-mediated degradation of toxic RNA in myotonic dystrophy type 1. *Proc Natl Acad Sci USA,* 109(11), 4221-4226.
62. Lee, J. J., & Yokota, T. (2013). Antisense therapy in neurology. *J Pers Med,* 3(3), 144-176.

63. Leidenroth, A., & Hewitt, J. E. (2010). A family history of DUX4: phylogenetic analysis of DUXA, B, C and Duxbl reveals the ancestral DUX gene. *BMC Evol Biol*, 10, 364.
64. Lek, A., Rahimov, F., Jones, P. L., & Kunkel, L. M. (2015). Emerging preclinical animal models for FSHD. *Trends Mol Med*, 21(5), 295-306. doi: 10.1016/j.molmed.2015.02.011
65. Lemmers, R. J., et al. (2012). Digenic inheritance of an SMCHD1 mutation and an FSHD-permissive D4Z4 allele causes facioscapulohumeral muscular dystrophy type 2. *Nat Genet*, 44(12), 1370-1374. doi: 10.1038/ng.2454
66. Lemmers, R. J., et al. (2010). A unifying genetic model for facioscapulohumeral muscular dystrophy. *Science*, 329(5999), 1650-1653. doi: 10.1126/science.1189044
67. Lemmers, R. J., et al.(2004). Mechanism and timing of mitotic rearrangements in the subtelomeric D4Z4 repeat involved in facioscapulohumeral muscular dystrophy. *Am J Hum Genet*, 75, 44-53.
68. Lunt, P. W. (1998). 44th ENMC International Workshop: Facioscapulohumeral Muscular Dystrophy: Molecular Studies 19-21 July 1996, Naarden, The Netherlands. *Neuromuscul Disord*, 8(2), 126-130.
69. Koshkin, A. A., et al. (1998). LNA (Locked Nucleic Acids): Synthesis of the adenine, cytosine, guanine, 5-methylcytosine, thymine and uracil bicyclonucleoside monomers, oligomerisation, and upreceptened nucleic acid recognition. *Tetrahedron*, 54(14), 3607-3630.
70. Mamchaoui, K., et al. (2011). Immortalized pathological human myoblasts: towards a universal tool for the study of neuromuscular disorders. *Skelet Muscle*, 1, 34.
71. Marcil, A., et al. (2003). Pitx1 and Pitx2 are required for development of hindlimb buds. *Development*, 130(1), 45-55. doi: 10.1242/dev.00192
72. Marsollier, A. C., et al. (2016). Antisense targeting of 3' end elements involved in DUX4 mRNA processing is an efficient therapeutic strategy for facioscapulohumeral dystrophy: a new gene-silencing approach. *Hum Mol Genet*, 25(8), 1468-1478. doi: 10.1093/hmg/ddw015
73. Marusin, A. V., et al. (2016). Haplotype analaysis of oculopharyngeal muscular dystrophy (OPMD) locus in Yakutia. *Russ J Genet*, 52 (3): 331-338. doi:10.1134/S1022795416030091
74. McElhinny, A. S., et al. (2002). Muscle-specific RING finger-1 interacts with titin to regulate sarcomeric M-line and thick filament structure and may have nuclear functions via its interaction with glucocorticoid modulatory element binding protein-1. *J Cell Biol*, 157(1), 125-136. doi: 10.1083/jcb.200108089
75. Milner-Brown, H. S., & Miller, R. G. (1988). Muscle strengthening through high-resistance weight training in patients with neuromuscular disorders. *Arch Phys Med Rehabil*, 69(1), 14-19.
76. Mitsuhashi, H., et al. (2013). Expression of DUX4 in zebrafish development recapitulates facioscapulohumeral muscular dystrophy. *Hum Mol Genet*, 22(3), 568-577.
77. Mostacciuolo, M. L., et al. (2009). Facioscapulohumeral muscular dystrophy: epidemiological and molecular study in a north-east Italian population sample. *Clin Genet*, 75(6), 550-555.
78. Munsie, L. N., Desmond, C. R. & Truant, R. (2012). Cofilin nuclear-cytoplasmic shuttling affects cofilin-actin rod formation during stress. *Cell Science*, 125, 3977-3988.
79. Muntoni, F., & Wood, M. J. (2011). Targeting RNA to treat neuromuscular disease. *Nat Rev Drug Discov*, 10(8), 621-637. doi: 10.10381nrd3459
80. Nielsen, K. E., et al. (2004). NMR studies of fully modified locked nucleic acid (LNA) hybrids: solution structure of an LNA:RNA hybrid and characterization of an LNA:DNA hybrid. *Bioconjug Chem*, 15(3), 449-457. doi: 10.1021/bc034145h
81. Padberg, G. W. (1982). Facioscapulohumeral Disease [these], Leiden, the Netherlands.
82. Padberg, G. W., et al. (1995). Facioscapulohumeral muscular dystrophy in the Dutch population. *Muscle Nerve*, 2, S81-S84.
83. Pan, C., et al. (2009). Comparative proteomic phenotyping of cell lines and primary cells to assess preservation of cell type-specific functions. *Mol Cell Proteomics*, 8(3), 443-450.
84. Pandey, S. N., et al. (2012). Conditional over-expression of PITX1 causes skeletal muscle dystrophy in mice. *Biol Open*, 1(7), 629-639.
85. Pandey, S. N., et al. (2014). Morpholino treatment improves muscle function and pathology of Pitx1 transgenic mice. *Mol Ther*, 22(2), 390-396.
86. Pandey, S. N., Khawaja, H., & Chen, Y. W. (2015). Culture Conditions Affect Expression of DUX4 in FSHD Myoblasts. *Molecules*, 20(5), 8304-8315. doi: 10.3390/molecules20058304
87. Pegoraro, E., Hoffman, E. P. (2000). Limb-girdle muscular dystrophy overview. [updated 2012 Aug. 30]. In: Pagon R. A., Bird, T. D., Dolan, C. R., et al. (eds.). GeneReviews™ [Internet]. Seattle (Wash.): University of Washington, Seattle; 1993.
88. Ramellia, G. P., et al. (2006). Becker muscular dystrophy with marked divergence between clinical and molecular genetic findings: case series. *Swiss Med*, 136, 189-193.
89. Sbiti, A., El Kerch, F. & Sefiani, A. (2002). Analysis of Dystrophin gene deletions by multiplex PCR in Moroccan patients. *Biomed. Biotechnol*, 2 (3), 158-160.
90. Skottman, H., et al. (2006). Unique gene expression signature by human embryonic stem cells cultured under serum-free conditions correlates with their enhanced and prolonged growth in an undifferentiated stage. *Stem Cells*, 24(1), 151-167.
91. Snider, L., et al. (2009). RNA transcripts, miRNA-sized fragments and proteins produced from D4Z4 units: new candidates for the pathophysiology of facioscapulohumeral dystrophy. *Hum. Mol. Genet*, 18(13), 2414-2430, doi: 10.1093/hmg/ddp180
92. Snider, L., et al. (2010). Facioscapulohumeral dystrophy: incomplete suppression of a retrotransposed gene. *PLoS Genet*, 6(10), e1001181. doi: 10.1371/journal.pgen.1001181
93. Stadler, G., et al. (2013). Telomere position effect regulates DUX4 in human facioscapulohumeral muscular dystrophy. *Nat Struct Mol Biol*, 20(6), 671-678.
94. Summerton, J., & Weller, D. (1997). Morpholino antisense oligomers: design, preparation, and properties. *Antisense Nucleic Acid Drug Dev*, 7(3), 187-195.
95. Tassin, A., et al. (2013). DUX4 expression in FSHD muscle cells: how could such a rare protein cause a myopathy? *J Cell Mol Med*, 17(1), 76-89.
96. Tawil, R., et al. (1996). Evidence for anticipation and association of deletion size with severity in facioscapulohumeral muscular dystrophy. The FSH-DY Group. *Ann Neurol*, 39, 744-748.
97. Tawil, R., et al. (2015). Evidence-based guideline summary: Evaluation, diagnosis, and management of facioscapulohumeral muscular dystrophy: Report of the Guideline Development, Dissemination, and Implementation Subcommittee of the American Academy of Neurology and the Practice Issues Review Panel of the American Association of Neuromuscular & Electrodiagnostic Medicine. Neurology, 85(4), 357-364.

98. Tehrani, H. J., et al. (2014). Effect of Dexamethasone, Insulin and EGF on the Myogenic Potential on Human Endometrial Stem Cell, *Iranian Journal of Pharmaceutical Research,* 13(2), 659-664.
99. Torchilin, V. P. (2006). Recent approaches to intracellular delivery of drugs and DNA and organelle targeting. *Annu Rev Biomed Eng,* 8, 343-375.
100. Touznik, A., Lee, J. J., & Yokota, T. (2014). New developments in exon skipping and splice modulation therapies for neuromuscular diseases. *Expert Opin Biol Ther,* 14(6), 809-819.
101. Upadhyaya, M., et al. (1997). Improved molecular diagnosis of facioscapulohumeral muscular dystrophy (FSHD): validation of the differential double digestion for FSHD. *J Med Genet,* 34(6), 476-479.
102. Urtasun, M., et al. (1998). Limb-girdle muscular dystrophy in guipuzcoa. *Brain,* 121, 1735-1747.
103. van der Kooi, A. J., et al. (1996). The clinical spectrum of limb girdle muscular dystrophy. A survey in the Netherlands. *Brain,* 119, 1471-1480.
104. van der Maarel, S. M., et al. (2000). De novo facioscapulohumeral muscular dystrophy: frequent somatic mosaicism, sex-dependent phenotype, and the role of mitotic transchromosomal repeat interaction between chromosomes 4 and 10. *Am J Hum Genet,* 66(1), 26-35. doi: 10.1086/302730
105. van Geel, M., et al. (2002). Genomic analysis of human chromosome 10q and 4q telomeres suggests a common origin. *Genomics,* 79(2), 210-217. doi: 10.1006/geno.2002.6690
106. van Overveld, P. G., et al. (2005). Variable hypomethylation of D4Z4 in facioscapulohumeral muscular dystrophy. *Ann Neurol,* 58(4), 569-576.
107. van Overveld, P. G., et al. (2003). Hypomethylation of D4Z4 in 4q-linked and non-4q-linked facioscapulohumeral muscular dystrophy. *Nat Genet,* 35(4), 315-317.
108. Vanderplanck, C., et al. (2011). The FSHD atrophic myotube phenotype is caused by DUX4 expression. *PLoS One,* 6(10), e26820. doi: 10.1371/journal.pone.0026820
109. Vie, M. P., et al. (1997). Purification, molecular cloning, and functional expression of the human nicotinamide-adenine dinucleotide phosphate-regulated thyroid hormone-binding protein. *Mol Endocrinol,* 11(11), 1728-1736. doi: 10.1210/mend.11.11.9915
110. Voit, T. (2001). Congenital muscular dystrophies. In Karpati, G., Hilton-Jones, D., Griggs, R. C. (Ed.). *Disorders of Voluntary Muscle.* 7th ed. (pp.503-524). Cambridge, UK: Press Syndicate of the University of Cambridge.
111. Wallace, L. M., et al. (2011). DUX4, a candidate gene for facioscapulohumeral muscular dystrophy, causes p53-dependent myopathy in vivo. *Ann Neurol,* 69(3), 540-552.
112. Wang C H, et al. (2010). International Standard of Care Committee for Congenital Muscular Dystrophy. Consensus statement on standard of care for congenital muscular dystrophies. *J Child Neurol,* 25, 1559-1581.
113. Wang, M. X., et al. (2014). Evaluation of Tris[2-(Acryloyloxy) Ethyl]Isocyanurate Cross-Linked Polyethylenimine as Antisense Morpholino Oligomer Delivery Vehicle in Cell Culture and Dystrophic mdx Mice. *Hum Gene Ther,* 25(5), 419-427.
114. Wijmenga, C., et al. (1990). Location of facioscapulohumeral muscular dystrophy gene on chromosome 4. *Lancet,* 336(8716), 651-653.
115. Wijmenga, C., et al. (1992). Chromosome 4q DNA rearrangements associated with facioscapulohumeral muscular dystrophy. *Nat Genet,* 2(1), 26-30. doi: 10.1038/ng0992-26
116. Wijmenga, C., et al. (1991). Mapping of facioscapulohumeral muscular dystrophy gene to chromosome 4q35-qter by multipoint linkage analysis and in situ hybridization. *Genomics,* 9(4), 570-575.
117. Wohlgemuth, M., et al. (2004). Ventilatory support in facioscapulohumeral muscular dystrophy. *Neurology,* 63(1), 176-178.
118. Yamada, T., et al. (1993). Control of cell pattern in the neural tube: motor neuron induction by diffusible factors from notochord and floor plate. *Cell,* 73(4), 673-686.
119. Yokota, T., Hoffman, E., & Takeda, S. (2011). Antisense oligo-mediated multiple exon skipping in a dog model of duchenne muscular dystrophy. *Methods Mol Biol,* 709, 299-312.
120. Zamecnik, P. C., & Stephenson, M. L. (1978). Inhibition of Rous sarcoma virus replication and cell transformation by a specific oligodeoxynucleotide. *Proc Natl Acad Sci USA,* 75(1), 280-284.
121. Zatz, M., et al. (1995). High proportion of new mutations and possible anticipation in Brazilian facioscapulohumeral muscular dystrophy families. *Am J Hum Genet,* 56, 99-105.
122. Zhang, Y., et al. (2014). Human skeletal muscle xenograft as a new preclinical model for muscle disorders. *Hum Mol Genet,* 23(12), 3180-3188. doi: 10.1093/hmg/ddu028
123. Zhang, Y., et al. (2016). DNA-binding sequence specificity of DUX4. *Skeletal Muscle,* 6(8).

EXAMPLES

Example 1

Human Myoblasts Cell Lines and Stock Management

The patient myoblast cell line was derived from a patient with FSHD with 2 D4Z4 units from a 27-year-old male, termed KM186. The control myoblasts were derived from the semitendinosus muscle of a 41-year-old male, termed KM155. More specifically, KM155 control myoblasts were derived from a healthy unaffected individual confirmed without the FSHD genotype. The second set of immortalized myoblasts was derived from a biceps biopsy of a 66-year-old man with FSHD, termed 15ABic, with 8 D4Z4 units. The control myoblasts were derived from a biceps biopsy of the 60-year-old sister of the patient, termed 15VBic. More specifically, 15VBic control myoblasts were derived from a healthy unaffected individual confirmed without the FSHD genotype. All immortalized human myoblast cell lines used for the purpose of this project were immortalized as previously reported (Mamchaoui et al, 2011). In brief, cyclin-dependent kinase 4 (CDK4) and human telomerase reverse transcriptase (hTERT) cDNA were inserted into pBabe vectors containing neomycin- and hygromycin-resistance genes.

Once cell lines KM186, KM155, 15Abic and 15Vbic had reached 80% confluency, cells were frozen at a concentration of approximately 3.5×10$^6$ cells/mL in 1 mL of Recovery™ Cell Culture Freezing Media (Gibco). Stock vials were frozen in a Nalgene™ Cryo Freezing Container (Thermo Fisher Scientific), overnight at −80° C. 24 hours after freezing at −80° C., all stock vials were moved into liquid nitrogen (−196° C.), for long-term storage.

cDNA Synthesis and RT-PCR

Total RNA from non-treated (NT) KM186 myotubes, NT KM155 myotubes, NT 15Abic myotubes, NT 15Bbic myotubes, treated 15Abic myotubes and treated 15Vbic myotubes, were extracted using TRIzol Reagent (Life Technologies) according to manufacturer's protocol. In brief, spent media was aspirated, and 1 mL of TRIzol reagent was added to each well in a 12-well plate. Each well was rinsed 10 times with TRIzol to ensure detachment of all cells, followed by collection of the 1 mL of TRIzol containing cells. All collected samples were stored on ice, vortexed for 15 seconds at maximum speed and then stored at −80° C. until further use. When ready for use, all samples were thawed on ice for 15 minutes; once thawed 200, µL of chloroform was added to each sample. Samples were mixed by shaking vigorously for 15 seconds, followed by incubation at room temperature for 2 minutes. All samples were then spun down at 12,000 g for 15 minutes at 4° C. After centrifugation, three layers including the RNA layer (top), DNA layer (middle), and protein layer (bottom) were visible. The bottom protein layer was removed and all samples were spun down at 12,000 g for 15 minutes at 4° C. The top RNA layer (clear aqueous phase) was then transferred into a new tube and 500 µL of molecular grade isopropanol and 1 µL of RNA grade glycogen (Thermo Scientific) was added to the aqueous solution. Each sample was then vortexed for 15 seconds and incubated for 10 minutes at room temperature. Following incubation, the samples were centrifuged at 12,000 g for 10 minutes at 4° C. The supernatant within each sample was removed, and 1 mL of 75% ethanol was used to wash the RNA pellet. The samples were then spun down at 7500 g for 5 minutes at 4° C. All ethanol was decanted carefully and the RNA pellet was left to dry for 5 minutes. Once the RNA pellet was dry and any remaining ethanol had evaporated, the pellet was resuspended in 35 µL of UltraPure™ RNase/DNase-free distilled water (Invitrogen) and heated at 65° C. for 10 minutes. RNA concentrations were measured using a NanoDrop LITE spectrometer (Thermo Fisher Scientific) and samples were stored at −80° C.

Reverse transcription was performed using two different methods. First, the SuperScript III One-Step RT-PCR System with Platinum Taq DNA Polymerase (Thermo Fisher Scientific) was used. In a 0.2-mL tube, 12.5 µL of 2× Reaction Mix, 0.5 µL of forward DUX4 primer 5'-CCCAGGTACCAGCAGACC-3' (SEQ ID NO: 31), 0.5 µL of reverse DUX4 primer 5'-TCCAGGAGATGTAACTCTAATCCA-3' (SEQ ID NO: 32), 1.0 µL of SuperScript® III Taq polymerase, 4.5 µL of UltraPure RNase/DNase-free distilled water, and 5 µL of RNA sample at a concentration of 50 ng/µL were combined, gently mixed by centrifuging and incubated using the thermocycler conditions listed in Table 3.

The second type of reverse transcription was performed using SuperScript III RT (Life Technologies) and GoTaq® G2 green master mix (Promega). Briefly, first strand cDNA synthesis was carried out by incubating RNA samples at 65° C. for 5 min with 1 µL oligo(dT) (Life Technologies), 1 µL dNTPs (10 mM each) (New England Biolabs, Ipswich, Mass., USA) and RNase/DNase-free distilled water (filled up to 13 µL/sample) and 1 µg of total RNA. After incubation, a master mix of 4 µL 5× first strand buffer (Life Technologies), 1 µL DTT (Life Technologies), 1 µL RNaseOUT (Life Technologies) and SuperScript III® RT (Life Technologies), were added to each existing sample and incubated for 1 hour at 50° C. and 70° C. for 15 min. Following incubations, 1 µL of RNase H inhibitor (Life Technologies) was added to each sample of cDNA synthesis and incubated for 37° C. for 20 min. Following first strand cDNA synthesis, the PCR reaction was carried, the cDNA was amplified using GoTaq green master Mix (Promega) using 0.3 µM of forward and reverse primers and 4 µL of cDNA template when amplifying for DUX4, and 3 µL of cDNA template when amplifying for Glyceraldehyde-3-phosphate dehydrogenase (GAPDH), in a total volume of 25 µL. The thermal cycling conditions were optimized for each gene (refer to Table 3). 5 µL of PCR products were loaded into their corresponding wells and were visualized in 1.5% agarose gels by electrophoresis. Electrophoresis was performed for 5 minutes at 135 V followed by 25 minutes at 100 V. Following electrophoresis, the agarose gel was stained for 30 minutes under light agitation, using SYBR® safe DNA gel stain (Life Technologies). Band intensity quantification of SYBR safe-stained gels for DUX4 and GAPDH bands was performed using Image J software (NIH, Bethesda, Md., USA).

TABLE 3

Thermocycler conditions for RT-PCR

| Gene | Cycle No. | Temperature (° C.) | Duration |
|---|---|---|---|
| One-Step RT-PCR | | | |
| DUX4 | 1 | 50 | 5 minutes |
|  | 1 | 94 | 2 minutes |
|  | 35 | 94 | 15 seconds |
|  |  | 60 | 30 seconds |
|  |  | 68 | 15 seconds |
|  | 1 | 68 | 5 minutes |
|  | 1 | 4 | 5 minutes |
|  | 1 | 15 | Hold |
| Two-Step RT-PCR | | | |
| DUX4 | 1 | 95 | 2 minutes |
|  | 40 | 95 | 30 seconds |
|  |  | 60 | 30 seconds |
|  |  | 72 | 15 seconds |
|  | 1 | 72 | 5 minutes |
|  | 1 | 4 | 5 minutes |
|  | 1 | 15 | Hold |

Antisense Oligonucleotide Design

Figure 7:
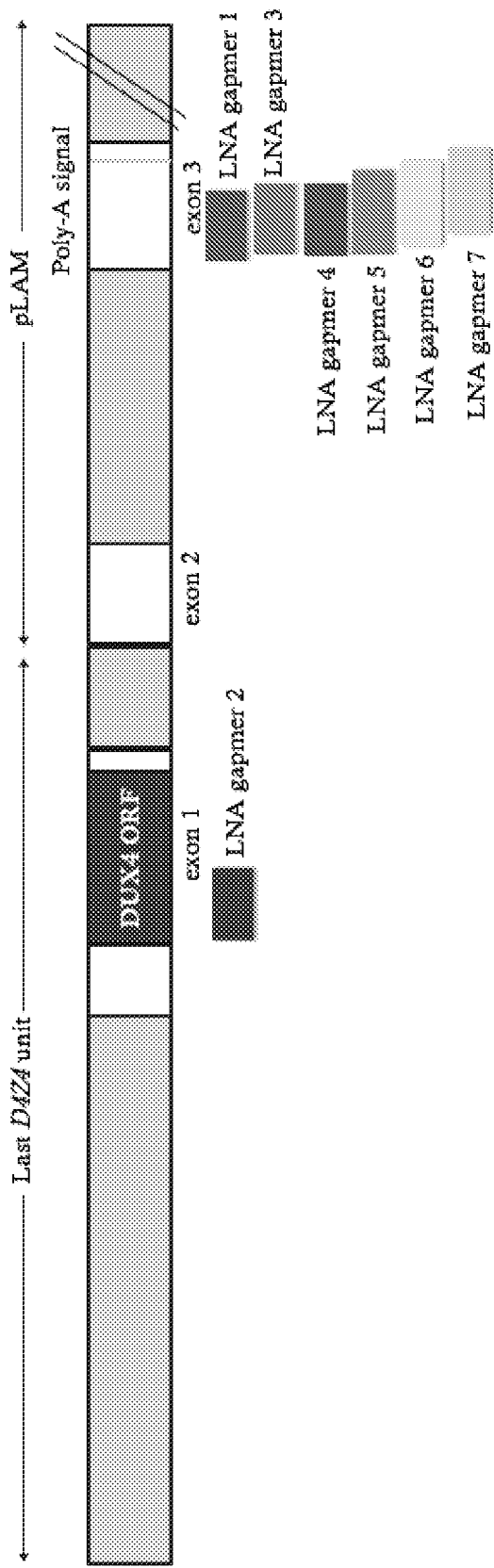
FIG. 7 shows a schematic representation of the location of LNA gapmers 1, 2, 3, 4, 5, 6, 7 on DUX4 mRNA.

LNA gapmer oligonucleotides (positions given in FIG. 7 and Table 4; LNAs 1, 2, 3, MOCK A and MOCK B) were designed to target human DUX4 mRNA and were produced from the nucleotide sequence of the DUX4 gene (SEQ ID NO.: 14). LNA gapmers were between 14-16 nucleotides in length, consisting of a DNA central gap flanked by LNA regions on either side and contain a fully phosphorothioated backbone. The LNA gapmers were synthesized based on predictive software, which selects a target sequence based on local secondary structure, and aligned against ENSEMBL to ensure the most specific LNA gapmer was selected, with minimal off-target hits. Oligonucleotide design parameters such as length, melting temperature, GC content, gap size and self-complementarity were optimized for each individual sequence. A second set of LNA gapmers were designed, designated LNA gapmers 1*, 2*, 3*, 4, 5, 6, 7 and MOCK C. LNA gapmers 1*, 2* and 3* were designed using the same sequences as LNA gapmers 1, 2 and 3; however, the first three nucleotides and the last three nucleotides were confirmed to be LNA flanks surrounding a DNA gap (Refer to Table 4). LNA gapmers 4, 5, 6, 7 and MOCK C also were designed to have a central gap of DNA, flanked by 3 nucleotides of LNA on either side (Table 4). The sequences of LNA gapmers 4, 5, 6, and 7 were based from the LNA gapmer 1 sequence, altered by one or two base pairs upstream or downstream, or increased sequence length by one base pair. Once a variety of sequences were derived from LNA gapmer 1, all possible sequences were aligned against ENSEMBL to ensure there was minimal off-target binding, as well as ensure the GC content of each possible sequence was below 55%.

TABLE 4

LNA gapmer sequences and their characteristics

| LNA Gapmer Name | Position | Target exon | Sequence (5'-3') | Length (bp) | SEQ ID NO. |
|---|---|---|---|---|---|
| LNA gapmer 1 | 98-112 | Exon 3 (3'UTR) | 5'-AGCGTCGGAAGGTGG-3' | 15 | 1 |
| LNA gapmer 2 | 675-688 | Exon 1 (CDS) | 5'-AGATCCCCTCTGCC-3' | 14 | 2 |
| LNA gapmer 3 | 182-197 | Exon 3 (3'UTR) | 5'-ATAGGATCCACAGGGA-3' | 16 | 3 |
| LNA gapmer 1* | 98-112 | Exon 3 (3'UTR) | 5'AGC-GTCGGAAGG-TGG-3' | 15 | 4 |
| LNA gapmer 2* | 675-688 | Exon 1 (CDS) | 5'-AGA-TCCCCTCT-GCC-3' | 14 | 5 |
| LNA gapmer 3* | 182-197 | Exon 3 (3'UTR) | 5'-ATA-GGATCCACAG-GGA-3' | 16 | 6 |
| LNA gapmer 4 | 99-113 | Exon 3 (3'UTR) | 5'-CAG-CGTCGGAAG-GTG-3' | 15 | 7 |
| LNA gapmer 5 | 99-114 | Exon 3 (3'UTR) | 5'-ACA-GCGTCGGAAG-GTG-3' | 16 | 8 |
| LNA gapmer 6 | 100-115 | Exon 3 (3'UTR) | 5-GAC-AGCGTCGGAA-GGT-3' | 16 | 9 |
| LNA gapmer 7 | 101-116 | Exon 3 (3'UTR) | 5'-AGA-CAGCGTCGGA-AGG-3' | 16 | 10 |
| LNA MOCK A | N/A | Negative Control A | 5'-AACACGTCTATACGC-3' | 15 | 11 |
| LNA MOCK B | N/A | Negative Control B | 5'-GCTCCCTTCAATCCAA-3' | 16 | 12 |
| LNA MOCK C | N/A | Negative Control C | 5'-ACT-CTCGTCAATC-CAT-3' | 16 | 13 |
| DNA gap 1 | | Exon 3 (3'UTR) | GTCGGAAGG | 9 | 14 |
| DNA gap 2 | | Exon 1 (CDS) | TCCCCTCT | 8 | 15 |
| DNA gap 3 | | Exon 3 (3'UTR) | GGATCCACAG | 10 | 16 |
| DNA gap 4 | | Exon 3 (3'UTR) | CGTCGGAAG | 9 | 17 |
| DNA gap 5 | | Exon 3 (3'UTR) | GCGTCGGAAG | 10 | 18 |
| DNA gap 6 | | Exon 3 (3'UTR) | AGCGTCGGAA | 10 | 19 |
| DNA gap 7 | | Exon 3 (3'UTR) | CAGCGTCGGA | 10 | 20 |

LNA Gapmer Preparation

LNA gapmers 1, 2, and 3 were purchase and received in a lyophilized form, varying in weight. In order to equate the concentrations of the individual LNA gapmers received, stocks were made for each LNA gapmer. Each LNA gapmer was spun down for 30 seconds using a tabletop microcentrifuge, followed by re-suspension in UltraPure™ RNase/DNase-free distilled water. All stocks were prepared at a 100 µM concentration. Working stocks were then further prepared by diluting each 100 µM LNA gapmer to 10 µM, which is the optimal concentration for storage. Working stocks of 10 µM were aliquoted at 10 µL and were stored at −20° C. Small aliquot amounts are required for storage at −20° C. for LNA gapmers, because no more than 5 freeze/thaw cycles should be performed.

LNA Gapmer Transfection

Figure 8:
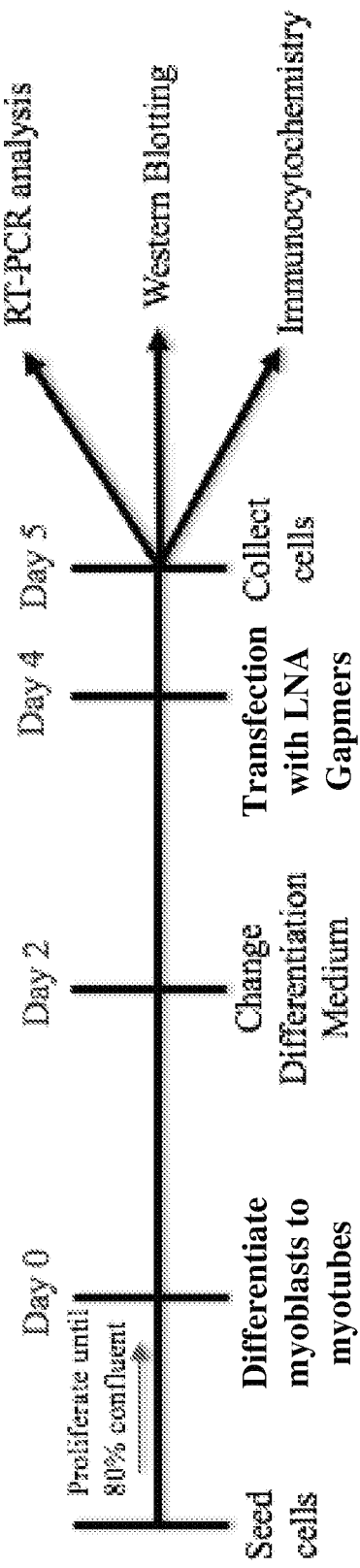
FIG. 8 shows the LNA gapmer transfection schedule. 15ABic myoblasts were differentiated to myotubes after becoming 80% confluent (termed Day 0). Differentiation medium was replaced on Day 2, and differentiated myotubes were transfected with an LNA gapmer or mock LNA gapmer at Day 4. Treated myotubes were collected on Day 5 for RT-PCR analysis, western blotting and immunocytochemistry.

Both 15ABic and 15VBic cell lines were used for LNA gapmer transfection experiments. Briefly, both cell lines were seeded at $1.2\times10^5$ cells/mL into either a single well of a gelatin-coated 12 well plate for RNA analysis, into a single well of a gelatin-coated chamber slide for immunofluorescence, or into a 60 $cm^2$ gelatin-coated petri dish for protein analysis. For LNA gapmer transfections, 15ABic and 15VBic myoblasts were seeded and were left to proliferate for 2-3 days in DMEM/Medium 199 with 0.5% Pen-Strep antibiotics which contains Penicillin (10,000 Units/mL) and Streptomycin (10,000 µg/mL) (Gibco), 0.02M 4-(2-Hydroxyethyl)-1-piperazine ethanesulfonic acid (HEPES, Gibco), Zinc sulfate ($ZnSO_4$, Fisher Scientific), Vitamin $B_{12}$ (Sigma-Aldrich), human hepatocyte growth factor (hrHGF, Chemicon International), human fibroblastic growth factor (hrFGF, Bioionner), 15% Fetal bovine serum (FBS, Gibco) and 0.055 ug/mL Dexamethasone (Sigma-Aldrich) at 37° C. under 5% $CO_2$ (refer to FIG. 8).

Confluent myoblast cultures were differentiated two days after seeding by replacing the growth medium with DMEM/Medium 199 with 1 mM Sodium pyruvate, 2% Horse serum and 0.02 M HEPES (Gibco). Two days after changing to differentiation medium, the spent media was replaced and all myotube cultures were incubated for another two days at 37° C. under 5% $CO_2$ (refer to FIG. 8). On the fourth day after differentiation, LNA gapmer transfection was performed at a concentration of 100 nM and myotubes were incubated with LNA gapmers at 37° C. under 5% $CO_2$, for 24 hours (refer to FIG. 8).

Immunocytochemistry

15Abic and 15Vbic myotubes were seeded at $1.2\times10^5$ cells/mL into a well within the Nunc™ Lab-Tek™ II Chamber Slide™ System. After the 24 hour-incubation period with LNA gapmers (see FIG. 8 for the LNA gapmer transfection protocol), spent medium was aspirated from all wells and 15Abic and 15Vbic myotubes were fixed with 200 µL/well of 4% paraformaldehyde (PFA) (Sigma-Aldrich) for 5 minutes at room temperature. Following fixation, each chamber well was washed with 400 µL/well of 1× PBS containing 0.1% Triton X-100 detergent (PBSTr) for 5 minutes under light agitation (this step was repeated 3 times). Cells were blocked with 200 µL/well of PBS containing 0.5% Triton X-100 detergent and 20% FBS, for 20 minutes under light agitation. After blocking, cells were incubated with primary antibody overnight at 4° C. The rabbit polyclonal antibody anti-MuRF1 at a dilution of 1/300 (ECM Biosciences, KY, USA) was used. After washing with 400 µL/well with 0.1% PBSTr for 5 minutes at room temperature, under light agitation (this step was repeated three times), cells were incubated for 1 hour at room temperature with Alexa Fluor secondary antibodies 1/500 (goat anti-rabbit 594, Life Technologies) when visualizing cells at Day 4 in differentiation medium after 24-hour incubation with LNA gapmers. After incubation, the secondary antibody was washed off using PBSTr for 5 minutes under light agitation (this step was repeated 3 times). Slides were then treated with ProLong® Gold Antifade Mountant containing DAPI (Life Technologies) and stored at 4° C. A Zeiss LSM 710 confocal microscope was used for imaging and Zen Blue imaging software 2012.

Protein Collection

For nuclear extracts, the NE-PER Nuclear and Cytoplasmic Extraction Reagent kit (Thermo Scientific) was used. Spent media was aspirated and 600 µL of Cytoplasmic Extraction Reagent I (CERI) was added to a 60 cm$^2$ petri dish. Cells were detached using a sterile cell scraper, and were collected in a 15 mL tube. The tube was vortexed for 15 seconds to ensure cell pellet suspension and was incubated on ice for 10 minutes. After incubation, 33 µL of ice-cold CERII was added to the tube and vortexed for 5 seconds and incubated on ice for 1 minute. The tube was vortexed again for 5 seconds and was centrifuged at 16,000 rcf at 4° C. for 5 minutes. After centrifugation, supernatant, also referred to as "Cytoplasmic extract", was transferred into another tube and stored at −80° C. The left over pellet containing the nuclei was resuspended in 300 µL using ice-cold Nuclear Extraction Regent (NER). The tube was vortexed for 15 seconds and incubated on ice for 10 minutes (this step was repeated 4 times). A final vortex for 15 seconds was carried out followed by centrifugation at 16,000 rcf for 10 minutes at 4° C. The supernatant, which contains the nuclear extract, was transferred into a pre-chilled tube and was stored at −80° C.

For whole cell extracts, RIPA lysis buffer with 1× Roche cOmplete™ protease inhibitor was used, after spent medium was removed by aspiration. Cells were washed with 5 mL of PBS. 700 µL of the lysis buffer was used per petri dish. Cells were detached well using a sterile cell scraper and the lysis buffer and cells were collected. Collected cells were incubated for 30 minutes on ice. After the incubation the cell lysate was passed through a 21-G needle and cells were spun down at 14,000 g for 15 minutes at 4° C. The supernatant (protein containing) was transferred to a new tube and were stored at −80° C. Protein concentrations were measured using the Pierce BCA Protein Assay Kit, according to the manufacturer's instructions. Standards were prepared as listed in Table 5. For each corresponding round, protein samples were diluted to match the concentration of the healthy 15VBic control sample and samples were stored at −80° C.

TABLE 5

BSA Standards

| Standards (60 µL Total) | Water (µL) | BSA (2 mg/mL) | Final Conc (µg/mL) |
| --- | --- | --- | --- |
| A | 0.00 | 60.00 | 2000 |
| B | 15.00 | 45.00 | 1500 |
| C | 30.00 | 30.00 | 1000 |
| D | 37.50 | 22.50 | 750 |
| E | 45.00 | 15.00 | 500 |
| F | 52.50 | 7.50 | 250 |
| G | 56.25 | 3.75 | 125 |
| H | 59.25 | 0.75 | 25 |
| I | 60.00 | 0.00 | 0 |
| J | 60.00 | 0.00 | 0 |

Immunodetection on Western Blot

All protein samples, whether whole cell or nuclear extracts, were diluted in 4× sodium dodecyl sulfate (SDS) sample buffer. Once samples were diluted in 4× SDS, samples were incubated for 10 minutes at 70° C. using a heating block. Each whole cell extract or nuclear extract was separated by electrophoresis using NuPAGE™ Novex™ 4-12% Bis-Tris Midi Protein Gels (Life Technologies) (9 µg DUX 4 or p53 for nuclear extracts; 18 µg DUX 4 and 9 µg p53 for whole cell extracts). Protein size was marked using the Spectra™ Multicolor Broad Range protein ladder (Thermo Scientific). Testis tissue lysate (Abcam, CA) was used as a positive control for DUX4 Western blots. The electrophoresis ran for 1 hour at 150V. The electrophoresis system, XCell4 SureLock™ Midi-Cell (Invitrogen) was used.

The Novex® Semi-Dry Blotter and extra thick blotting sheets were submerged in transfer buffers and used to transfer protein onto polyvinylidene difluoride (PVDF) membrane (pore size 0.45 µm). The semi-dry transfer equipment was set up by placing the blotting papers, PVDF membrane and gel as follows: Bottom Cathode plate→extra thick blotting sheet in concentrated anode buffer (0.3 M Tris, 20% methanol)→anode buffer (0.03 M Tris, 20% methanol)→PVDF membrane→midi gel→cathode buffer (25 mM Tris, 20% methanol, 40 mM 6-amino-n-hexanoic acid, 0.01% SDS) 4 Top Anode plate. Transfers were run for 30 minutes at 20V. For nuclear-extracted samples, the PVDF membrane was blocked overnight at 4° C. with 5% skim milk in 0.05% Tween 20 detergent in PBS (PBSTw). For whole cell extracted samples, the PVDF membrane was blocked at 4° C. with 5% skim milk in 0.05% Tween 20 detergent in PBS (PBSTw) for 1 hour at room temperature. Primary antibodies were diluted in 5% skim milk blocking solution (9A12 anti-Dux4 at 1/1,000; 7F5 anti-p53 at 1/5, 000 or 1/2,500). For loading control Cofilin primary antibodies (New England Biolabs Cofilin (D3F9) XP® Rabbit mAb) were diluted in 5% skim milk blocking solution to 1/8,000. Primary antibody incubation was under light agitation for 1 hour at room temperature. Primary antibody solutions were decanted, and the PVDF membranes for the corresponding proteins were washed using PBS with 0.05% Tween 20 detergent (PBSTw) for 10 minutes under light agitation (this washing step was repeated three times). Secondary antibody dilutions were 1/10,000 (HRP conjugated goat anti-mouse IgG (H+L) (Bio-Rad) and HRP conjugated goat anti-rabbit IgG (H+L) (Bio-Rad) in PBSTw). Secondary antibody incubation was performed under light agitation for 1 hour at room temperature. Secondary antibody solutions were decanted, and the PVDF membranes for the corresponding proteins were washed using PBSTw for 10 minutes under light agitation (this washing step was repeated three times). The Amersham ECL Select Western blotting detection kit (GE Healthcare) was used for band detection, according to the manufacturer's instructions. Western blot images for nuclear extract samples were taken using the Kodak scientific imager and western blot images for whole cell extracted samples were taken using the ChemiDoc Touch (Bio-RAD). Band intensity quantification was performed using Image J software (NIH, Bethesda, Md., USA).

Statistical Analysis

Analyses were conducted using Graph Prism version 7.0a. The significance of LNA gapmer treatment on FSHD patients' muscle cells was assessed using a one way-ANOVA. Post-hoc comparisons between LNA gapmers were performed using Tukey HSD tests and Dunnett's multiple comparisons test.

Example 2

Evaluation of LNA Gapmers Efficacy In Vitro

Figure 9A:
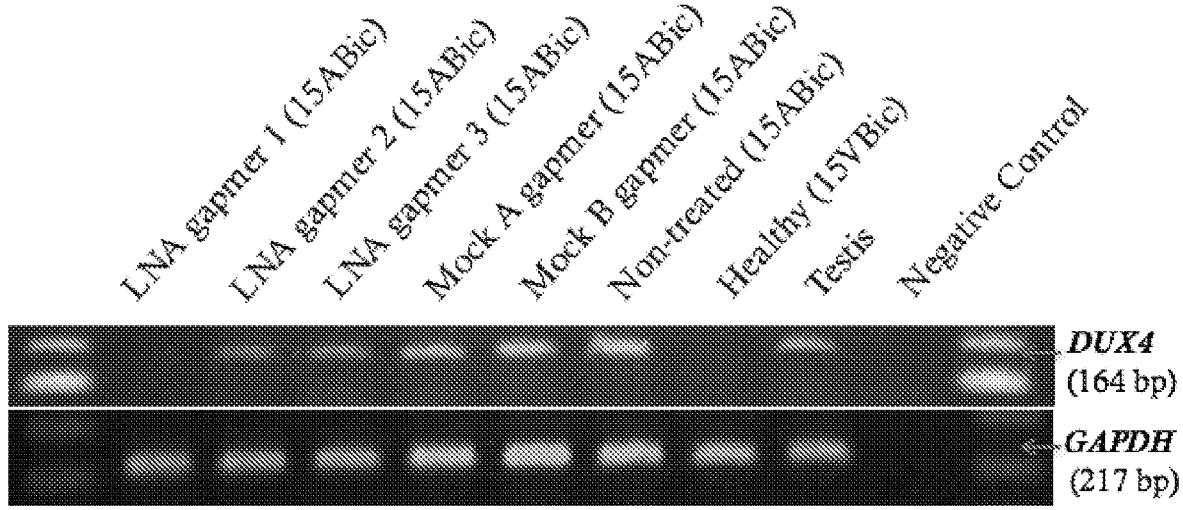
FIG. 9A-FIG. 9B show that treatment with LNA gapmer 1 at Day 4 after differentiation for 24-hours, sufficiently decreases DUX4 expression in 15ABic myotubes.
Figure 9B:
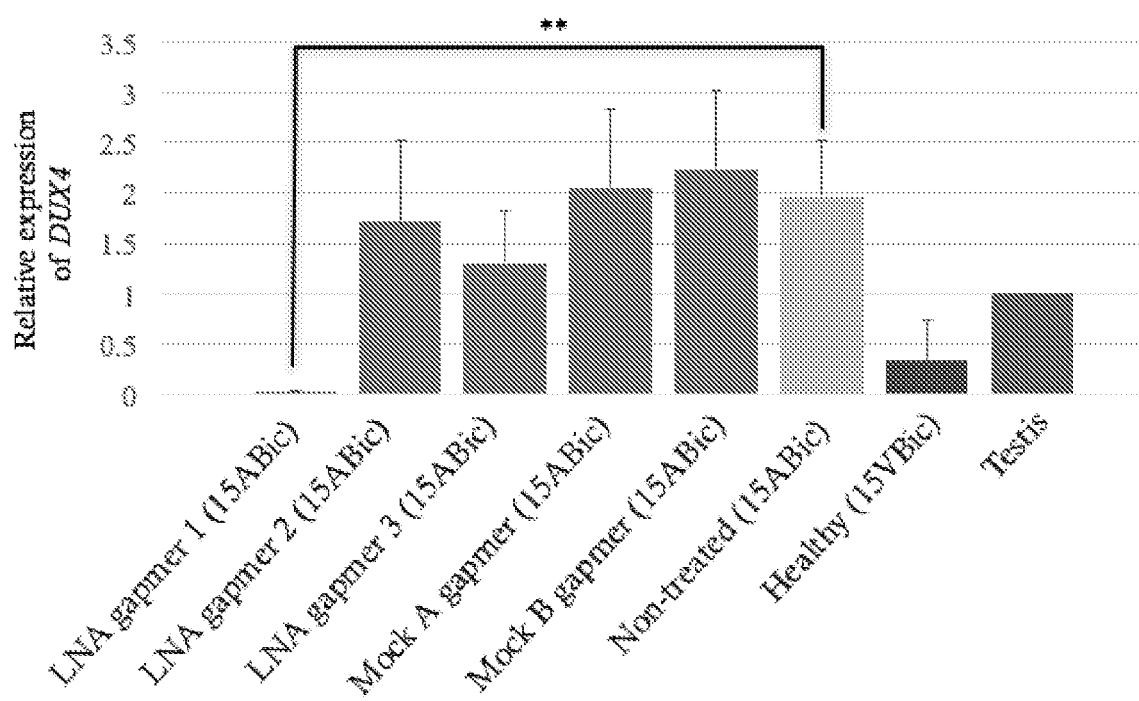

LNA gapmers 1, 2 and 3 were tested at a concentration of 100 nM. LNA gapmers were transfected using the method described in Example 1 to determine the efficacy of these LNA gapmers at suppressing the expression of DUX4 in FSHD patient cells (15ABic). Semi-quantitative RT-PCR results indicated that LNA gapmer 1, targeting exon three of the DUX4 mRNA transcript, sufficiently decreased DUX4 expression levels in 15ABic FSHD myotubes, compared to the non-treated FSHD myotubes ($p<0.005$) (FIG. 9A and FIG. 9B). 15ABic myotubes treated with LNA gapmers 2 or 3 were unable to significantly decrease DUX4 expression levels in non-treated FSHD myotubes (FIG. 9A and FIG. 9B). These results indicate that LNA gapmers targeting exon 3 may be the most effective at suppressing DUX4 at the mRNA level.

Figure 10A:
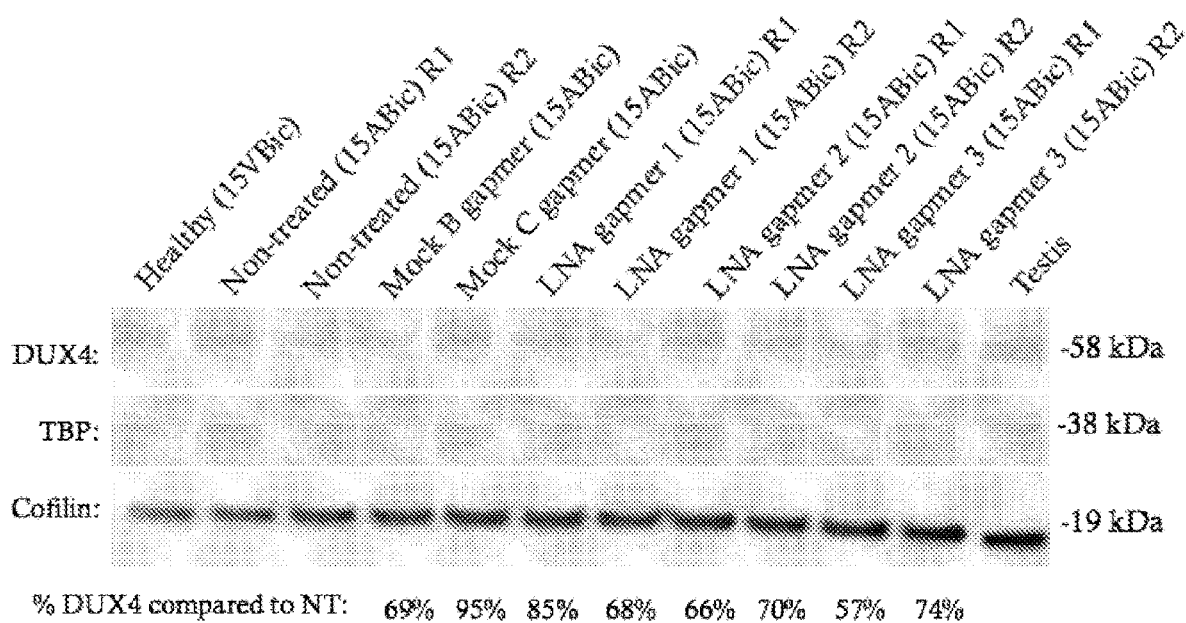
FIG. 10A-FIG. 10B show that LNA gapmers 1, 2 and 3 change DUX4 protein levels in 15ABic cells. Four days after differentiating, FSHD (15ABic) cells were transfected with the indicated LNA gapmer. Data are normalized to Cofilin levels in each sample. Preliminary experiments for each extraction method were performed once. Protein was separated by electrophoresis (4-12% Bis-Tris Midi Protein Gels), transferred to a PVDF membrane and immunodetected with 9A12 anti-Dux4 primary antibody, secondary antibody HRP conjugated goat anti-mouse IgG (H+L) and the Amersham ECL Select Western blotting detection kit. Cofilin was stained with secondary antibody HRP conjugated goat anti-mouse IgG (H+L) and was used as the loading control. The healthy (15VBic) sample represents control myoblasts derived from an unaffected individual confirmed without the FSHD genotype.

After determining the efficacy of LNA gapmers 1, 2 and 3 at the mRNA transcript level, the efficacy of these LNA gapmers was further assessed at the protein level to see if there could also be a reduction in mis-expressed DUX4 protein. Two methods of protein extraction were used for detection of DUX4 protein, nuclear extraction, and whole cell extraction. Due to the low expression levels of DUX4 in cultured cells, utilizing an extraction protocol which could detect the highest quantity of DUX4 protein was vital. Using the nuclear extraction method, the highest quantity of protein yielded was 9 µg, whereas the whole cell extraction method yielded 18 µg of protein. Preliminary results from the nuclear-extracted samples indicated that treatment with LNA gapmers 1 (85% and 68%), LNA gapmer 2 (66% and 67%) and LNA gapmer 3 (57% and 74%) changed the levels of DUX4 protein compared to the NT sample (100%) and Mock C sample (95%) (FIG. 10). Interestingly, Western blotting results showed that both LNA gapmers 2 and 3 changed DUX4 protein levels similarly to LNA gapmer 1 (FIG. 10A), contrary to the semi-quantitative results with LNA gapmers at day 4 after differentiation, 24-hour incubation (FIG. 9A-B). This data suggests that LNA gapmers which target exons one or three may have similar efficacy at the protein level.

Figure 10B:
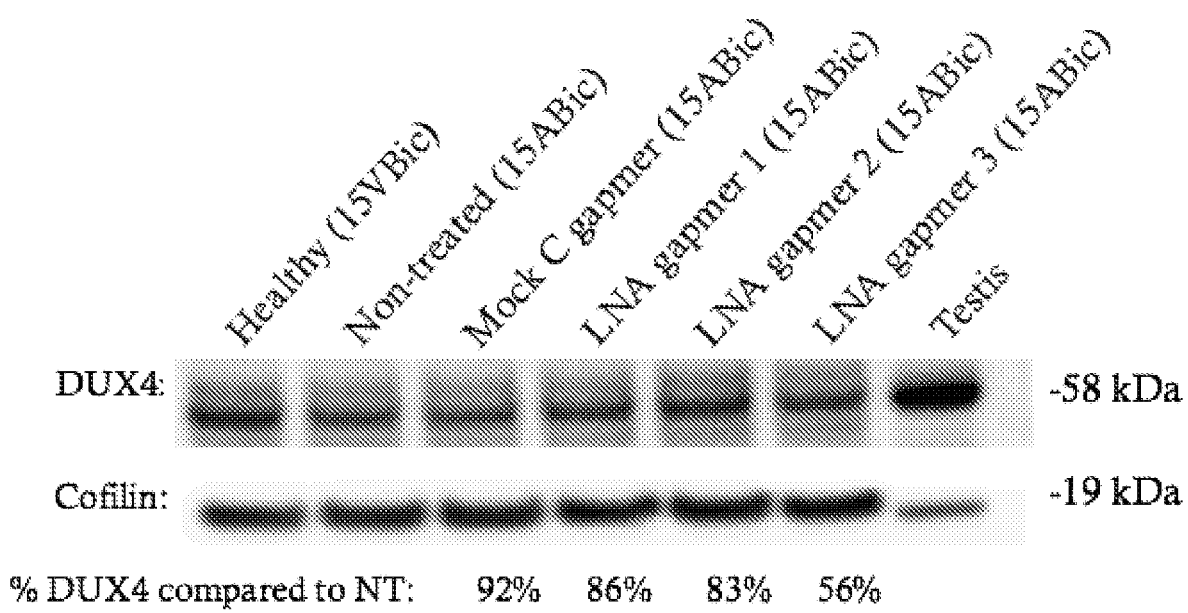

Similar to the western blotting results from nuclear extracts, preliminary results from the whole cell extract samples indicated that LNA gapmers 1 (86%), LNA gapmer 2 (83%) and LNA gapmer 3 (56%) all changed the levels of DUX4 protein in 15ABic myotubes compared to the both the non-treated sample (100%) and the Mock C sample (92%) (FIG. 10B). DUX4 protein levels were changed the most by LNA gapmer 3 (56%) compared to LNA gapmers 1 (86%) and LNA gapmer 2 (83%); however further toxicity tests would have to be performed in order to determine if the change in DUX4 protein levels is being caused by degradation of the protein or if this cause is due to other off-target toxic effects. For whole cell extracts, the Mock B gapmer was not tested because previous results showed that the Mock C gapmer was a better control gapmer to use, showing more similar DUX4 protein levels compared to the NT sample (FIG. 10A).

Figure 11A:
FIG. 11A-FIG. 11B show that LNA gapmers 1*, 3*, 4, 6 and 7 efficiently suppress the expression of DUX4 in 15ABic myotubes at Day 4 after differentiation with 24-hour incubation.
Figure 11B:
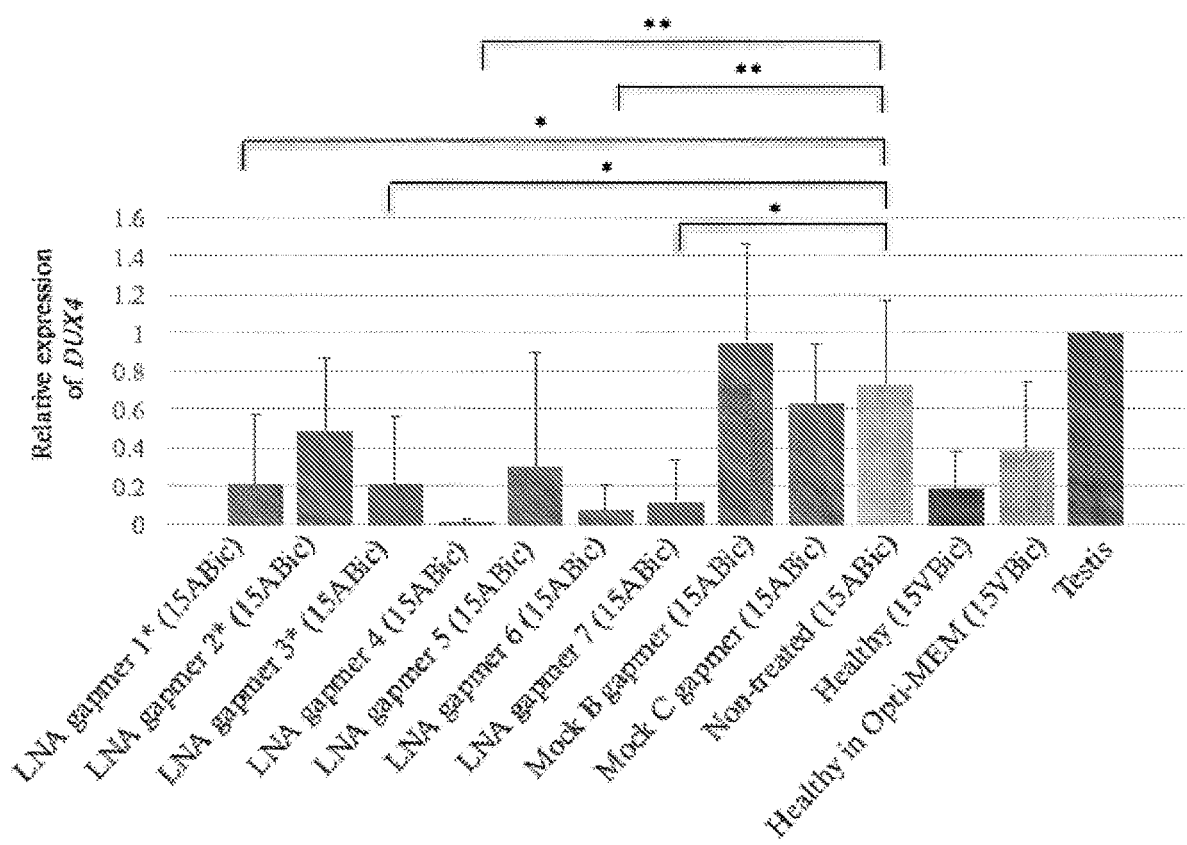

Since transfection with LNA gapmer 1 in 15ABic patient cells showed a consistent trend towards suppression of DUX4, new LNA gapmers were designed with similar sequences to LNA gapmer 1. Newly designed LNA gapmers only deviated by one, two or three base pairs (Table 4). These newly designed LNA gapmers were transfected at a concentration of 100 nM. Semi-quantitative RT-PCR analysis indicated that LNA gapmers 1*, 3*, 7 ($p<0.05$), 4 and 6 ($p<0.005$), all of which targets exon 3 of DUX4 mRNA transcript, sufficiently decrease DUX4 expression levels in 15ABic FSHD myotubes, compared to the NT FSHD myotubes (FIG. 11A-B). Together, these results suggest that at the mRNA level, LNA gapmers targeting exon 3 are more efficient at decreasing DUX4 expression levels in 15ABic myotubes, compared to LNA gapmers targeting exon 2. These semi-quantitative results also demonstrate that because LNA gapmer 3* was able to significantly suppress DUX4 expression levels (FIG. 11B), whereas LNA gapmer 3 was not (FIG. 9B), these results emphasize that specific LNA gapmer sequence design (i.e. LNA flank length and/or DNA gap length) is essential for suppression of DUX4 in FSHD myotubes.

Discussion

Transfection with LNA gapmer 1 at day 4 significantly decreased DUX4 expression in 15ABic FSHD myotubes (FIG. 9). The transfection efficacy seen in this experiment is similar to that seen by Aoki et al. (2013), in which PMO uptake efficacy increased with C2C12 myotube differentiation. Significant suppression of DUX4 by LNA gapmer 1, which targets bases 98-112 of exon 3 compared to LNA gapmer 3, which targets position 182-197 of exon 3, suggests that LNA gapmer sequence location or LNA gapmer accessibility on the DUX4 mRNA transcript may be crucial for efficient suppression of DUX4. Using an iterative HFold method, which predicts a secondary RNA structure with the minimum free energy based on the relaxed hierarchical hypothesis (Jabbari & Condon, 2014), for exon 3, LNA gapmer 1 has 12 targeted bases which are accessible, with 8 of them being G's and C's, which contain stronger bonds in comparison to bonds formed with A's and U's. LNA gapmer 3, however, has 8 targeted bases which are accessible, with only 3 of them being G's and C's (results not shown). The higher accessibility of LNA gapmer 1 on exon 3 of DUX4 mRNA and its quantity of stronger bonds (i.e. GC content), compared to LNA gapmer 3, could suggest why greater efficacy at the mRNA level is seen after transfection with LNA gapmer 1.

Transfection with LNA gapmer 1 sufficiently decreased the expression of DUX4 via semi-quantitative RT-PCR, but contrary to Western Blotting results in both nuclear-extracted samples and whole-cell extracted samples, LNA gapmers 1, 2 and 3 changed DUX4 protein levels in comparison to the NT FSHD sample (FIG. 10). The efficacy of all three LNA gapmers at the protein level suggests two possibilities. First, perhaps sequence design (i.e. LNA flank length, or DNA gap length) or sequence location (i.e. exon 1 or exon 3) does not affect the efficacy of LNA gapmers at the protein level. Second, it is possible that a change in relative DUX4 protein levels is noticed after transfection with LNA gapmers 1, 2 and 3, compared to semi-quantitative RT-PCR results (FIG. 9), because of the specific DUX4 antibody used. For detection of DUX4 at the protein level, a DUX4 antibody was used, which detects the C-terminal region of DUX4 in exon 1, whereas in RT-PCR experiments DUX4 RT-PCR primers targeted exons 2 and 3 of the DUX4 mRNA. For protein analysis, the DUX4 antibody detecting the c-terminal region of DUX4 would only be able to detect fl-DUX4 in FSHD cells, whereas RT-PCR primers may potentially be amplifying both fl-DUX4 and s-DUX4 in FSHD cells. s-DUX4 differs from fl-DUX4 as it removes the carboxyterminal end of DUX4 while maintaining the aminoterminal double-homeobox domains (i.e. exons 2 and 3). Although s-DUX4 is more commonly detected in control myoblasts and in somatic tissues, findings by Snider et al., 2010, where both the fl-DUX4 and s-DUX4 were amplified via RT-PCR in several different FSHD cell lines, supports the theory that RT-PCR results are amplifying both DUX4 isoforms.

These results indicate that LNA gapmer 1 targeting position 98-112 on exon 3 had the greatest efficacy at reducing DUX4 expression levels, compared to LNA gapmers targeting exon 1 or position 182-197 of exon 3. Since LNA gapmer 1 showed the most promise, newly designed LNA gapmer sequences were derived from LNA gapmer 1, deviating by 1, 2 or 3 bps downstream of base pair 98, keeping a sequence length between 15 and 16 nts. All newly designed LNA gapmers contained 3 nucleotide flanks of LNA on either side of the DNA gap which contained between 8-10 nucleotides.

At day 4 after differentiation and with 24-hour incubation with the newly designed LNA gapmers, LNA gapmers 1*, 3*, 4, 6 and 7 significantly reduced the expression of DUX4 in 15ABic FSHD myotubes (FIG. 11).

Example 3

Evaluation of LNA Gapmers Efficacy In Vivo

Figure 12:
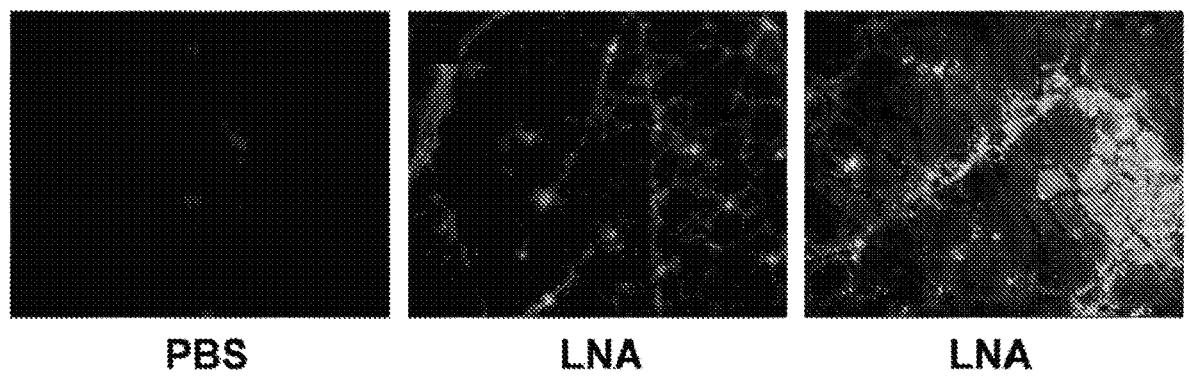
FIG. 12 is a series of pictures showing fluorescein tagged LNA gapmer in skeletal muscle. On the left is a picture of tibialis anterior muscle with a PBS injection to serve as control. In the center, a picture showing LNA gapmer in the interstitial space in the muscles. On the right, a picture showing LNA gapmer in both the interstitial space and myofibers of the muscle.

Adult FLEx-DUX4 mice which aberrantly express DUX4 were used for this study. LNA gapmers entered the interstitial space and myofibers of tibialis anterior muscles 24 hours after one intramuscular injection in two five-week-old FLEx-DUX4 mice (FIG. 12). The LNA gapmers were tagged with fluorescein for localizing the LNA gapmners.

Figure 13:
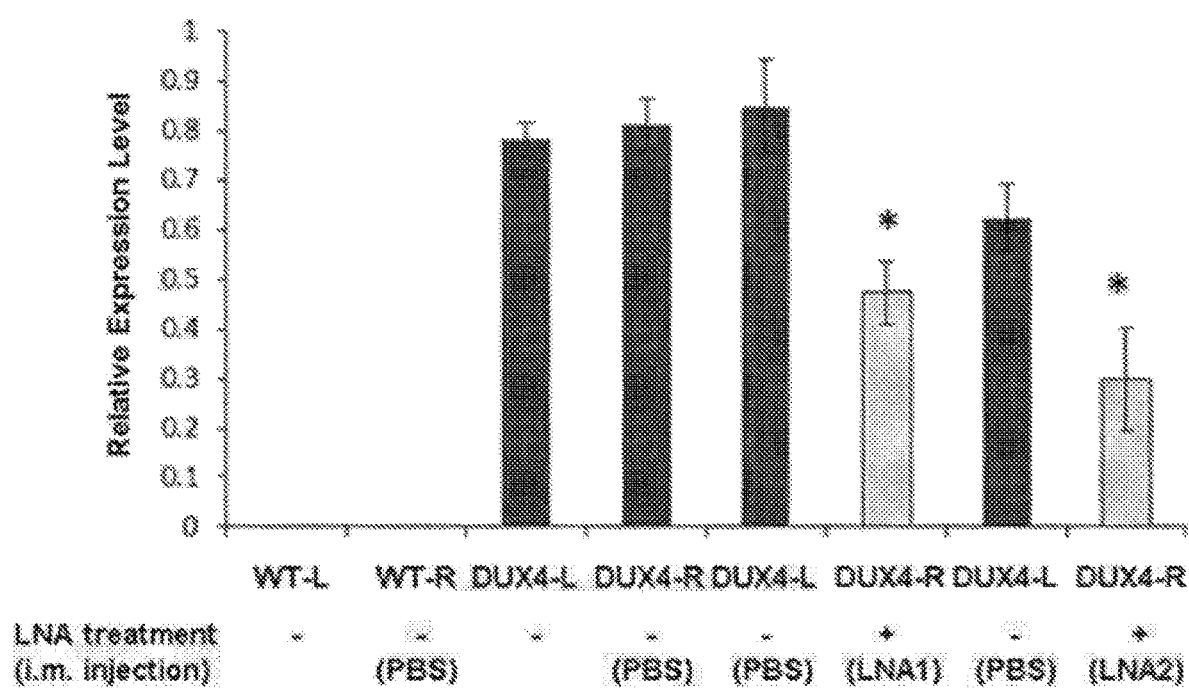
FIG. 13 is a graph showing that LNA1 and LNA2 significantly reduced expression of DUX4 in the muscles of FLEx-DUX4 mice. WT: wildtype mice; DUX4: FLEx-DUX4 mice; L: left leg; R: right leg; PBS: phosphate-buffered saline. *$p<0.05$, N=5.

In a second experiment, three intramuscular injections of LNA gapmers were delivered into tibialis anterior muscles of the right leg every other day. The left leg received PBS injections to serve as control. Wildtype mice and FLEx-DUX4 mice which were not treated with LNA gapmers were used to show baseline expression of the DUX4 gene. FIG. 13 shows that LNA gapmer 1 and LNA gapmer 2, which target two different regions of the DUX4 transcript, knocked down DUX4 expression. There was no DUX4 expression detected in muscles of wildtype mice. The results demonstrated in vivo knockdown of DUX4 using the LNA gapmers.

Example 4

DUX4 LNA and 2'MOE Gapmer Showed Dose-Dependent Efficacy In Vitro

Figure 14:
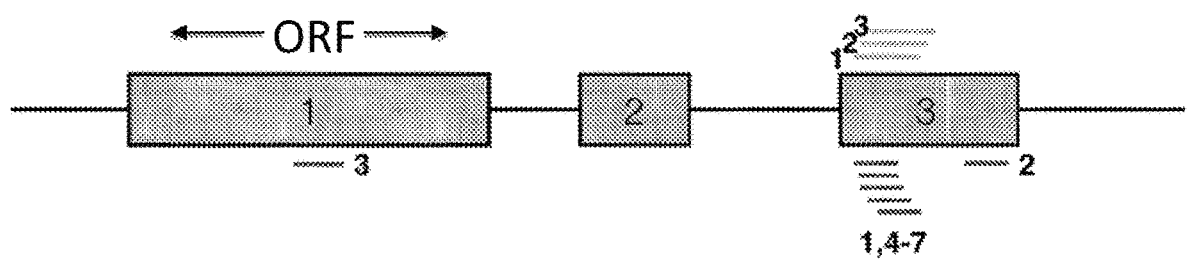
FIG. 14 is a schematic showing the approximate locations of designed LNA (lines below) and 2'MOE (lines above) gapmers along the DUX4 mRNA. Boxes indicate exons and connecting lines indicate introns. The DUX4 open reading frame (ORF) is entirely located within exon 1, and a poly(A) signal (white line) is located in exon 3.
Figure 15A:
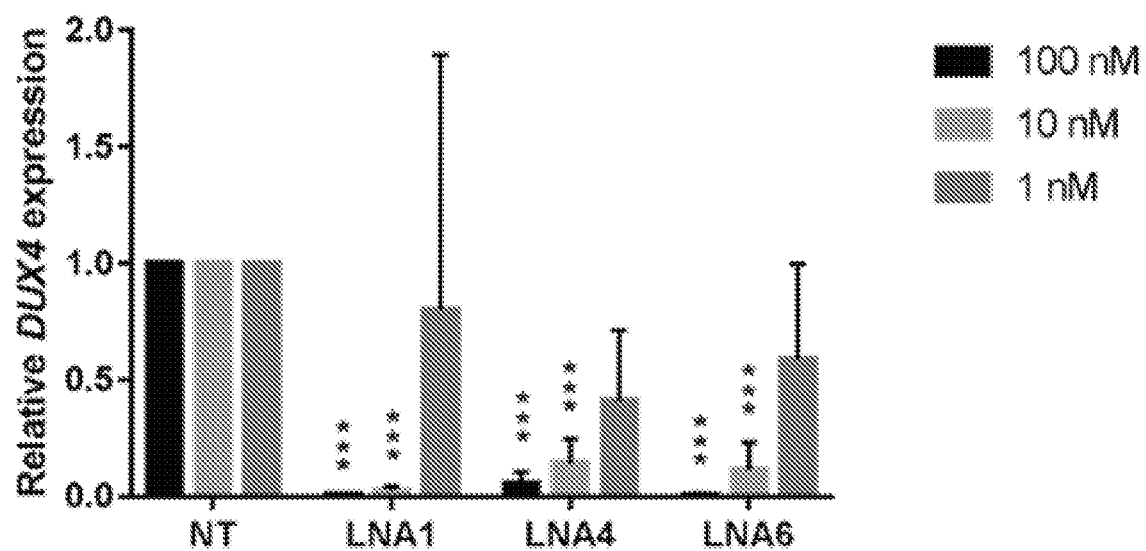
FIG. 15A-FIG. 15B are graphs showing qPCR analysis of DUX4 gene expression as a result of (FIG. 15A) LNA or (FIG. 15B) 2'MOE gapmer treatment at various doses. Immortalized FSHD patient-derived myotubes were lipo-transfected with LNA (1, 4, 6) or 2'MOE gapmers (1, 2, 3) at 13 days post-differentiation and harvested the following day for qPCR analysis of DUX4 expression. Non-transfected (NT) FSHD-affected myotubes were included as a control. Expression levels were normalized using GAPDH. Error bars represent mean±SD of three independent experiments. $p≤0.01$, *$p≤0.001$, one-way ANOVA with Dunnett's multiple comparisons test versus NT; δ$p≤0.05$, δδ$p≤0.01$, one-way ANOVA with post hoc Tukey's test.
Figure 15B:
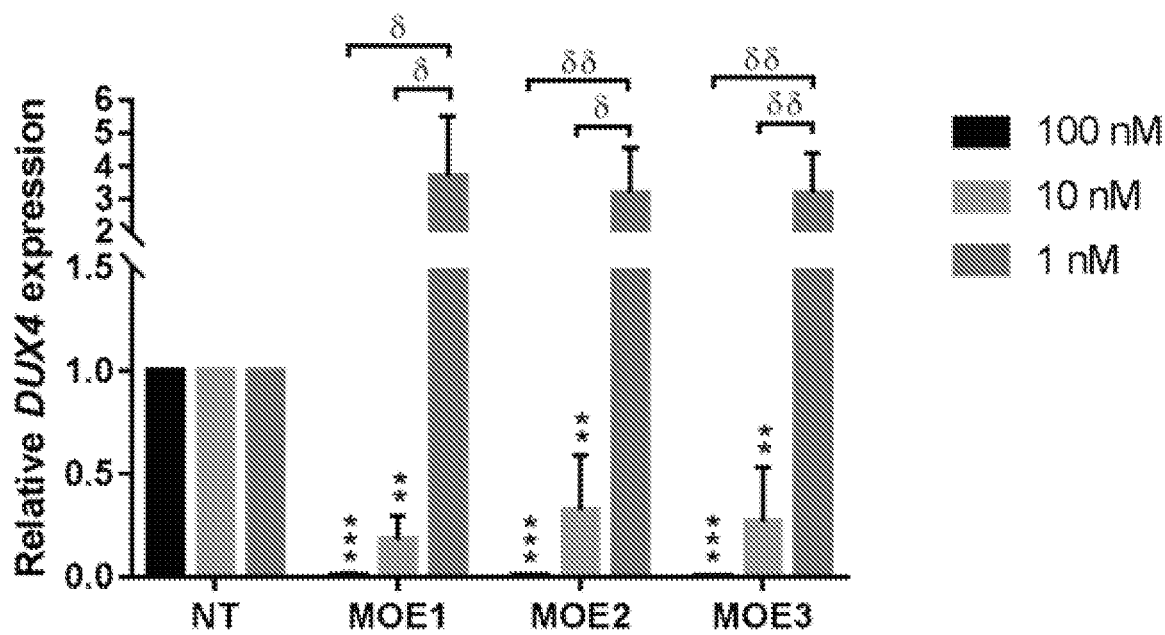

Seven LNA gapmers and three 2'MOE gapmers were designed, as shown in FIG. 14. All gapmers significantly knocked down DUX4 expression in vitro when delivered to immortalized human FSHD myoblasts. LNA gapmers 1, 4 and 6, and 2'MOE gapmer 3 showed the best knockdown in DUX4 expression. Next, various concentrations of LNAs 1, 4, and 6, as well as 2'MOEs 1, 2, and 3 were tested by transfecting immortalized FSHD myoblasts as previously described. Briefly, the myoblasts were transfected with 1, 10 or 100 nM of the gapmers using LIPOFECTAMINE RNAiMAX (Invitrogen) 13 days post-differentiation in KnockOut Serum Replacement (KOSR)-containing medium. Total RNA was extracted 24 hours afterwards and used for qPCR-based quantification of DUX4 expression. For both LNA (FIG. 15A) and 2'MOE gapmers (FIG. 15B), dose-dependent responses to the treatment were observed. DUX4 knockdown was not observed in the cells treated with 1 nM of the gapmers, while 10 nM of gapmers was able to reduce DUX4 expression significantly in the cells. The cells treated with the 100 nM showed the greatest knockdown in comparison to the other two lower concentrations.

Example 5

Off-Targets of DUX4 LNA Gapmers

Figure 16A:
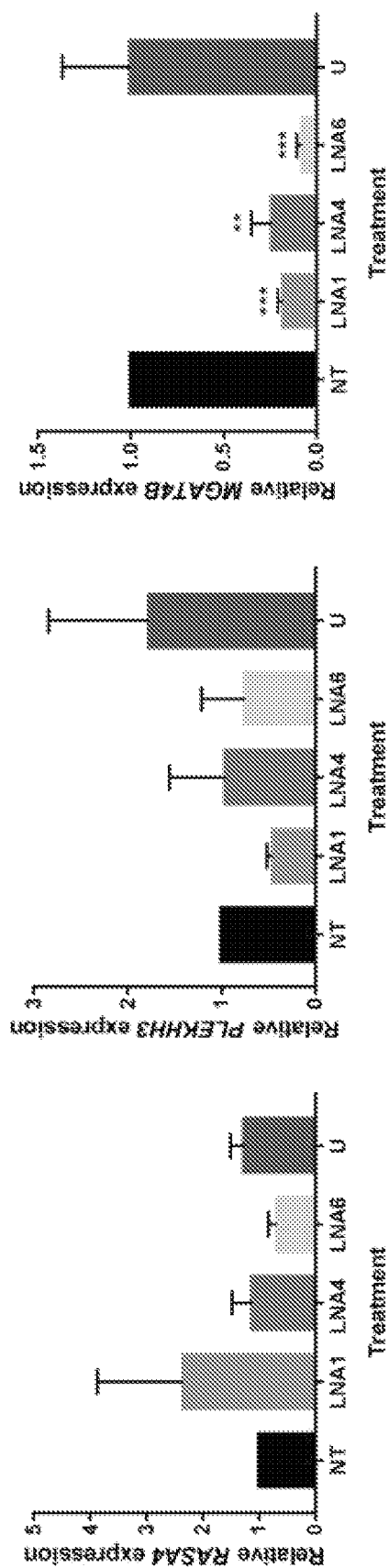
FIG. 16A-FIG. 16B are graphs showing qPCR analysis of RASA4, PLEKHH3, and MGAT4B expression as a result of treatment of immortalized FSHD patient-derived myotubes with LNAs 1, 4, or 6 at a (FIG. 16A) 100 nM or (FIG. 16B) 10 nM dose. Transfection was performed as in FIG. 15A-FIG. 15B. Expression levels were normalized using GAPDH. NT: non-treated FSHD-affected control, U: non-treated FSHD-unaffected control. Error bars represent mean±SD of three independent experiments. $p<0.01$, *$p<0.001$, one-way ANOVA with Dunnett's multiple comparisons test versus NT.
Figure 16B:
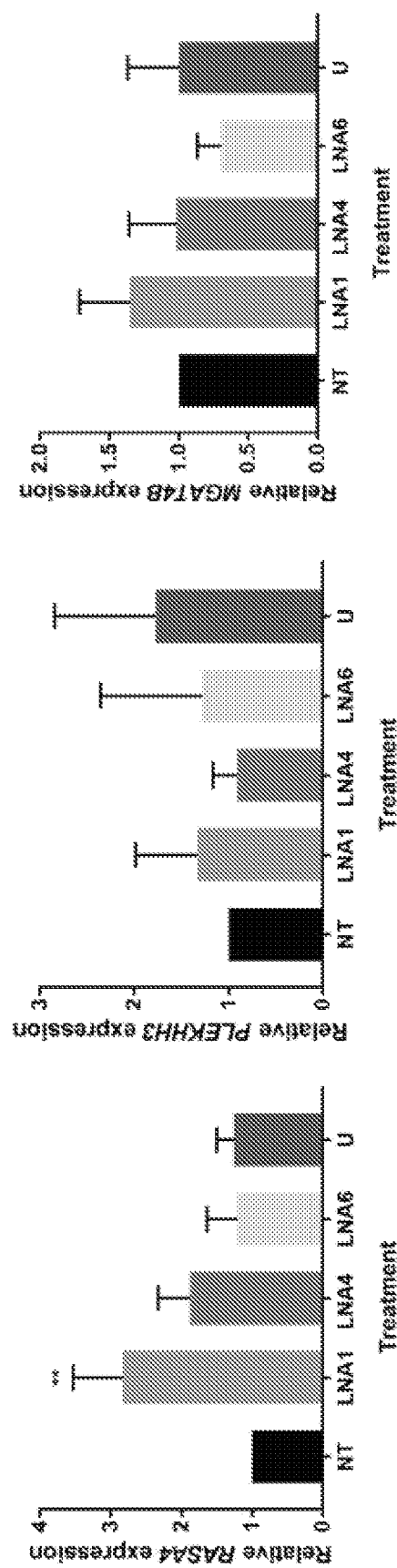

Using GGGenome (publicly available on the worldwide web at gggenome.dbcls.jp), a search engine similar to NCBI's BLAST but more suitable for short sequence inputs, a list of potential off-targets for LNAs 1, 4, and 6 was generated. Out of this list, qPCR-based expression quantification was performed for 3 genes, namely MGAT4B, RASA4, and PLEKHH3, in gapmer-treated immortalized FSHD patient-derived muscle cells; the remaining off-targets were either not expressed or showed low expression (under detection level) in muscle in vitro. At the 100 nM, it was found that RASA4 and PLEKHH3 expression were not affected by LNA gapmer treatment, whereas MGAT4B expression was significantly reduced (FIG. 16A). However, at the 10 nM dose, MGAT4B expression is no longer affected by treatment (FIG. 16B), which suggests that this specific off-target effect can be mitigated by changing the dose at which the gapmer is administered. Using GGGenome as well, a list of potential off-targets for 2'MOEs 1, 2, and 3 was generated to perform qPCR expression analysis of these off-targets. It was observed that the 2'MOE gapmers, owing to their length, have more mismatches to their potential off-targets than do the LNA gapmers. Without being bound by theory, it is believed that this makes the 2'MOE gapmers less susceptible to having off-target effects. However, it remains possible that the longer length of 2'MOE may reduce its in vivo efficacy, which can be tested.

Example 6

Molecular and Cellular Effects of Gapmer Treatment

Myogenic fusion index (MFI) measurement was used to evaluate LNA gapmer functionality in vitro. In this method, immortalized FSHD patient-derived muscle cells are transfected with gapmers according to the usual protocol (however, transfection is done at 4 days post-differentiation), and then subjected to immunostaining two days later for the nuclear marker DAPI and the muscle cell membrane marker desmin. Stained cells are then visualized and photodocumented using a fluorescence microscope with a camera attachment. The MFI is calculated using the following formula for each field of view:

$$MFI = (\text{\# nuclei in myotubes/total \# nuclei}) \times 100$$

Figure 17:
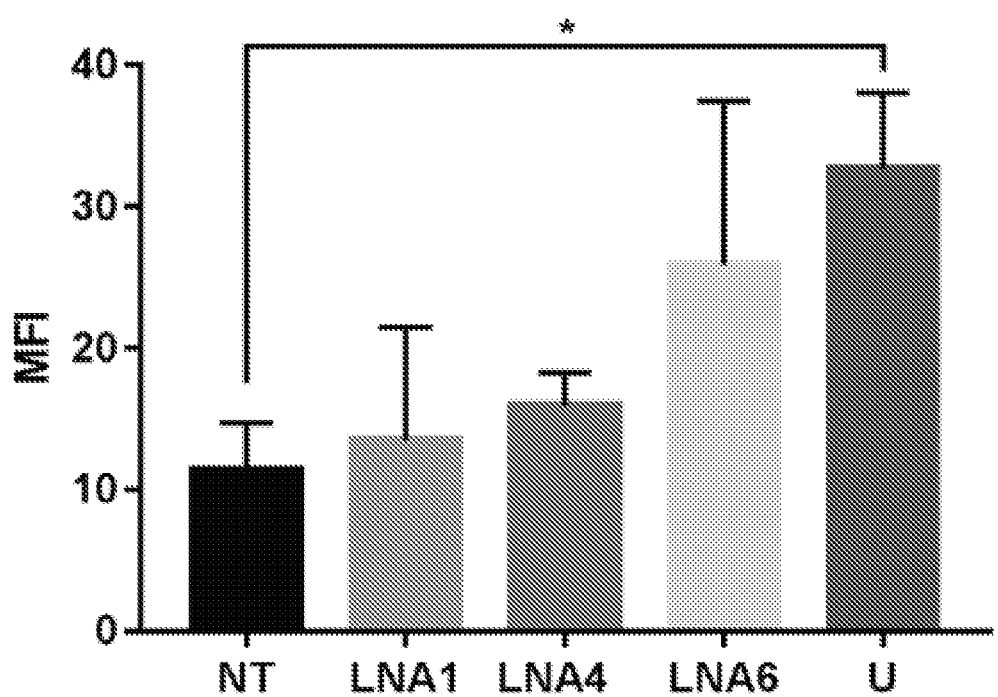
FIG. 17 is a graph showing Myogenic fusion index (MFI) measurements in immortalized FSHD-patient derived cells after treatment with LNA gapmers 1, 4, and 6. Gapmer transfection was done 4 days post-differentiation. Immunostaining using DAPI (nuclei) and desmin (muscle cells) was performed two days later, after which cells were visualized using a fluorescence microscope and nuclei were counted. NT: non-treated FSHD-affected control, U: non-treated FSHD-unaffected control. Error bars represent mean±SEM of three independent experiments. *$p<0.05$, two-tailed t-test.

A myotube is defined as having at least two nuclei shared by a single cytoplasm. A higher MFI indicates better muscle cell fusion. As DUX4 is a negative regulator of muscle differentiation, and since muscle differentiation entails the successful fusion of muscle cell myoblasts into muscle fibers, it was expected that the MFI of FSHD patient-derived muscle cells would increase after gapmer treatment due to reduced DUX4 expression. Indeed, it was found that the MFI observably increased in LNA gapmer-treated cells compared to non-treated cells, particularly for LNA 6 FIG. 17. The experiment is currently being repeated to see if significance can be achieved with a higher sample size. Besides using MFI, an assay is also being developed to check for apoptosis post-gapmer-treatment, as muscle cell death is another hallmark of FSHD DUX4-driven pathology.

As another measure of functionality, RNA sequencing data collected from healthy cells, non-treated FSHD-affected cells, and LNA 4-treated FSHD-affected cells was obtained and analyzed. For this analysis, a "signature" of genes whose expression is affected in FSHD was constructed by comparing the list of significantly up-/down-regulated genes in non-treated FSHD-affected cells (reference is the unaffected healthy cells) to the list of DUX4-dysregulated genes reported by Rickard et al. (2015. Human molecular genetics. 24, 5901-14). The genes that overlapped between the two lists were considered FSHD signature genes, including 86 up-regulated and 5 down-regulated genes. It was then checked how gapmer treatment influenced the expression of genes in this FSHD signature list. Considering only those genes potentially up-regulated by DUX4, it was found that their expression was observably reduced after gapmer treatment. Specifically, 86% of these genes had reduced expression after treatment. Of this 86%, 36% were significantly reduced compared to the non-treated, which indicates the efficacy of the LNA 4 treatment in vitro.

Example 7

Figure 18:
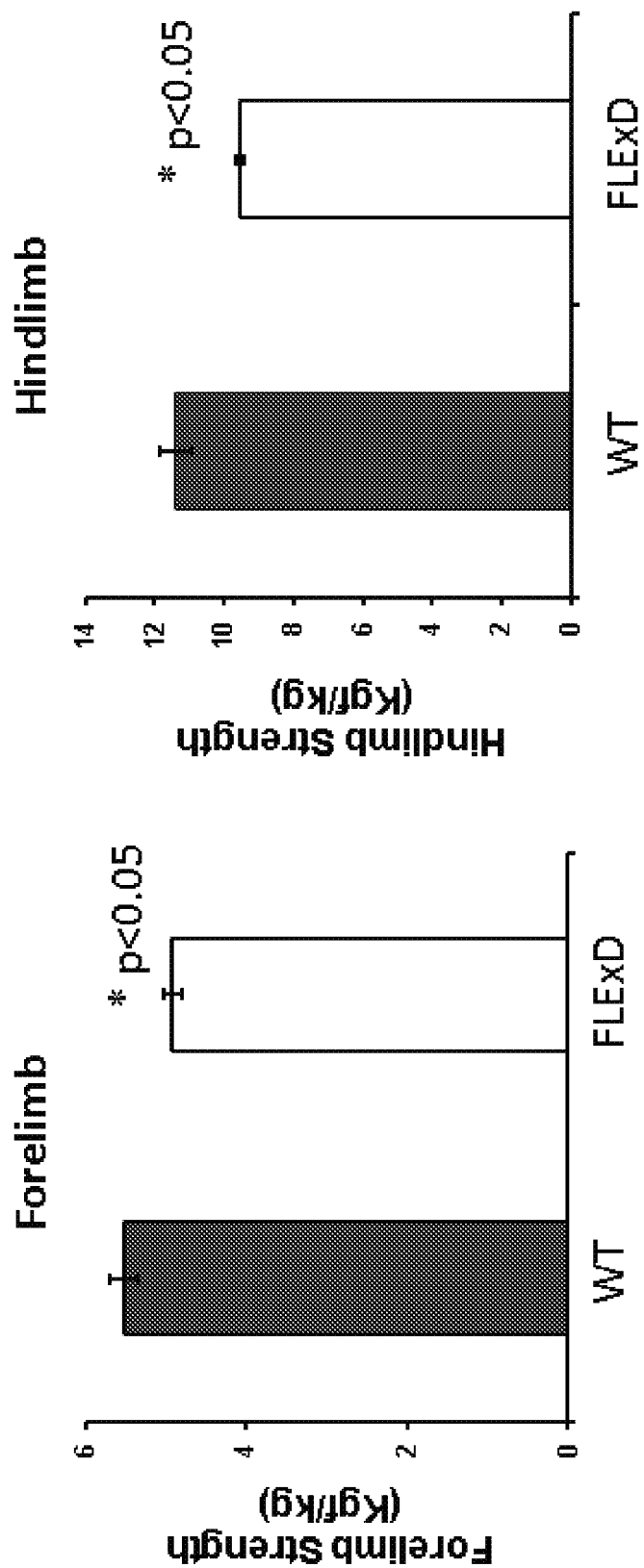
FIG. 18 is a series of graphs showing grip strength testing in single transgenic FLExDUX4 mice at 4 months old (n=8). Mice showed muscle weakness in forelimbs (left) and hindlimbs (right). *$p<0.05$.

Muscle Pathology and Weakness in Single Transgenic FLEx-DUX4 Mice without DUX4 Induction It has been observed that single transgenic, FLExDUX4 mice, expresses DUX4 at a low but easily detectable level, which is slightly higher than another mouse model of FSHD, the D4Z4-2.5 mice (Krom, Y. D. et al. (2013) PLoS genetics. 9, e1003415). This expression level is able to induce mild muscle pathologies in 5-week-old FLExDUX4 mice in a preliminary study (data not shown). In addition, muscle weakness was observed in 4-month-old single transgenic FLExDUX4 mice by grip strength testing (FIG. 18). Additional preliminary studies from trials testing other AONs showed that theses mice showed muscle weakness determined by grip strength as early as 6 weeks. Wheel running data was also collected for analysis. These phenotypic changes and the low DUX4 level recapitulate human FSHD and make this single transgenic model a suitable model for testing therapeutic approaches that knockdown DUX4.

Example 8

LNA Gapmers Reduced DUX4 Expression In Vivo Via Systemic Delivery

Figure 19:
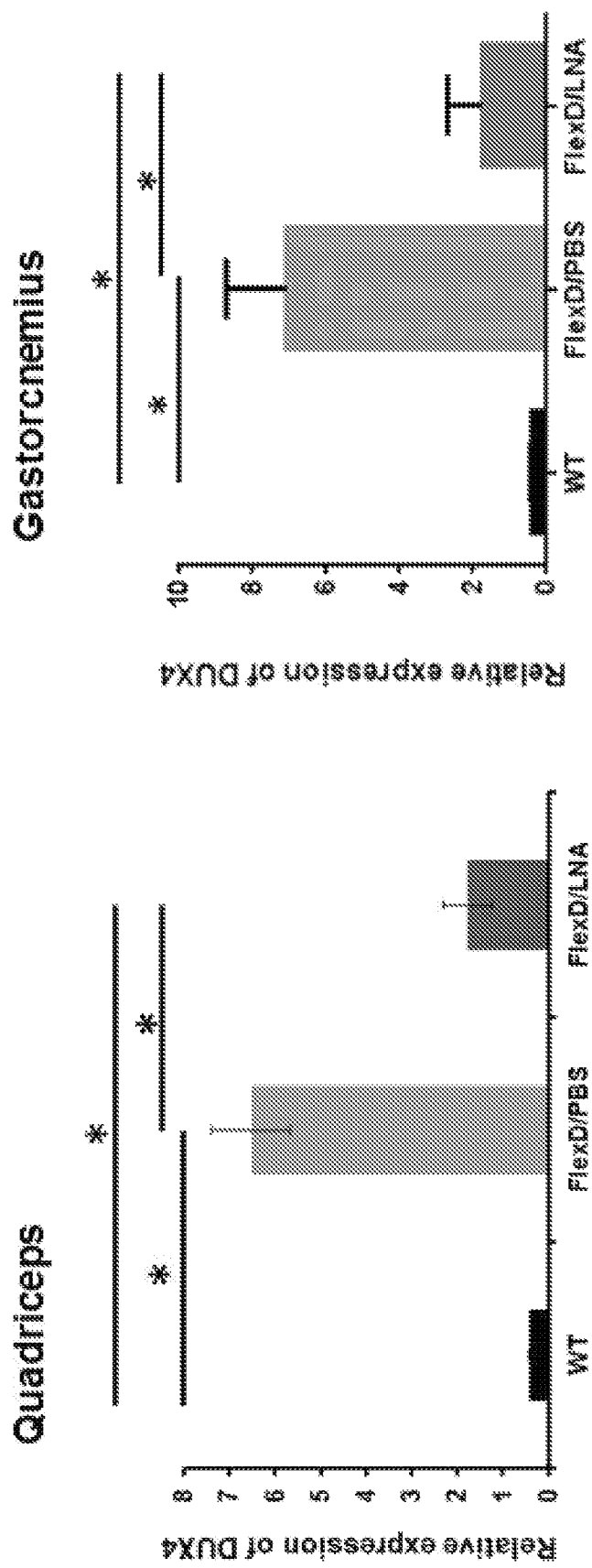
FIG. 19 is a series of graphs showing how LNA gapmer 4 reduced DUX4 expression in vivo after receiving subcutaneous injections every other day for 6 injections. Total RNA samples from quadriceps (left) and gastrocnemius (right) muscles were isolated. Quantitative RT-PCR was performed to determine the expression level of DUX4. GAPDH was used as an internal control. n=4, *$p<0.05$.

Four-week old FLExDUX4 mice were subcutaneously injected with LNA gapmer 4 (20 mg/Kg) in 150 ul PBS every other day. The control group received PBS injections instead. In addition, wildtype littermates receiving PBS injections were included to provide baseline values/negative control. A total of six injections were given and the mice were sacrificed one day after the last injection. Tibialis anterior, gastrocnemius, soleus, quadriceps, biceps, triceps, deltoid, masseter, and diaphragm muscles were collected and snap frozen. Total RNA was isolated from gastrocnemius and quadriceps and real-time quantitative RT-PCR was performed. FIG. 19 showed that DUX4 was significantly suppressed in the FLExDUX4 mice receiving the LNA gapmer 4 in both muscles. Trim36 and Zscan4c which have been reported to be regulated by DUX4 were also examined (Krom et al. (2013); Sharma, V. et al. (2013) PLoS One. 8, e64691). Neither of them was up-regulated in the FLExDUX4 mice, suggesting that DUX4 expression at this level does not induce the specific downstream genes. This observation was confirmed recently by Jones and Jones (2018. PLOS ONE, in press). These DUX4 target genes are usually not detected in human muscle biopsies either. Again, this low expression level of DUX4 in the FLExDUX4 mice shares phenotypic and molecular features of FSHD, supporting that mouse model is suitable for testing the in vivo efficacy of the gapmers.

Example 9

Figure 20:
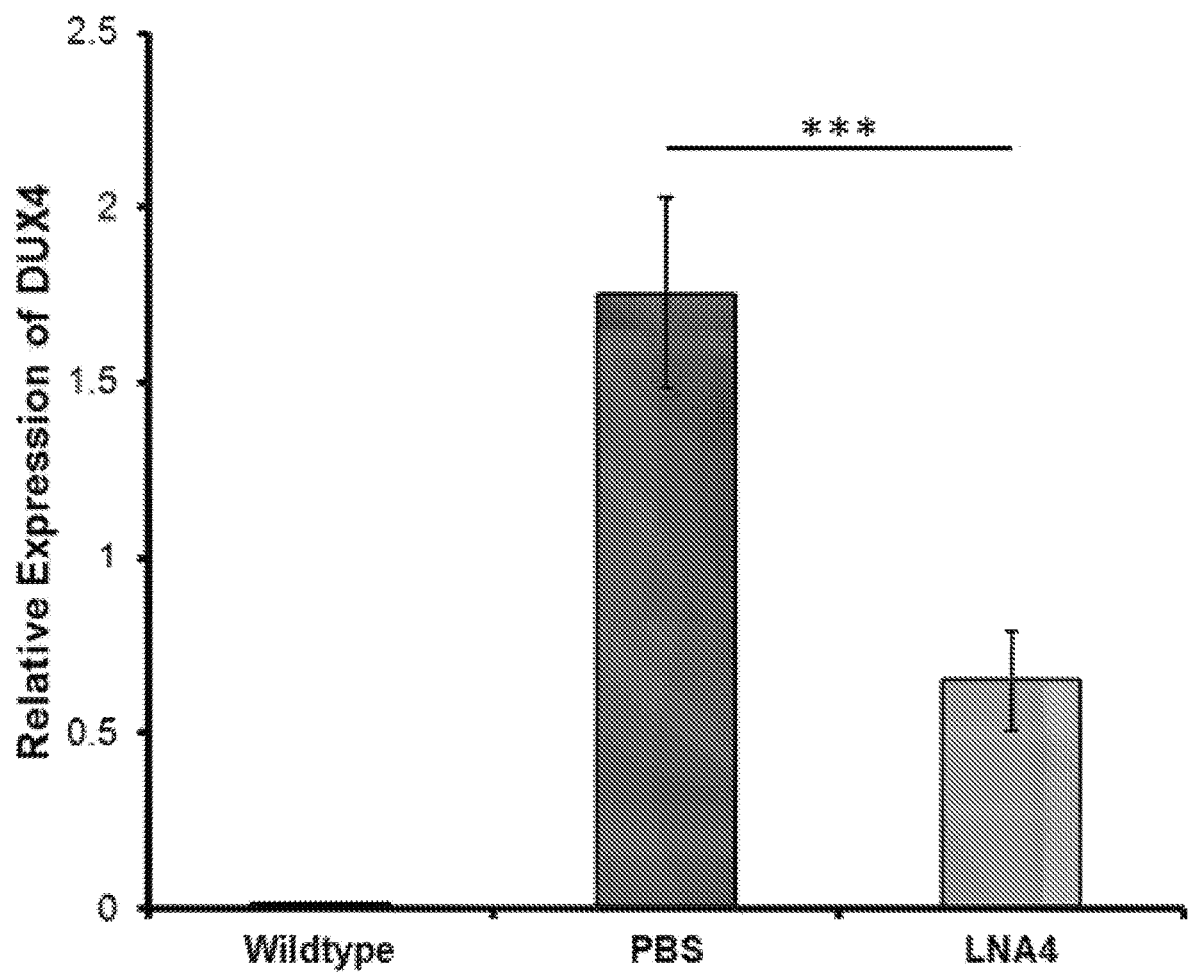
FIG. 20 is a graph showing how LNA gapmer 4 reduced DUX4 expression in vivo after 10 weeks of systemic delivery. Total RNA samples from quadriceps were isolated. Quantitative RT-PCR was performed to determine the expression level of DUX4. GAPDH was used as an internal control. n=5, ***$p<0.005$.
Figure 21:
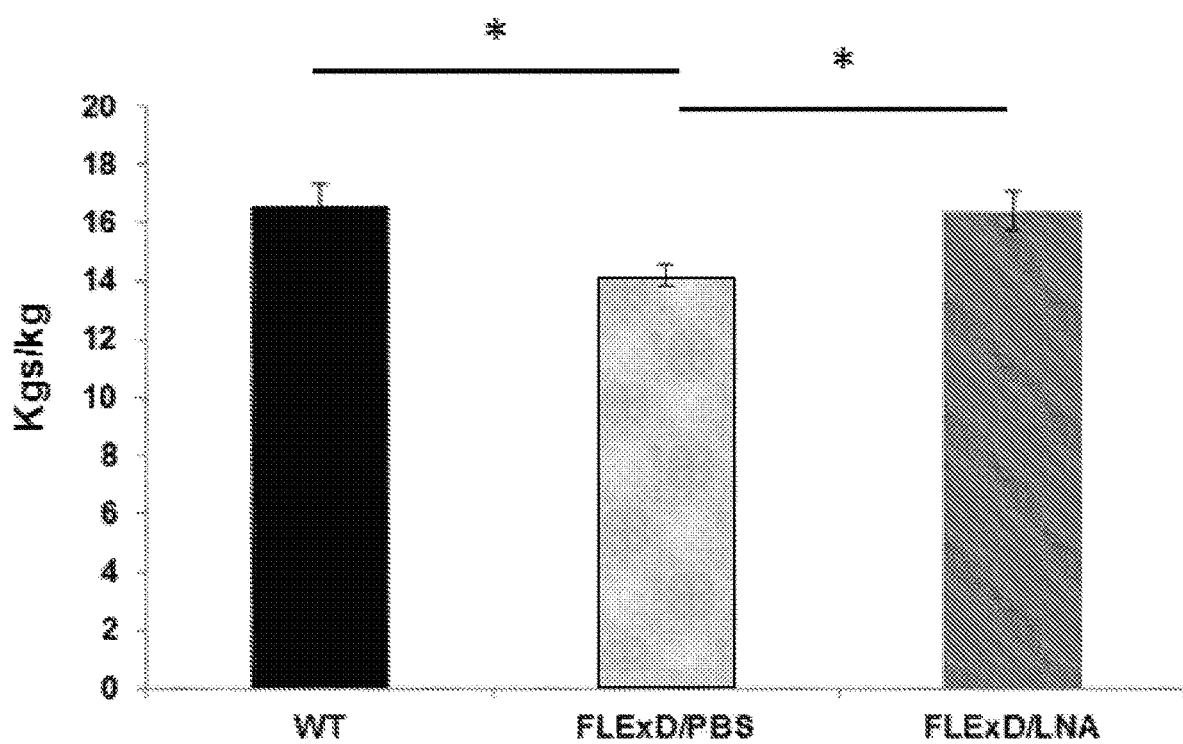
FIG. 21 is a graph showing how LNA gapmer 4 improved muscle function measured by grip strength after 10 weeks of systemic delivery. Grip strength of hind limbs of the FLExDUX4 mice were measured after the mice were treated for 10 weeks. The treatment restored the muscle strength to the level of the wildtype littermates. n=5, *$p<0.05$.

LNA Gapmers Improved Muscle Function Measured by Grip Strength After 10 Weeks of Systemic Delivery A 10-week trial was recently completed, in which 5 weeks old FLExDUX4 mice received LNA gapmer 4 by subcutaneous injections (20 mg/Kg) in 150 ul PBS twice a week for 10 weeks. At the end of the study, grip strength testing was carried out to determine the effect of the treatment on muscle functions. The result showed that, in addition to significant knockdown of DUX4 (FIG. 20), the muscle function of the mice was improved by the treatment (FIG. 21). Body weight data showed no significant difference between the treated and untreated group. Additional data collected during the trial is currently being analyzed, including pathological improvement and muscle weight changes. Tibialis anterior, gastrocnemius, soleus, quadriceps, biceps, triceps, deltoid, masseter, and diaphragm muscles were collected and snap frozen. Blood samples have been collected and will be examined for cardiac, hepatic and renal toxicities.

The invention claimed is:

1. A composition comprising the nucleotide sequence of SEQ ID NO:10, wherein the nucleotide sequence comprises at least one locked nucleic acid (LNA) domain and/or at least one 2'-methoxyethoxy (2'-MOE) domain.

2. The composition of claim 1, wherein the nucleotide sequence comprises a plurality of 2'-methoxyethoxy (2'-MOE) domains.

3. The composition of claim 1, wherein the nucleotide sequence comprises two 2'-methoxyethoxy (2'-MOE) domains.

4. The composition of claim 1, wherein the nucleotide sequence comprises at least one 2'-methoxyethoxy (2'-MOE) domain.

5. A pharmaceutical composition comprising:
   (i) a therapeutically effective amount of the composition of claim 1; and
   (ii) a pharmaceutically acceptable carrier.

6. The pharmaceutical composition of claim 5, wherein the therapeutically effective amount is from about 0.01 µg/ml to about 100 mg/ml.

7. The pharmaceutical composition of claim 5, further comprising a particle that encapsulates the nucleotide sequence.

8. The composition of claim 1, wherein the nucleotide sequence binds to an endogenous DUX4 mRNA and disrupts DUX4 expression.

9. The composition of claim 1, which improves grip strength in FLExDUX4 mouse when the composition is administered in a grip strength test by improving muscle function compared to a mouse to which the composition is not administered.

* * * * *

SEQUENCE LISTING

<160> NUMBER OF SEQ ID NOS: 32

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

```
<400> SEQUENCE: 1
agcgtcggaa ggtgg                                                    15

<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
agatcccctc tgcc                                                     14

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ataggatcca caggga                                                   16

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
agcgtcggaa ggtgg                                                    15

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
agatcccctc tgcc                                                     14

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ataggatcca caggga                                                   16

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 7
cagcgtcgga aggtg                                                      15

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
acagcgtcgg aaggtg                                                     16

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gacagcgtcg gaaggt                                                     16

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
agacagcgtc ggaagg                                                     16

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aacacgtcta tacgc                                                      15

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gctcccttca atccaa                                                     16

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
```
actctcgtca atccat                                                    16

<210> SEQ ID NO 14
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14 gtcggaagg                                                             9

<210> SEQ ID NO 15
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15 tcccctct                                                              8

<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggatccacag                                                           10

<210> SEQ ID NO 17
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17 cgtcggaag                                                             9

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gcgtcggaag                                                           10

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
agcgtcggaa                                                              10

```
<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
```
cagcgtcgga                                                              10

```
<210> SEQ ID NO 21
<211> LENGTH: 2145
<212> TYPE: DNA
<213> ORGANISM: Homo sapiens

<400> SEQUENCE: 21
```

| | | | | | |
|---|---|---|---|---|---|
| tgaggtgcac | gggagcccgc | cggcctctct | ctgcccgcgt | ccgtccgtga | aattccggcc | 60
| ggggctcacc | gcgatggccc | tcccgacacc | ctcggacagc | accctccccg | cggaagcccg | 120
| gggacgagga | cggcgacgga | gactcgtttg | gaccccgagc | caaagcgagg | ccctgcgagc | 180
| ctgctttgag | cggaacccgt | acccgggcat | cgccaccaga | gaacggctgg | cccaggccat | 240
| cggcattccg | gagcccaggg | tccagatttg | gtttcagaat | gagaggtcac | gccagctgag | 300
| gcagcaccgg | cgggaatctc | ggccctggcc | cgggagacgc | ggcccgccag | aaggccggcg | 360
| aaagcggacc | gccgtcaccg | gatcccagac | cgccctgctc | ctccgagcct | ttgagaagga | 420
| tcgcttttcca | ggcatcgccg | cccggggagga | gctggccaga | gagacgggcc | tcccggagtc | 480
| caggattcag | atctggtttc | agaatcgaag | ggccaggcac | ccgggacagg | gtggcagggc | 540
| gcccgcgcag | gcaggcggcc | tgtgcagcgc | ggcccccggc | gggggtcacc | ctgctccctc | 600
| gtgggtcgcc | ttcgcccaca | ccggcgcgtg | ggaacggggg | cttcccgcac | ccacgtgcc | 660
| ctgcgcgcct | ggggctctcc | cacaggggcc | tttcgtgagc | caggcagcga | gggccgcccc | 720
| cgcgctgcag | cccagccagg | ccgcgccggc | agagggggatc | tcccaacctg | ccccggcgcg | 780
| cggggatttc | gcctacgccg | ccccggctcc | tccggacggg | gcgctctccc | accctcaggc | 840
| tcctcggtgg | cctccgcacc | cgggcaaaag | ccgggaggac | cgggaccccgc | agcgcgacgg | 900
| cctgccgggc | cctgcgcgg | tggcacagcc | tgggcccgct | caagcggggc | cgcagggcca | 960
| aggggtgctt | gcgccaccca | cgtcccaggg | gagtccgtgg | tggggctggg | gccggggtcc | 1020
| ccaggtcgcc | ggggcggcgt | gggaaccccca | agcgggggca | gctccacctc | cccagcccgc | 1080
| gccccccggac | gcctccgcct | ccgcgcggca | ggggcagatg | caaggcatcc | cggcgccctc | 1140
| ccaggcgctc | caggagccgg | cgccctggtc | tgcactcccc | tgcggcctgc | tgctggatga | 1200
| gctcctggcg | agcccggagt | ttctgcagca | ggcgcaacct | ctcctagaaa | cggaggcccc | 1260
| gggggagctg | gaggcctcgg | aagaggccgc | ctcgctggaa | gcacccctca | gcgaggaaga | 1320
| ataccgggct | ctgctggagg | agctttagga | cgcggggttg | ggacggggtc | gggtggttcg | 1380
| gggcagggcg | gtggcctctc | tttcgcgggg | aacacctggc | tggctacgga | ggggcgtgtc | 1440
| tccgccccgc | ccctccacc | gggctgaccg | gcctgggatt | cctgccttct | aggtctaggc | 1500
| ccggtgagag | actccactcc | gcggagaact | gcctttcttt | cctgggcatc | ccggggatcc | 1560
| cagagccggc | ccaggtacca | gcaggtgggc | cgcctactgc | gcacgcgcgg | gttttgcgggc | 1620
| agccgcctgg | gctgtgggag | cagcccgggc | agagctctcc | tgcctctcca | ccagcccacc | 1680

| | |
|---|---|
| ccgccgcctg accgcccct cccccacccc accccccacc cccggaaaac gcgtcgtccc | 1740 |
| ctgggctggg tggagacccc cgtcccgcga acaccgggc cccgcgcagc gtccgggcct | 1800 |
| gacaccgctc cggcggctcg cctcctctgc gccccgcgc caccgtcgcc cgcccgcccg | 1860 |
| ggcccctgca gcctcccagc tgccagcacg gagcgcctgg cggtcaaaag catacctctg | 1920 |
| tctgtctttg cccgcttcct ggctagacct gcgcgcagtg cgcaccccgg ctgacgtgca | 1980 |
| agggagctcg ctggcctctc tgtgcccttg ttcttccgtg aaattctggc tgaatgtctc | 2040 |
| cccccacctt ccgacgctgt ctaggcaaac ctggattaga gttacatctc ctggatgatt | 2100 |
| agttcagaga tatattaaaa tgcccctcc ctgtggatcc tatag | 2145 |

<210> SEQ ID NO 22
<211> LENGTH: 4503
<212> TYPE: DNA
<213> ORGANISM: Mus musculus

<400> SEQUENCE: 22

| | |
|---|---|
| gatcttgaga ttcccaggtg ttcaaggtca tgctgtttat atggagctcc aagttgatcc | 60 |
| ttgacccaca ttggaaggag acggtatgtt taccattcta caatgatcga caattctaca | 120 |
| gagagcctta tggcaggcca gcaggacaaa acaatctctc atttgctggc cgtcacctca | 180 |
| ggactactta tttgaagtgt ctccagtgtt caaggctaac tccagagatc taagagcaca | 240 |
| gaacataccg ccagctaaca cagcacatgc aggaagatga tcaactcttt tcttcaacct | 300 |
| gctccatcga aagtgcacaa cctactggtg tctcaagctt ccaggctcct tttcatacag | 360 |
| tctgtgaaag aaaaccttg tgaggtgtct ccatctctct ctgtctctgt ctatctgtct | 420 |
| gtctgtctct gtctctctct ctctccctcc attcctcttt tgctcccct cccatttccc | 480 |
| tccttgcctc catttcacca tctcttccac tctctgtctc catccccatc cttctaccct | 540 |
| cccatattca ctcccccat ccactttcta cctccctact tccctatctc tctctatcca | 600 |
| ttcttcccctt cctctgcac tctgtcactc tctccctacc accctccacc ctctgtccct | 660 |
| aaatcccttc ccccttctc tccacatctg tgtttgtctc tctcttcgtg tcttcctctg | 720 |
| cccctaaccc cacccatggt cgtgacttta tcttcccctta ggatatttgt gagcatgatg | 780 |
| tgtgtgtgtt tgtgtgtgtg tgtgtgtgtg tgtgtgtgtg tgtgtgtttg tgcttgtgtg | 840 |
| tgcccgcatg tgtgcacgtg tttgtgtgtg cgtgtgtgcg tgcatgcatg caaatgtgtg | 900 |
| tatgtgtgtg tttggtctga gggtgtgcct gttcacaatt gtctctgtgt gttgctgcca | 960 |
| ggtgcctagg ggctgtttgg attttcattt aatctcagta caggtgatgt tccctcttgt | 1020 |
| cctcatagca cagtcagact tggaaagtca aggaaggggg tctgaaacac tctagagata | 1080 |
| ggatggaggt ggtgatgtct ttggatctca gaccatgatg ttgggatcgt cagtgtgtgg | 1140 |
| tcttgtcttt gtaagctgat tgaatccgga tgggatgaac tgagcatggc ttccataggg | 1200 |
| cttgggattc ctggaaggct gagtccaatt ccccaagctt tactgaagac tgctccctt | 1260 |
| ctcataggtg tcctggaacc tgtgccacct gccagtcaat gaatgatttg ctgatggga | 1320 |
| atggcgagtc ctctgactct tgtgtgctcc ctgggtgtgg gtctagactg cgacccgt | 1380 |
| ggcttgccag ggatgaggag cctttgggga gattttgctg agtgtcagag gacgcttgag | 1440 |
| gtccgcctcc tggtgccctg atgtcaggtg ccaggcgtgg caggcgtggc gcttcttggc | 1500 |
| ggcaccgcga ggaagggta ggcatgttct gtagcgccta actggtaggt agtgggcggg | 1560 |
| actacctgag cagaggcaga ggtatttaag gggcagtggt cacagccact ctgctggcag | 1620 |
| ttgctgcagc ttgtgcttgt tctgaagctg tcctgagtcg attctcccaa ggtgaggact | 1680 |

```
cctgggaggc cgtcattggc accatggcag aagctggcag ccctgttggt ggcagtggtg    1740
tggcacggga atcccggcgg cacaggaaga cggtttggca ggcctggcaa gagcaggccc    1800
tgctatcaac tttcaagaag aagagatacc tgagcttcaa ggagaggaag gagctggcca    1860
agcgaatggg ggtctcagat tgccgcatcc gcgtgtggtt tcagaaccgc aggaatcgca    1920
gtggagagga ggggcatgcc tcaaagaggt ccatcagagg ctccaggcgg ctagcctcgc    1980
cacagctcca ggaagagctt ggatccaggc cacaggtag aggcatgcgc tcatctggca    2040
gaaggcctcg cactcgactc acctcgctac agctcaggat cctagggcaa gcctttgaga    2100
ggaacccacg accaggcttt gctaccaggg aggagctggc gcgtgacaca gggttgcccg    2160
aggacacgat ccacatatgg tttcaaaacc gaagagctcg gcggcgccac aggaggggca    2220
ggcccacagc tcaagatcaa gacttgctgg cgtcacaagg gtcggatggg gcccctgcag    2280
gtccggaagg cagagagcgt gaaggtgccc aggagaactt gttgccacag gaagaagcag    2340
gaagtacggg catggatacc tcgagcccta gcgacttgcc ctccttctgc ggagagtccc    2400
agcctttcca gtggcacag ccccgtggag caggccaaca gaggcccc actcgagcag    2460 gcaacgcagg ctctctggaa cccctccttg atcagctgct ggatgaagtc caagtagaag    2520
agcctgctcc agcccctctg aatttggatg agaccctgg tggcagggtg catgaaggtt    2580
cccaggagag ctttaggcca caggaagaag caggaagtac aggcatggat acttctagcc    2640
ccagcgactc aaactccttc tgcagagagt cccagccttc caagtggca cagccctgtg    2700 gagcgggcca agaagatgcc cgcactcaag cagacagcac aggccctctg gaactcctcc    2760
tccttgatca actgctggac gaagtccaaa aggaagagca tgtgccagtc ccactggatt    2820
ggggtagaaa tcctggcagc agggagcatg aaggttccca ggacagctta ctgcccctgg    2880
aggaagcagt aaattcgggc atggatacct cgatccctag catctggcca accttctgca    2940
gagaatccca gcctcccaa gtggcacagc cctctggacc aggccaagca ccggcccca    3000 ctcaaggtgg aacacggac cccctggagc tcttcctcta tcaactgttg gatgaagtcc    3060
aagtagaaga gcatgctcca gcccctctga attgggatgt agatcctggt ggcagggtgc    3120
atgaaggttt gtgggagagc ttttggccac aggaagaagc aggaagtaca ggcctggata    3180
cttcaagccc cagcgactca aactccttct tcagagagtc caagccttcc caagtggcac    3240
agcgccgtgg agcgggccaa gaagatgccc gcactcaagc agacagcaca ggccctctgg    3300
aactcctcct ctttgatcaa ctgctggacg aagtccaaaa ggaagagcat gtgccagccc    3360
cactggattg gggtagaaat cctggcagca tggagcatga aggttcccag gacagcttac    3420
tgcccctgga ggaagcagca aattcgggca gggatacctc gatccctagc atctggccag    3480
ccttctgcag aaaatcccag cctccccaag tggcacagcc ctctggacca ggccaagcac    3540
aggcccccat tcaaggtggg aacacggacc ccctggagct cttccttgat caactgctga    3600
ccgaagtcca acttgaggag caggggcctg cccctgtgaa tgtggaggaa acatgggagc    3660
aaatggacac aacacctgat ctgcctctca cttcagaaga atatcagact cttctagata    3720
tgctctgact ccccgacagt acccccttgct tctagaaacc cgagaggcca aagtcctgaa    3780
gagacccgat ttggaactgg agaagggacc catcccagca aggatgtgca tcaaaaaccc    3840
aactccagtg acttcccgaa aatgcaaggt gtctcgctaa ctataaggat tgattgcagg    3900
tggggataat aatgaagtgc cttctccagg gcccggggat taggaaatca gccctgaaag    3960
tgagagagag actctgctac agggacagat ggagaggcca atagtgactc ctcaacaaca    4020
```

| | |
|---|---|
| aggagcctaa agataacccc aaaagaaggg ccacaccaag tgactggctc cagtggaccc | 4080 |
| caggaaatca cacgggacac taggactagg cttcactaca gaggacacac actccctgag | 4140 |
| ggcaatgggg agagtggact ccttccctgg cttatatgga ctgctgttat ccttacagat | 4200 |
| gcttcatgca gagctgtgca aggttttaca ggccagtctt ttaatatcta ctacccatag | 4260 |
| gtcttttgtt tgttttcttt ttcttttttca ctttcttttt catttttttt tcttttttctt | 4320 |
| tttttaggg gtggggttggc tttgttgggt ttggtttggt tttgtgtagt ttgtttccat | 4380 |
| tgctttcaat aaactttatt gattttaaca aaatttgttc gtgtgtttgt gtgctgtttt | 4440 |
| gtgggatgag gggtgggttg aataggctgt tttgttctac ccggagaaag tgcatgagaa | 4500 |
| ttc | 4503 |

<210> SEQ ID NO 23
<211> LENGTH: 792
<212> TYPE: DNA
<213> ORGANISM: Gorilla gorilla

<400> SEQUENCE: 23

| | |
|---|---|
| ctggctgcac ctgccgcagt gcacaggccg gctgaggtgc acgggagccc gccggcctct | 60 |
| ctctgcccgc gtccgtccgt gacattccgg ccggggctca ccgcgatggc cctcccgaca | 120 |
| ccttcggaca gcaccctccc cgcggaagcc cggggacgag gacggcgacg gagactcgtt | 180 |
| tggaccccga gccaaagcga ggccctgcga gcctgctttg agcggaaccc gtacccgggc | 240 |
| atcgccacca gagaacggct ggcccaggcc atcggcattc cggagcccag ggtccagatt | 300 |
| tggtttcaga atgagaggtc acgccagctg aggcagcacc ggcgggaatc tcggccctgg | 360 |
| cccgggagac gcggcccgcc agaaggccgg cgaaagcgga ccgccgtcac cggatcccag | 420 |
| accgccctgc tcctccgagc ctttgagaag gatcgttttc caggcatcgc cgcccgggaa | 480 |
| gagctggcca gagagacggg cctcccggag tccaggattc agatctggtt tcagaatcga | 540 |
| agggccaggc acccgggaca gggtggcagg gcgcccgcgc aggcaggcgg cctgtgcaac | 600 |
| gcggcccccg gcgggtgtca ccctgctccc tcgtgggtcg ccttcgccca caccggcgcg | 660 |
| tggggaacgg ggcttcccgc accccacgtg ccctgcgcgc ctggggctct cccacagggg | 720 |
| gcttccgtga gccaggcggc gagggccgcc cccgtgctgc agcccagccg ggccgcgccg | 780 |
| gcggagggga tc | 792 |

<210> SEQ ID NO 24
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24

| | |
|---|---|
| acagcgtcgg | 10 |

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25

| | |
|---|---|
| cctagacagc gtcggaaggt | 20 |

```
<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cctagacagc gtcggaaggt                                                   20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cctagacagc gtcggaaggt                                                   20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cctagacagc gtcggaaggt                                                   20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cctagacagc gtcggaaggt                                                   20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cctagacagc gtcggaaggt                                                   20

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cccaggtacc agcagacc                                                     18
```

```
<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tccaggagat gtaactctaa tcca                                             24
```